(12) United States Patent
Lombardo et al.

(10) Patent No.: US 7,030,118 B2
(45) Date of Patent: *Apr. 18, 2006

(54) PYRROLOTRIAZINONE COMPOUNDS AND THEIR USE TO TREAT DISEASES

(75) Inventors: Louis J. Lombardo, Belle Mead, NJ (US); Rajeev S. Bhide, Princeton Junction, NJ (US); Kyoung S. Kim, North Brunswick, NJ (US); Songfeng Lu, Raritan, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/441,848

(22) Filed: May 20, 2003

(65) Prior Publication Data

US 2003/0232832 A1    Dec. 18, 2003

Related U.S. Application Data

(60) Provisional application No. 60/382,197, filed on May 21, 2002.

(51) Int. Cl.
*C07D 487/04* (2006.01)
*A61K 31/53* (2006.01)
*A61P 35/00* (2006.01)

(52) U.S. Cl. .................... 514/243; 544/183
(58) Field of Classification Search ............. 544/183; 514/243
See application file for complete search history.

(56) References Cited

U.S. PATENT DOCUMENTS

| 6,518,269 B1 | 2/2003 | Camden et al. |
| 2003/0069244 A1 | 3/2003 | Leftheris et al. |

OTHER PUBLICATIONS

Quintela et al. Tetrahedron 52(8), 3037-3048, 1996.*
Hague et al. Cell Motil. Cytoskeleton, 58(1): 10-16, 2004.*
Cecil Textbook of Medicine, edited by Bennet, J.C., and Plum F., 20th edition, vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
West, Anthony R., Solid State Chemistry and its Applications, Wiley, New York, 1988, pp. 358 & 365.*
Mayer T.U. et al., (1999), Science 286:971-974.
Kapoor T.M. et al., (2000), J. Cell Biol. 150 (5): 975-988.
U.S. Appl. No. 10/289,010, filed Nov. 6, 2002, Pending.
U.S. Appl. No. 09/573,829, filed May 18, 2000, Pending.
U.S. Appl. No. 10/294,281, filed Nov. 14, 2002, Pending.
U.S. Appl. No. 10/633,997, filed Aug. 4, 2003, Pending.
U.S. Appl. No. 10/623,171, filed Jul. 18, 2003, Pending.
U.S. Appl. No. 10/420,399, filed Apr. 22, 2003, Pending.
U.S. Appl. No. 10/420,445, filed Apr. 22, 2003, Pending.
U.S. Appl. No. 10/440,864, filed May 19, 2003, Pending.

* cited by examiner

*Primary Examiner*—Venkataraman Balasubramanian
(74) *Attorney, Agent, or Firm*—Maureen S. Gibbons

(57) ABSTRACT

The present invention provides compounds of formula I

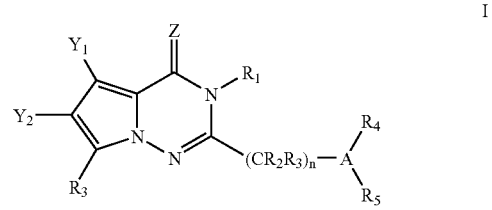

and pharmaceutically acceptable salts thereof useful for inducing mitotic arrest thereby making them useful as anti-cancer agents and other diseases which can be treated by inducing mitotic arrest.

17 Claims, No Drawings

PYRROLOTRIAZINONE COMPOUNDS AND THEIR USE TO TREAT DISEASES

This application claims priority to U.S. Provisional Application Ser. No. 60/382,197, filed May 21, 2002, the contents of which are herein incorporated by reference.

FIELD OF INVENTION

This invention relates to novel compounds that interrupt mitosis thereby making the compounds useful for the treatment of proliferative diseases, such as cancer.

BACKGROUND

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Hence, there is a need to develop new chemotherapeutic drugs that will restore the processes of checkpoint control and programmed cell death to cancerous cells.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis may initiate the spindle checkpoint to arrest cells in mitosis. Of the small molecules that arrest cells in mitosis, those which display anti-tumor activity in the clinic also induce apoptosis, the morphological changes associated with programmed cell death. An effective chemotherapeutic for the treatment of cancer may be one that induces checkpoint control and subsequent programmed cell death.

Most compounds known to cause mitotic arrest and apoptosis act as tubulin binding agents. These compounds alter the dynamic instability of microtubules and indirectly alter the function/structure of the mitotic spindle thereby causing mitotic arrest. Because most of these compounds target the tubulin protein, a component of all microtubules, they may also affect normal cellular processes in which microtubules have a role. Hence, a need exists for small molecules that specifically target proteins associated with proliferating cells, such as Eg5.

Eg5 is one of several kinesin-like motor proteins that are localized to the mitotic spindle and known to be required for formation and/or function of the bipolar mitotic spindle. Recently, there was a report of a small molecule that disturbs bipolarity of the mitotic spindle (Mayer, T. U. et. al. 1999. Science 286(5441) 971–4). More specifically, the small molecule induced the formation of an aberrant mitotic spindle wherein a monoastral array of microtubules emanated from a central pair of centrosomes, with chromosomes attached to the distal ends of the microtubules. The small molecule was dubbed "monastrol" after the monoastral array. This monoastral array phenotype had been previously observed in mitotic cells that were immunodepleted of the Eg5 motor protein.

The distinctive monoastral array phenotype facilitated identification of monastrol as a potential inhibitor of Eg5. Indeed, monastrol was further shown to inhibit the Eg5 motor-driven motility of microtubules in an in vitro assay. Furthermore, monastrol had no apparent effect upon the related kinesin motor or upon the motor(s) responsible for golgi apparatus movement within the cell. Cells that display the monoastral array phenotype, either through immunodepletion of Eg5 or monastrol inhibition of Eg5, arrest in M-phase of the cell cycle. Unfortunately, however, the mitotic arrest induced by either of these mechanisms is transient. (Kapoor, 2000. J. Cell. Biol. 150(5) 975–80). Both the monoastral array phenotype and the monastrol induced cell cycle arrest in mitosis are reversible. Cells recover to form a normal bipolar mitotic spindle, to complete mitosis, and to proceed through the cell cycle and normal cell proliferation. This suggests that a small molecule inhibitor of Eg5 that induced a transient mitotic arrest may not be effective for the treatment of cancer cell proliferation. Nonetheless, the discovery that monastrol causes mitotic arrest is intriguing and hence there is a need to further study and identify compounds that can be used to modulate the Eg5 motor protein in a manner that would be effective in the treatment of human cancers. There is also a need to explore the use of these compounds in combination with other antineoplastic agents.

SUMMARY

The compounds of the invention cause the interruption of mitosis, and as such, can be used to treat proliferative diseases. For example, the compounds of the instant invention can be used as antiproliferatives and anticancer agents. More specifically, the invention comprises a compound of formula I

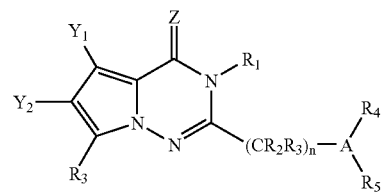

its enantiomers, diastereomers, pharmaceutically acceptable salts, prodrugs and solvates thereof, wherein:

$Y_1$, $Y_2$, and $Y_3$ are independently H, halogen, —CN, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, —$OR_6$, —$NR_7R_8$, —C(=O)$R_9$, —C(=O)$OR_{10}$, —C(=O)$NR_{11}R_{12}$, —OC(=O)$OR_{10}$, —OC(=O)$NR_{11}R_{12}$, —$NR_{13}$C(=O)$OR_{10}$, —$NR_{13}$C(=O)$NR_{11}R_{12}$, —$SO_2R_9$, —$SO_2NR_{11}R_{12}$, —$NR_{13}SO_2NR_{11}R_{12}$;

Z is O or S;

$R_1$ is H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, aralkyl, substituted aralkyl, heteroarylalkyl, or substituted heteroarylalkyl;

$R_2$ and $R_3$ are independently H, halogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, or taken together to form a carbocyclic or heterocyclic ring of 3 to 8 atoms;

n=0 to 4;

A is O, S or N with the proviso that when A is O or S that $R_5$ is nonexistent;

$R_4$ and $R_5$ are independently H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, aralkyl, C(=O)$R_9$, C(=O)O$R_{10}$, C(=O)N$R_{11}R_{12}$, SO$_2R_9$, SO$_2$N$R_{11}R_{12}$, or in the case of A being N, taken together to form a carbocyclic or heterocyclic ring of 3 to 8 atoms;

$R_6$, $R_7$, and $R_8$ are independently H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, —C(=O)H, —C(=O) alkyl, —C(=O)substituted alkyl, —C(=O)alkenyl, —C(=O)substituted alkenyl, —C(=O)alkynyl, —C(=O) substituted alkynyl, —C(=O)aryl, —C(=O)substituted aryl, —C(=O)heteroaryl, —C(=O)substituted heteroaryl, or $R_7$ and $R_8$ may be taken together to form a carbocyclic or heterocyclic ring of 3 to 8 atoms;

$R_9$, $R_{10}$, $R_{11}$, $R_{12}$, $R_{13}$ are independently H, alkyl, substituted alkyl, cycloalkyl, substituted cycloalkyl, substituted cycloalkyl, alkenyl, substituted alkenyl, alkynyl, substituted alkynyl, aryl, substituted aryl, heteroaryl, substituted heteroaryl, or $R_{11}$ and $R_{12}$ may be taken together to form a carbocyclic or heterocyclic ring of 3 to 8 atoms.

The present invention also provides methods for treating a proliferative disease, such as cancer, via modulation of the Eg5 motor protein comprising administering to a mammalian species in need of such treatment an effective amount of the compound of formula I, as defined above.

The present invention also provides methods for inducing apoptosis in a mammal comprising administering to the mammal an effective amount of a compound of Formula I.

The present invention also provides methods for inducing cytotoxicity in a mammal comprising administering to the mammal an effective amount of a compound of Formula I.

The present invention also provides a pharmaceutical product comprising (a) a container; (b) a pharmaceutical composition contained therein wherein said composition comprises the compound of claim 1; and (c) a package insert that indicates that the pharmaceutical composition can be used for the treatment of cancer.

DESCRIPTION

The present invention provides for compounds of formula I, as defined above, pharmaceutical compositions employing such compounds, and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as CCl$_3$ or CF$_3$), alkoxy, alkylthio, hydroxy, carboxy (—COOH), alkyloxycarbonyl (—C(O)R), alkylcarbonyloxy (—OCOR), amino (—NH$_2$), carbamoyl (—NHCOOR— or —OCONHR—), urea (—NHCONHR—) or thiol (—SH). Alkyl groups as defined may also comprise one or more carbon to carbon double bonds or one or more carbon to carbon triple bonds.

The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The terms "cycloalkyl" and "carbocyclic ring" are used interchangeably and herein alone or as part of another group refer to stable, saturated or partially unsaturated cyclic ring hydrocarbyls containing from 3 to 15 carbon atoms, without alternating or resonating double bonds between carbon atoms. Exemplary groups include cyclopropyl, cyclobutyl, cyclopentyl, cyclohexyl, adamantyl, etc. The carbocyclic ring may be optionally substituted meaning that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a diflowerlalkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy), aryl (preferably phenyl), said aryl being optionally substituted by halo, lower alkyl and lower alkoxy groups, —CO$_2$H, —C(=O)H, CO$_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O)NR'R", —CO$_2$NR'R", —C(=O) NR'R", —NR'CO$_2$R", —NR'C(=O)R", —SO$_2$NR'R", and —NR'SO$_2$R", wherein each of R' and R" is independently selected from hydrogen, alkyl, substituted alkyl, and cycloalkyl, or R' and R" together form a heterocyclo or heteroaryl ring.

The terms "alkoxy" or "alkylthio" herein alone or as part of another group denote an alkyl group as described above bonded through an oxygen linkage (—O—) or a sulfur linkage (—S—), respectively.

The term "alkyloxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group.

The term "alkylcarbonyloxy" herein alone or as part of another group denotes an alkylcarbonyl group bonded through an oxygen linkage.

The term "aralkyl" herein alone or as part of another group denotes an aromatic ring bonded through an alkyl group as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "amino" herein alone or as part of another group refers to —NH$_2$. An "amino" may optionally be substituted with one or two substituents, which may be the same or different, such as alkyl, aryl, aralkyl, alkenyl, alkynyl, cycloalkyl, heteroaryl, heteroarylalkyl, heterocycloalkyl, haloalkyl, hydroxyalkyl, alkoxyalkyl, thioalkyl, carbonyl or carboxyl. These substituents may be further substituted with a carboxylic acid, or any of the alkyl or aryl substituents set out herein. In some embodiments, the amino groups are substituted with carboxyl or carbonyl to form N-acyl or N-carbamoyl derivatives.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic.

The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —CO$_2$H, —C(=O)H, —CO$_2$-alkyl, —C(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —CO$_2$NR'R", —C(=O) NR'R", —NR'CO$_2$R", —NR'C(=O)R", —SO$_2$NR'R", and —NR'SO$_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which at least one of the carbon atoms in the ring is replaced by a heteroatom selected from O, S or N, and in which up to three additional carbon atoms may be replaced by said heteroatoms.

The term "heterocyclic ring" herein alone or as part of another group refers to a stable, saturated, or partially unsaturated monocyclic, bridged monocyclic, bicyclic, and spiro ring system containing 5 to 7 ring members of carbon atoms and other atoms selected from nitrogen, sulfur and/or oxygen. Preferably, a heterocyclic ring is a 5 or 6-membered monocyclic ring and contains one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower] alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower] alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring may be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

Suitable examples of salts of the compounds according to the invention with inorganic or organic acids are hydrochloride, hydrobromide, sulfate, trifluoroacetate, methanesulfonate, maleate, fumarate, and phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I. Various forms of prodrugs are well known in the art. For examples of such prodrug derivatives, see: (a) Design of Prodrugs, edited by H. Bundgaard (Elsevier, 1985); and Methods in Enzymology, Vol. 42, pp. 309–396, edited by K. Widder et al., (Academic Press, 1985); (b) A Textbook of Drug Design and Development, edited by Krosgaard-Larsen and H. Bundgaard, Chapter 5, "Design and Application of Prodrugs," by H. Bundgaard, pp. 113–191 (1991); (c) H. Bundgaard, Advanced Drug Deliver Reviews, 8, pp. 1–38 (1992); (d) H. Bundgaard et al., Journal of Pharmaceutical Sciences, 77, 285 (1988); and (e) N. Kayeka et al., Chem. Phar. Bull., 32, 692 (1984).

In general, the instant invention comprises a compound of formula I

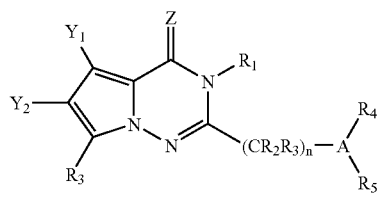

I its enantiomers, diastereomers, pharmaceutically acceptable salts, prodrugs and solvates thereof, wherein:

$Y_1$, $Y_2$, and $Y_3$ are independently H, halogen, —CN, alkyl, substituted alkyl, alkenyl, substituted alkenyl, alkynyl, substituted alkynyl, aryl, substituted aryl, heteroaryl, substituted heteroaryl, —$OR_6$, —$NR_7R_8$, —$C(=O)R_9$, —$C(=O)OR_{10}$, —$C(=O)NR_{11}R_{12}$, —$OC(=O)OR_{10}$, —$OC(=O)NR_{11}R_{12}$, —$NR_{13}C(=O)OR_{10}$, —$NR_{13}C(=O)NR_{11}R_{12}$; —$SO_2R_9$, —$SO_2NR_{11}R_{12}$, —$NR_{13}SO_2NR_{11}R_{12}$;

Z is O or S;

$R_1$ is H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, aralkyl, substituted aralkyl, heteroarylalkyl or substituted heteroarylalkyl;

$R_2$ and $R_3$ are independently H, halogen, alkyl, substituted alkyl, alkenyl, substituted alkenyl, alkynyl, substituted alkynyl, aryl, substituted aryl, heteroaryl, substituted heteroaryl, or taken together to form a carbocyclic or heterocyclic ring of 3 to 8 atoms;

n=0 to 4;

A is O, S or N with the proviso that when A is O or S that $R_5$ is nonexistent;

$R_4$ and $R_5$ are independently H, alkyl, substituted alkyl, alkenyl, substituted alkenyl, alkynyl, substituted alkynyl, aryl, substituted aryl, heteroaryl, substituted heteroaryl, $C(=O)R_9$, $C(=O)OR_{10}$, $C(=O)NR_{11}R_{12}$, $SO_2R_9$, $SO_2NR_{11}R_{12}$, or in the case of A being N, taken together to form a carbocyclic or heterocyclic ring of 3 to 8 atoms;

$R_6$, $R_7$, and $R_8$ are independently H, alkyl, substituted alkyl, alkenyl, substituted alkenyl, alkynyl, substituted alkynyl, aryl, substituted aryl, heteroaryl, substituted heteroaryl, —C(=O)H, —C(=O)alkyl, —C(=O)substituted alkyl, —C(=O)alkenyl, —C(=O)substituted alkenyl, —C(=O)alkynyl, —C(=O)substituted alkynyl, —C(=O)aryl, —C(=O)substituted aryl, —C(=O)heteroaryl, —C(=O)substituted heteroaryl, or $R_7$ and $R_8$ may be taken together to form a carbocyclic or heterocyclic ring of 3 to 8 atoms;

$R_9$, $R_{10}$, $R_{11}$, $R_{12}$, $R_{13}$ are independently H, alkyl, substituted alkyl, alkenyl, substituted alkenyl, alkynyl, substituted alkynyl, aryl, substituted aryl, heteroaryl, substituted heteroaryl, or $R_{11}$ and $R_{12}$ may be taken together to form a carbocyclic or heterocyclic ring of 3 to 8 atoms.

The invention further provides a pharmaceutical composition comprising a compound of formula I, as defined above, and a pharmaceutically acceptable carrier. Optionally the pharmaceutical composition may further comprise at least one other anti-cancer agent formulated as a fixed dose.

The invention also provides a method for treating a proliferative disease via modulation of the Eg5 motor protein, and/or, inducing apoptosis comprising administering to a mammalian species in need of such treatment an effective amount of a compound of formula I, as defined above. In another embodiment, the invention provides a method for treating a proliferative disease via modulation of the Eg5 motor protein comprising administering to a mammalian species in need of such treatment an effective amount of a compound of formula I, as defined above, in combination (simultaneously or sequentially) with at least one other anti-cancer agent. In a preferred embodiment, the proliferative disease is cancer.

Certain compounds of formula I may generally be prepared according to the following schemes and the knowledge of one skilled in the art. Solvates (e.g., hydrates) of the compound of formula I are also within the scope of the present invention. Methods of solvation are generally known in the art. Accordingly, the compounds of the instant invention may be in the free or hydrate form, and may be obtained by methods exemplified by the following schemes below.

Appropriately substituted 1-aminopyrrole-2-carboxylic acid ester starting materials 5 may be prepared following the reaction in Scheme 1. In this manner, a pyrrole-2-carboxylic acid ester 3 may be reacted with 2,4-dinitrophenolamine (4) in the presence of sodium hydride in DMF to afford the desired materials in high yield. The compounds may be isolated as their corresponding hydrochloride salts by treatment with HCl in dioxane, followed by filtration and washing with ether. 1-Aminopyrroles may also be prepared by reaction with alternative aminating reagents, such as, but not limited to, chloramine.

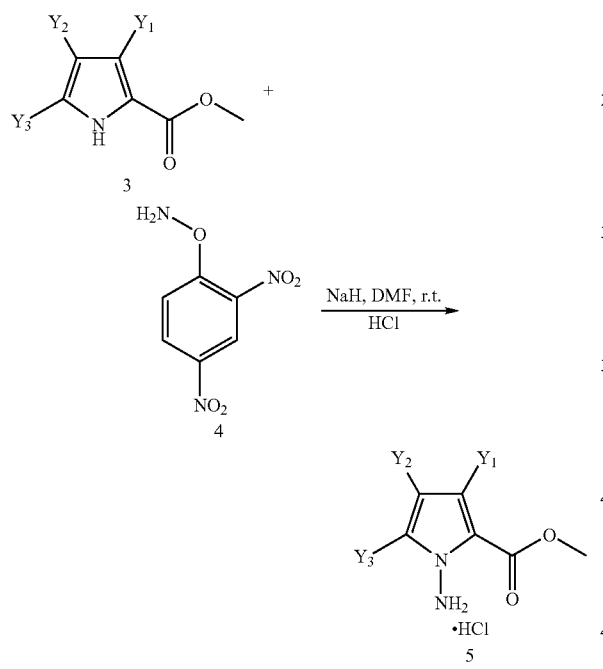

The preparation of 2-aminothioamide starting materials for construction of the pyrrolotriazinone ring may be prepared from appropriately protected amino acids as described in Scheme 2. Thus, reaction of a protected amino acid 6 with a desired amine using standard carbodiimide coupling procedures affords an amide 7 which may be converted to the thioamide 8 by treatment with Lawesson's reagent (2,4-bis (4-methoxyphenyl)-1,3-dithia-2,4-diphosphetane-2,4-disulfide) and pyridine in dichloroethane.

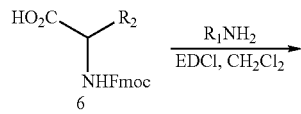

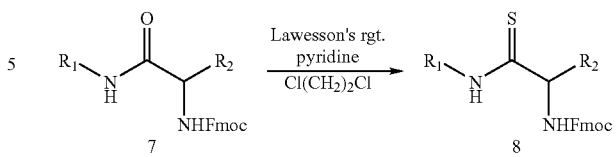

Formation of the pyrrolotriazinone ring may be accomplished following the reaction sequence described in Scheme 3. Coupling of an appropriately substituted 1-aminopyrrole (compound 5 from Scheme 1) with a 2-aminothioamide (compound 8 from Scheme 2) in the presence of a coupling reagent, such as EDCI in dichloromethane and DMF affords an amidine intermediate 9. Cyclization of the amidine intermediate 9 to the pyrrolotriazinone ring system 10 can be accomplished by heating at 130–150° C. in xylene followed by removal of the FMOC protecting group using piperidine in DMF.

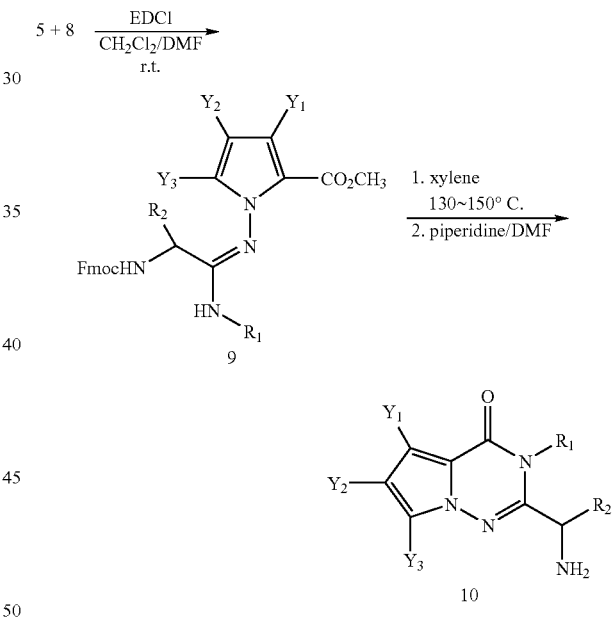

Alternatively, the pyrrolotriazinone ring system can be prepared using the reaction sequences outlined in Schemes 4–6. Optionally substituted 1-aminopyrrole carboxamide 11 can be acylated with a protected amino acid 12 using standard peptide coupling conditions to provide the amidine intermediate 13 (Scheme 4). Ring closure under basic conditions in refluxing ethanol provides the protected pyrrolotriazinone 14. N-Alkylation of intermediate 14 in the presence of cesium carbonate and an alkyl bromide, such as benzyl bromide affords compound 15. Removal of the BOC protecting group of compound 15 under acidic conditions in dioxane generates the functionalized pyrrolotriazinone 10.

Scheme 4
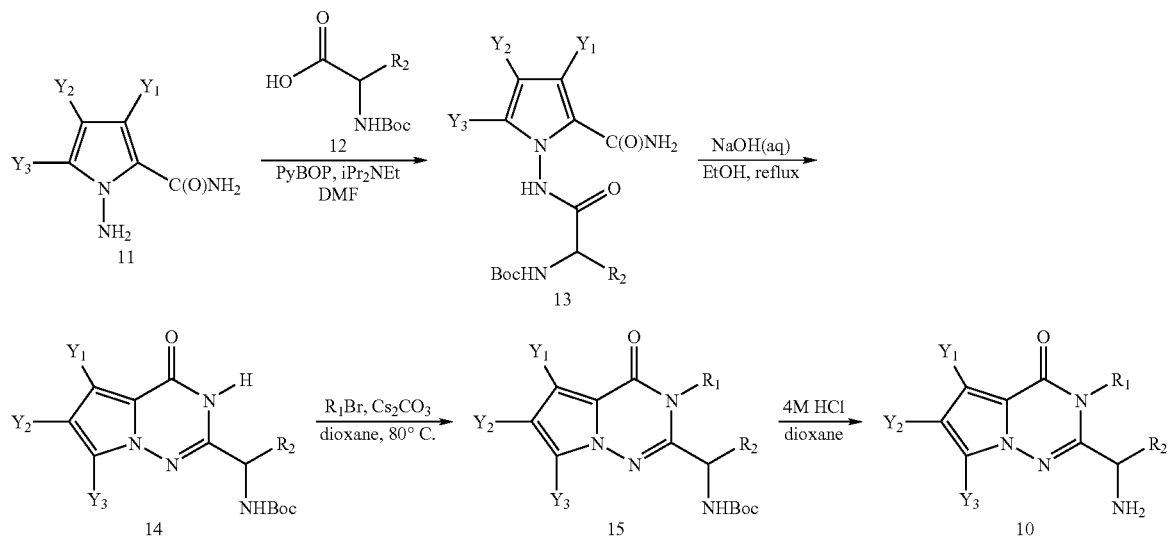
Scheme 5
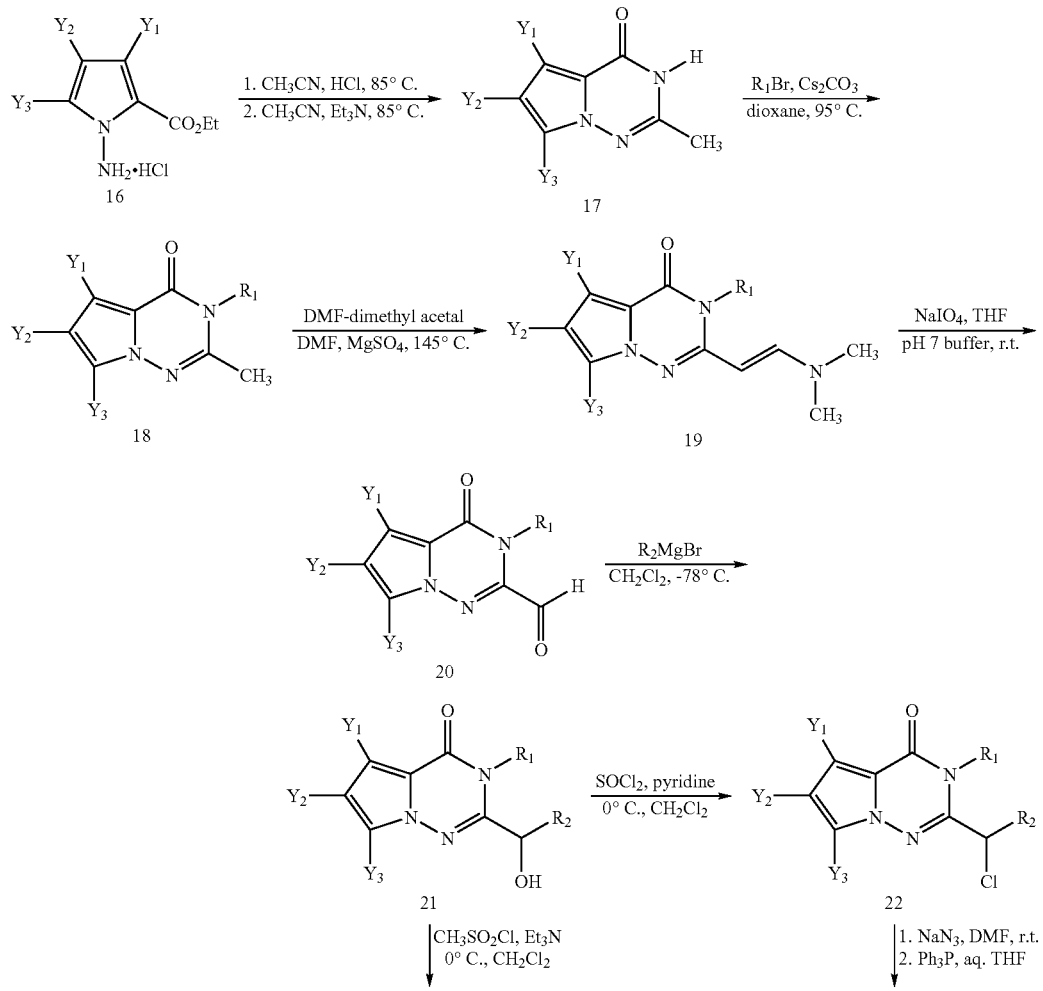

-continued

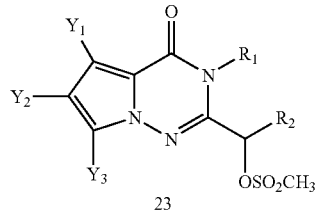
23

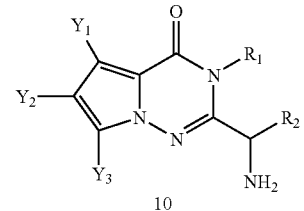
10

Appropriately substituted 1-amino pyrrole-2-carboxylic acid ester 16 can be cyclized in the presence of acetonitrile at elevated temperatures to give 2-methyl pyrrolotriazinone derivative 17 (Scheme 5). N-Alkylation of compound 17 can be carried out as described above for compound 14 in Scheme 4. Enamine derivative 19, prepared from compound 18 using N,N-dimethylformamide dimethyl acetal at 145° C., can be converted to aldehyde 20 using sodium periodate and pH 7 buffer at room temperature. Grignard addition to compound 20 at low temperature in dichloromethane provides the secondary alcohol 21 which can be converted under mildly basic conditions to the chloride 22 or mesylate 23 using thionyl chloride or methansulfonyl chloride, respectively. Conversion of the chloride 22 to the amino pyrrolotriazinone intermediate 10 can be accomplished using sodium azide in DMF followed by reduction of the azide intermediate with triphenylphosphine in the presence of aqueous THF.

The appropriately substituted 1-amino pyrrole-2-carboxylic acid ester 16 can be converted to an amidine intermediate 24 at elevated temperatures under acidic conditions (Scheme 6). Cyclization of compound 24 with cesium carbonate followed by N-alkylation with an alkyl bromide provides pyrrolotriazinone 25. Selective hydroxylation of compound 25 with Davis' reagent (2-benzenesulfonyl-3-phenyloxaziridine, *J. Org. Chem.* 1982, 47, 1774–1775 and *J. Org. Chem.* 1984, 49, 3241–3243, incorporated herein by reference, in the presence of a base, such as KHMDS (potassium bis(trimethylsilyl)amide) at low temperature also generates the secondary alcohol 21.

Scheme 6

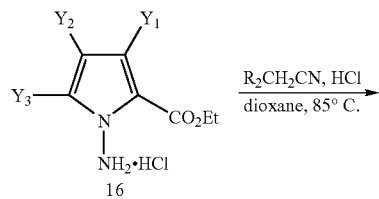

-continued

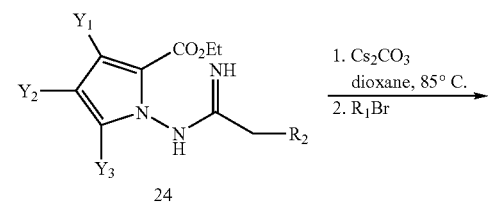
24

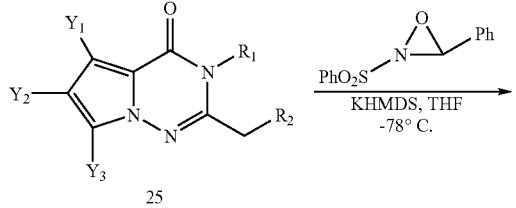
25

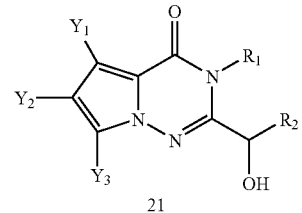
21

Elaboration of the pyrrolotriazinone ring system to the final products can be accomplished following the reaction sequences described in Scheme 7. Reductive amination of compound 10 with a substituted aldehyde and sodium triacetoxyborohydride or treatment of the chloride 22 or the mesylate 23, with a substituted amine at elevated temperatures in NMP provides an intermediate 26. Acylation, sulfonylation, or reductive amination of compound 26 affords the target molecules 27–29, respectively. Compounds of the invention may also be prepared using alternative reagents or reaction sequences which will be obvious to one skilled in the art.

Scheme 7

22 or 23

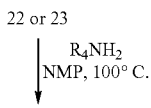

R₄NH₂
NMP, 100° C.

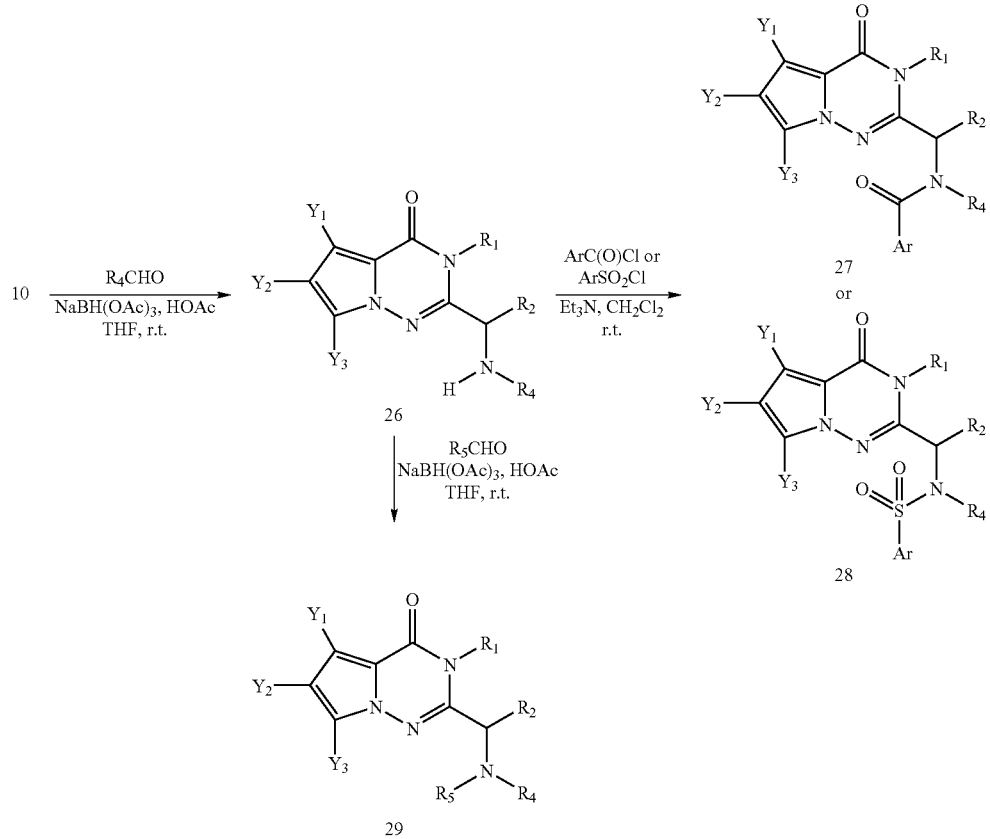

As discussed in the background section, Eg5 is a kinesin-like motor protein that facilitates spindle bipolarity during mitosis of the cell cycle. More specifically, the Eg5 protein acts to sort and bundle microtubules of the mitotic spindle during mitosis. Accordingly, Eg5 participates in cell cycle regulation through the spindle checkpoint during the M phase of the cycle. While not wishing to be bound by any theory, it is believed that the compounds of the instant invention act as Eg5 inhibitors. This is theorized because the compounds of the instant invention induce a monopolar astral array of microtubules (the monoastral phenotype) and it has been shown that when Eg5 activity is absent, the monoastral phenotype forms. Regardless of the mechanism of action, the compounds of the instant invention have been shown to cause disruption of the bipolar spindle, spindle checkpoint initiation, mitotic arrest, programmed cell death and tumor cell proliferation inhibition. Furthermore, the compounds of the invention induce a cell cycle arrest in mitosis that is not transient but rather which progresses into programmed cell death. The compounds also exhibit high potency, inducing mitotic arrest and apoptosis in human cells in vitro at concentrations in the low or sub $\mu M$ range. Additionally, in contrast to microtubule agents, the compounds do not disrupt the dynamic instability of microtubules. The instant invention may therefore more specifically target the mitotic spindle of proliferating cells, which may provide for different toxicity profiles than those of existing anti-cancer drugs.

The compounds according to the invention have pharmacological properties; in particular, the compounds of formula I induce mitotic arrest and are believed to be Eg5 inhibitors. The novel compounds of formula I are thus useful in the therapy of a variety of proliferative diseases (including but not limited to diseases associated with the Eg5 motor protein) such as cancer, autoimmune diseases, viral diseases, fungal diseases, neurodegenerative disorders and cardiovascular disease.

More specifically, the compounds of formula I are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Due to the key role of motor proteins in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I induce apoptosis. The apoptotic response is aberrant in a variety of human diseases. Compounds of formula I, as modulators of apoptosis, will be useful in the treatment of cancer (including but not limited to those types mentioned herein above), viral infections (including but not limited to herpevirus, poxyirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of formula I may modulate the level of cellular RNA and DNA synthesis. These agents would therefore be useful in the treatment of viral infections (including but not limited to HIV, human papilloma virus, herpesvirus, poxyirus, Epstein-Barr virus, Sindbis virus and adenovirus).

Compounds of formula I may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of formula I may also be useful in inhibiting tumor angiogenesis and metastasis.

The instant invention may also inhibit other motor proteins, for example, including but not limited to those human motor proteins that correspond to, Xklp2, MKLP1, CHO1, chromokinesins, Nod, Cenp-E, MCAK, members of the BimC family, and members of the Kar3 family. Additionally, compounds used in the methods of the instant invention may also act as inhibitors of other kinesin or kinesin-like proteins and thus be effective in the treatment of diseases associated with other kinesin or kinesin-like proteins.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones, either naturally occurring or synthetic; hormonal agents, such as tamoxifen; thymidilate synthase inhibitors, such as 5-fluorouracil, and UFT; and anti-metabolites, such as methotrexate, tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.™. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

Assays

The pharmacological properties of the compounds of this invention may be confirmed by a number of pharmacological assays. The exemplified pharmacological assays which follow have been carried out with the compounds according to the invention and their salts. The compounds of formula I exhibited antiproliferative activity.

Cell Culture

Cell lines are maintained in RPMI-1640 plus 10% fetal bovine serum.

72-Hour Proliferation Assay

Cells were plated at a density of 3,000–6,000 cells/well, depending upon the cell line used, in a 96-well plate. The cultures were grown overnight. Cells were then treated in triplicate with a seven concentration dose-response curve.

The maximum concentration of DMSO never exceeded 0.5%. Cells were exposed to compound for 72 hours. Proliferation was measured using XTT or MTS from Promega. The ovarian, breast, prostate, lung, leukemia, and colorectal human cancer cell lines used in this assay included but were not limited to, for example, A2780S, SKBR3, MDA-MB-231, PC3, LX-1, K562, HT-29, WiDr, HCT-15 and HCT116. The compounds of formula I exhibited activity in the 72-hour cell proliferation assay, inhibiting cell proliferation in one or more of the cell lines listed above with at an $IC_{50}$ less than or equal to about 10 μM.

Clonogenic Growth Assay

Colony growth inhibition was measured for A2780 ovarian carcinoma cells using a standard clonogenic assay. Briefly, 200 cells/well were seeded into 6-well tissue culture plates (Falcon, Franklin Lakes, N.J.) and allowed to attach for 18 hours. Assay medium consisted of RPMI-1640 plus 10% fetal bovine serum. Cells were then treated in duplicate with a six concentration dose-response curve. The maximum concentration of DMSO never exceeded 0.25%. Cells were exposed to compound for 4, 8 or 24 hours. Compound was then removed and the cells were washed with 2 volumes of PBS. The normal growth medium was then replaced. Colonies were fed with fresh media every third day. Colony number was scored on day 10–14 using a Optimax imaging station. The compound concentration required to inhibit 50% or 90% of colony formation ($IC_{50}$ or $IC_{90}$, respectively) was determined by non-linear regression analysis. The coefficient of variance (SD/mean, n=3)=30%. When exposed to cells for 24 hours, the compounds of formula I exhibited activity in the clonogenecity assay.

Cell Cycle Analysis

The cell cycle profile of cells treated with compounds of formula I was monitored by flow cytometry. Briefly, A2780 ovarian carcinoma cells were seeded at a density of $2 \times 10^5$ per well in standard 6 well culture plates and permitted to grow for 17 hours. Cells were then exposed to compounds of formula I at varying concentrations for 2 to 24 hours. Following exposure, cell populations were harvested, stained with propidium iodide to determine DNA content and also stained with the appropriate immunological reagent for protein biomarkers of mitosis and apoptosis, including, for example, anti-phospho-ThreonineProline, anti-M Phase Phosphoprotein 2 (MMP2), and anti-p85 PARP. The compounds of formula I exhibited activity in the cell cycle profile analysis assay, producing significant increases in mitotic and apoptotic fractions of the cell population.

Immunocytochemistry Assays

A2780 ovarian carcinoma cells or PTK2 kangaroo rat kidney epitheilal cells were plated at a density of 200 to 2000 cells per well in 4 chamber glass slides and allowed to attach overnight. Cells were then treated with compounds of formula I at concentrations of 100 nM to 50 μM for 4 to 30 hours, fixed and permeabilized for subsequent staining. Stain reagents included, for example, propidium iodide, DAPI, rhodamine phalloidin, anti-αtubulin, anti-βtubulin, anti-γtubulin, and the appropriate fluorescent-tagged secondary antibodies. Cells were imaged by fluorescent and confocal fluorescent microscropy. The compounds of formula I inhibited bipolar spindle formation and induced a monoastral array of microtubules.

Further subject matter of the invention also includes pharmaceuticals for use as described above including controlling cancer, inflammation and arthritis, which contain at least one compound of formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The following examples and preparations describe the manner and process of making and using the invention and are illustrative rather than limiting. It should be understood that there may be other embodiments which fall within the spirit and scope of the invention as defined by the claims appended hereto.

EXAMPLES

The invention will now be further described by the following working examples, which are preferred embodiments of the invention. All temperatures are in degrees Celsius (° C.) unless otherwise indicated. Preparative Reverse Phase (RP) HPLC purifications were carried out on C 18 reverse phase (RP) columns using water/methanol mixtures with 0.1% TFA as buffer solution. The following abbreviations are used for the commonly used reagents: BOC:t-butyl carbamate, FMOC:9H-fluorenylmethyl carbamate, NMM:N-methylmorpholine, NMP:N-methylpyrrolidinone, BOP reagent:benzotriazol-1-yloxytris(trimethylamino)phosphonium hexafluorophosphate, EDCI:1-(dimethylaminopropyl)-3-ethylcarbodiimide hydrochloride, rt: room temperature, PyBOP:bromotripyrrolidinophosphonium hexafluorophosphate, HOBt:hydroxybenzotriazole, $NaBH(OAc)_3$:sodium triacetoxyborohydride, HOAc:acetic acid, HCl:hydrochloric acid, TFA:trifluoroacetic acid, KHMDS:potassium bis(trimethylsilyl)amide, DMSO:dimethyl sulfoxide, MeCN:acetonitrile, MeOH:methanol, EtOAc:ethyl acetate, DMF:dimethyl formamide, THF:tetrahydrofuran. All LC/MS data were obtained using the following conditions: YMC S5 ODS 4.6×50 mm column, eluting with 10–90% aqueous methanol containing 0.1% TFA, using a gradient of 4 minutes with a 4 mL/min flow rate, monitoring at 220 nm. The $^1$H NMR spectra were obtained on a 400 or 500 MHz Bruker or Jeol instrument, respectively. The $^{13}$C NMR spectra were recorded at 100 or 125 MHz. Unless otherwise noted, all reagents were purchased from Aldrich.

Example 1

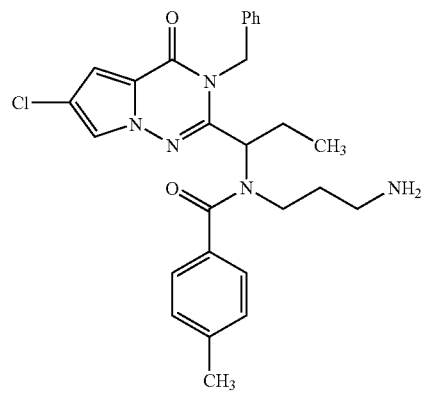

(±)-N-(3-Aminopropyl)-N-[1-(3-benzyl-6-chloro-4-oxo-3,4-dihydropyrrolo[2,1-f][1,2,4]triazine-2-yl)-propyl]-4-methylbenzamide, trifluoroacetic acid salt A) Methyl 1-amino-4-chloro-1H-pyrrole-2-carboxylate, hydrochloride salt A mixture of sodium hydride (60%, 1.51 g, 38 mmol) and methyl 4-chloro-1H-pyrrole-2-carboxylate (*Tetrahedron Letters*, 1979, 27, 2505–2508; 4.80 g, 30 mmol) in DMF (40 mL) at 0° C. was stirred for 20 min, then was added 2,4-dinitrophenolamine (*Tetrahedron Lett.* 1968, 16, 1909–1910 and *J. Heterocyclic Chem.* 1967, 413, 7.24 g, 36 mmol), and the reaction mixture was stirred at rt overnight. Water (100 mL) was added to the mixture, and the product was extracted with EtOAc (3×120 mL), the EtOAc solution was washed with 10% LiCl solution (2×120 mL), brine (120 mL), dried over $MgSO_4$ and concentrated in vacuo to give the crude product as a brown oil. This crude product was treated with 4 N HCl in dioxane (8 mL) in $Et_2O$ (60 mL), the precipitated solid was collected, washed with $Et_2O$ and dried to give the title compound (5.40 g, 85%): $^1H$ NMR (DMSO-$d_6$) δ 7.17 (d, 1H, J=2.2 Hz), 6.68 (d, 1H, J=2.2 Hz), 3.74 (s, 3H).

B) (±)-N'-benzyl-N-FMOC-α-aminobutyramide

A mixture of (±)-N'-benzyl-N-FMOC-α-aminobutyric acid (Tyger Scientific, 13.4 g, 41 mmol), EDCI (11.9 g, 62 mmol) and benzylamine (7 mL, 64 mmol) in methylene chloride (200 mL) was stirred at rt overnight. The reaction mixture was diluted with methylene chloride to 400 mL, washed with 10% citric acid (150 mL), water (100 mL) and brine (2×100 mL). The solid was filtered and dried to give the title compound as a white solid (10.9 g, 64%): $^1H$ NMR ($CDCl_3$) δ 7.75 (d, 2H, J=7.48 Hz), 7.58 (d, 2H, J=7.48 Hz), 7.40 (t, 2H, J=7.48 Hz), 7.30 (m, 7H), 6.20 (m, 1H), 5.30 (m, 1H), 4.41 (m, 4H), 4.20 (m, 1H), 1.92 (m, 1H), 1.70 (m, 1H), 0.94 (m, 3H); MS ($ESI^+$) 415.01 ($M^++H$).

C) (±)-N'-benzyl-N-FMOC-2-aminobutyrylthioamide

A suspension of (±)-N'-benzyl-N-FMOC-α-aminobutyramide (10.7 g, 26 mmol) and 2,4-bis(4-methoxyphenyl)-1,3-dithia-2,4-diphosphetane-2,4-disulfide (Lawesson's reagent, 12.5 g, 31 mmol) in methylene chloride (250 mL) at rt was treated with pyridine (12 mL, 148 mmol) and the mixture was heated at 80–82° C. for 10 h. The reaction mixture was washed with 10% citric acid (2×80 mL), aq. $NaHCO_3$ solution (80 mL) and brine (100 mL). The methylene chloride solution was separated, dried over $MgSO_4$, concentrated and the crude product was triturated with $Et_2O$/$CH_2Cl_2$ to obtain the title compound as a beige solid (11 g, 99%): $^1H$ NMR ($CDCl_3$) δ 8.25 (s, 1H), 7.75 (d, 2H, J=7.48 Hz), 7.58 (d, 2H, J=7.48 Hz), 7.40 (t, 2H, J=7.48 Hz), 7.30 (m, 7H), 5.66 (m, 1H), 4.84 (m, 1H), 4.77 (m, 1H), 4.27 (m, 2H), 4.17 (t, 1H, J=7.04 Hz), 3.82 (m 1H), 1.95 (m, 1H), 1.80 (m, 1H), 0.92 (m, 3H); MS ($ESI^+$) 431.07 ($M^++H$).

D) (±)-Methyl 1-{[N-benzyl-2-FMOC-aminobutyrimidoyl]amino}-4-chloro-1H-pyrrolo-2-carboxylate A mixture of (±)-N'-benzyl-N-FMOC-2-aminobutyrylthioamide (2.70 g, 6.3 mmol), EDCI (3.02 g, 15.8 mmol) and methyl 1-amino-4-chloro-1H-pyrrole-2-carboxylate (2.65 g, 12.6 mmol) in methylene chloride (50 mL) and DMF (3 mL) was stirred at rt overnight. The reaction mixture was diluted with methylene chloride to 160 mL, washed with 10% citric acid (2×50 mL) and brine (50 mL). The organic solution was separated, dried over $MgSO_4$ and concentrated to a dark oil. Flash column chromatography ($SiO_2$, EtOAc/Hexane 5:95 to 1:4) gave the title compound as a white solid (1.0 g, 40% based on the recovered starting (±)-N'-benzyl-N-FMOC-2-aminobutyrylthioamide) and the starting thioamide was also recovered (0.78 g). $^1H$ NMR ($CDCl_3$) δ 7.76 (d, 2H, J=7.48 Hz), 7.65 (t, 1H, J=7.68 Hz), 7.40 (t, 2H, J=7.46 Hz), 7.31 (m, 5H), 7.20 (m, 2H), 6.85 (d, 1H, J=1.76 Hz), 6.68 (d, 1H, J=1.76 Hz), 4.60 (m, 2H), 4.38 (m, 2H), 4.27 (m, 1H), 3.90 (m 1H), 3.70 (s, 3H), 1.95 (m, 2H), 1.00 (t, 3H, J=7.48 Hz); MS ($ESI^+$) 571.38 ($M^++H$).

E) (±)-2-(1-Aminopropyl)-3-benzyl-6-chloro-3-H-pyrrolo[2,1-f][1,2,4]triazine-4-one (±)-Methyl 1-{[N-benzyl-2-FMOC-aminobutyrimidoyl]amino}-4-chloro-1H-pyrrolo-2-carboxylate (1.0 g) was heated at 150° C. under Ar for 6 h. Purification by flash column chromatography ($SiO_2$, EtOAc/Hexane 1:9 to 1:0) gave the cyclized product (0.14 g, 25%): $^1H$ NMR ($CDCl_3$) δ 7.31 (m, 4H), 7.16 (d, 2H, J=7.04 Hz), 6.98 (d, 1H, J=1.76 Hz), 5.47 (d, 1H, J=16.26 Hz), 5.29 (d, 1H, J=16.26 Hz), 3.71 (m, 1H), 1.83 (m, 1H), 1.57 (m, 1H), 0.86 (t, 3H, J=7.04 Hz); $^{13}C$ NMR ($CDCl_3$) δ 154.3, 152.7, 136.3, 129.0, 127.8, 126.2, 118.3, 117.9, 115.6, 107.8, 53.6, 44.4, 30.1, 10.6; MS ($ESI^+$) 317.10 ($M^++H$).

F) (±)-N-(3-N-BOC-aminopropyl)-N-[1-(3-benzyl-6-chloro-4-oxo-3,4-dihydropyrrolo[2,1-f][1,2,4]triazine-2-yl)propylamine A solution of (±)-2-(1-aminopropyl)-3-benzyl-6-chloro-3-H-pyrrolo[2,1-f][1,2,4]triazine-4-one (0.13 g, 0.41 mmol), N-BOC-aminopropanal (*J. Med. Chem.* 1985, 28, 317–323, 0.16 g, 0.92 mmol) and HOAc (0.1 mL) in THF (3.0 mL) was stirred at rt for 20 min, then $NaBH(OAc)_3$ (0.16 g, 0.72 mmol) was added and the resulting mixture was stirred at rt for 2.5 h. Additional aldehyde (0.1 g, 0.58 mmol) and $NaBH(OAc)_3$ (0.16 g, 0.72 mmol) were added and the reaction mixture was stirred at rt overnight. The reaction mixture was diluted with EtOAc to 60 mL, washed with saturated $NaHCO_3$ solution (2×15 mL), dried over $MgSO_4$ and concentrated to an oil. Purification of the residue by flash column chromatography ($SiO_2$, EtOAc/Hexane 1:5 to 3:2) gave the title compound as a pale oil (0.18 g, 92%): $^{13}C$ NMR ($CDCl_3$) δ 156, 155, 152, 136, 129.0, 127.9, 126.4, 118.4, 117.9, 116, 107.9, 60, 59.7, 59, 53.6, 45.2, 44.4, 39.6, 33, 29.5, 28.4, 21.8, 14.2, 10.8; MS ($ESI^+$) 474.19 ($M^++H$).

G) (±)-N-(3-Aminopropyl)-N-[1-(3-benzyl-6-chloro-4-oxo-3,4-dihydropyrrolo[2,1-f][1,2,4]triazine-2-yl)-propyl]-4-methylbenzamide, trifluoroacetic acid salt To a solution of (±)-N-(3-N-BOC-aminopropyl)-N-[1-(3-benzyl-6-chloro-4-oxo-3,4-dihydropyrrolo[2,1-f][1,2,4]triazine-2-yl)propylamine (0.18 g, 0.38 mmol) and $Et_3N$ (0.09 mL, 0.65 mmol) in $CH_2Cl_2$ (4 mL) at rt was added p-toluoyl chloride (0.06 mL, 0.45 mmol) under $N_2$ and it was stirred at rt overnight. The reaction mixture was diluted with EtOAc to 60 mL, washed with saturated $NaHCO_3$ solution (15 mL), brine (20 mL), dried over $MgSO_4$ and concentrated to obtain the free base of the title compound as an oil. This oil was dissolved in $CH_2Cl_2$ (1 mL) and treated with of TFA (1 mL) for 30 min at rt. After concentration, the residue was purified by preparative HPLC ($C_{18}$ YMC-Pack ODS, 100×20 mm, with 0.1% TFA/MeOH/$H_2O$) to obtain the title compound (0.062 g, 27%): $^{13}C$ NMR ($CDCl_3$) δ 154.3, 152.7, 136.3, 129.0, 127.8, 126.2, 118.3, 117.9, 115.6, 107.8, 53.6, 44.4, 30.1, 10.6; MS ($ESI^+$) 492.17 ($M^++H$).

Example 2

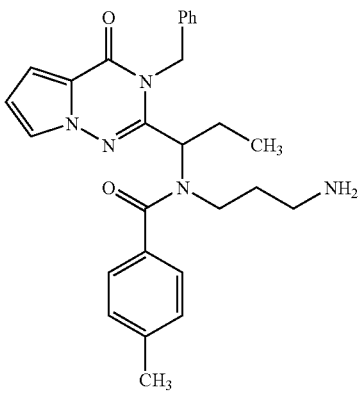

(±)-N-(3-Aminopropyl)-N-[1-(3-benzyl-4-oxo-3,4-dihydropyrrolo[2,1-f][1,2,4]-triazin-2-yl)-propyl]-4-methylbenzamide, trifluoroacetic acid salt A mixture (±)-N-(3-aminopropyl)-N-[1-(3-benzyl-6-chloro-4-oxo-3,4-dihydropyrrolo[2,1-f][1,2,4]triazine-2-yl)-propyl]-4-methylbenzamide, trifluoroacetic acid salt (Example 1, 20 mg, 0.033 mmol), PtO$_2$ (50 mg) and HOAc (0.1 mL) in methanol (2 mL) was stirred at rt under 1 atm of H$_2$ overnight. The catalyst was filtered off and the residue was purified by preparative HPLC (C$_{18}$ YMC-Pack ODS, 100×20 mm, with 0.1% TFA/MeOH/H$_2$O) to obtain the title compound (16 mg, 85%): $^{13}$C NMR (CDCl$_3$)δ 154.6, 145.6, 141.8, 135.2, 131.5, 129.9, 128.5, 127.7, 127.0, 125.7, 121.5, 117.9, 112.0, 110.1, 59.5, 43.6, 38.9, 37.2, 27.6, 26.2, 21.4, 10.0; MS (ESI$^+$) 458.28 (M$^+$+H).

outlined for Example 12 A–F, except substituting p-toluoyl chloride for 4-chlorobenzoyl chloride in F) and Pd(OH)$_2$ (20 wt. % Pd on carbon, 66 mg) in ethanol (6 mL) was stirred at 50° C., under 60 psi of hydrogen, for 22 h. The catalyst was filtered off and the residue was purified by preparative HPLC (YMC S10 ODS, 30×500 mm, 30 minute gradient from 62–90% aqueous methanol with 0.1% TFA). The appropriate fractions were combined, neutralized with saturated aqueous sodium bicarbonate, and then concentrated in vacuo to remove the methanol. The mixture was extracted with ethyl acetate (3×10 mL). The combined organic layers were washed once each with water and brine, dried over anhydrous magnesium sulfate, and concentrated in vacuo to yield the title compound (63 mg, 65%): $^1$H NMR (CDCl$_3$) δ 10.52 (s, 1H), 7.37–7.35 (m, 3H), 7.27–7.23 (m, 2H), 7.07 (m, 1H), 6.54 (m, 1H), 4.60 (m, 1H), 4.21 (m, 1H), 3.40 (m, 2H), 2.89 (m, 2H), 2.40 (s, 3H), 2.29 (m, 2H), 1.64 (m, 2H), 1.37 (s, 9H), 1.08 (t, 3H, J=7.15 Hz); MS (ESI$^+$) 468.21 (M$^+$+H).

B) (±)-N-(3-Aminopropyl)-4-methyl-N-[1-(4-oxo-3,4-dihydropyrrolo[2,1-f][1,2,4]triazin-2-yl)-propyl]-benzamide, trifluoroacetic acid salt To a solution of (±)-(3-{(4-methylbenzoyl)-[1-(4-oxo-3,4-dihydropyrrolo[2,1-f][1,2,4]triazin-2-yl)-propyl]-amino}-propyl)-carbamic acid tert-butyl ester (14 mg, 0.03 mmol) in dichloromethane (2 mL) was added TFA (0.5 mL). The mixture was stirred at ambient temperature for 1 h before being concentrated in vacuo. The resulting residue was dissolved in water and then lyophilized to yield the title compound (16.3 mg, 100%): $^1$H NMR (DMSO-d$_6$, 100° C.) δ 7.53 (s, 1H), 7.34–7.19 (m, 4H), 6.88 (m, 1H), 6.55 (m, 1H), 4.76 (m, 1H), 3.47 (m, 3H), 2.75 (m, 2H), 2.49 (s, 3H), 2.35 (s, 3H), 2.18–1.85 (m, 4H), 0.99–0.81 (m, 3H); HRMS (ESI$^+$) 368.2087 (M$^+$+H) calc, 368.2087 (M$^+$+H). found.

Example 3

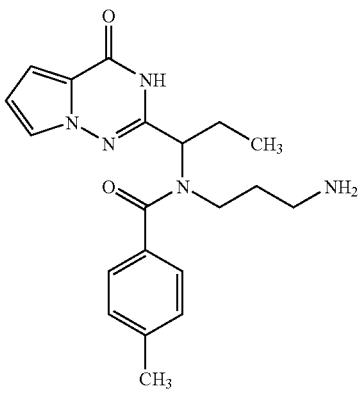

(±)-N-(3-Aminopropyl)-4-methyl-N-[1-(4-oxo-3,4-dihydropyrrolo[2,1-f][1,2,4]triazin-2-yl)-propyl]-benzamide, trifluoroacetic acid salt A) (±)-(3-{(4-Methylbenzoyl)-[1-(4-oxo-3,4-dihydropyrrolo[2,1-f][1,2,4]triazin -2-yl)-propyl]-amino}-propyl)-carbamic acid tert-butyl ester A mixture of {3-[[1-(3-benzyl-4-oxo-3,4-dihydropyrrolo[2,1-f][1,2,4]triazin-2-yl)-propyl]-(4-methylbenzoyl)-amino]-propyl}-carbamic acid tert-butyl ester (115 mg, 0.21 mmol, prepared using an identical synthetic sequence to that Example 4

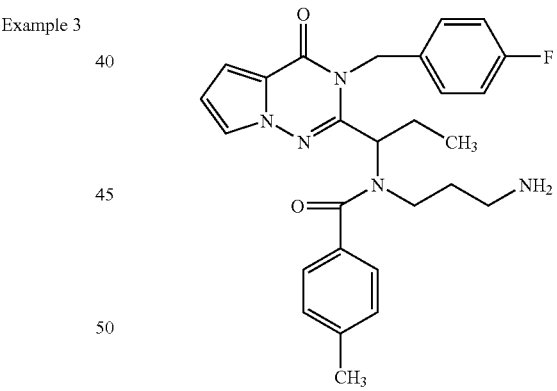

(±)-N-(3-Aminopropyl)-N-{1-[3-(4-fluorobenzyl)-4-oxo-3,4-dihydropyrrolo[2,1-f][1,2,4]triazin-2-yl]-propyl}-4-methylbenzamide, trifluoroacetic acid salt A) (±)-{3-[{1-[3-(4-Fluorobenzyl)-4-oxo-3,4-dihydropyrrolo[2,1-f][1,2,4]triazin-2-yl]-propyl}-(4-methylbenzoyl)-amino]-propyl}-carbamic acid tert-butyl ester A mixture of (±)-(3-{(4-methylbenzoyl)-[1-(4-oxo-3,4-dihydropyrrolo[2,1-f][1,2,4] triazin-2-yl)-propyl]-amino}-propyl)-carbamic acid tert-butyl ester (Example 3 A, 38 mg, 0.08 mmol) and cesium carbonate (40 mg, 0.12 mmol) in dioxane (1 mL) was stirred at 40° C., under Ar, for 45 min.

To the mixture was added 4-fluorobenzyl bromide (22 mg, 0.12 mmol) and the reaction mixture was stirred at 40° C. for 24 h before being diluted with ethyl acetate. The ethyl acetate layer was washed twice with water and once with brine, before being dried over anhydrous magnesium sulfate and concentrated in vacuo. The crude product was purified by preparative HPLC (YMC S10 ODS, 30×500 mm, 30 minute gradient from 74–90% aqueous methanol with 0.1% TFA). The appropriate fractions were combined, neutralized with saturated aqueous sodium bicarbonate, and then concentrated in vacuo to remove methanol. The mixture was extracted with ethyl acetate (3×10 mL). The combined organic layers were washed once each with water and brine, dried over anhydrous magnesium sulfate, and concentrated in vacuo to yield the title compound (7 mg, 15%): $^1$H NMR (CDCl$_3$) δ 7.44–6.99 (m, 10H), 6.61 (m, 1H), 5.91 (m, 1H), 5.88 (m, 1H), 4.83 (m, 1H), 3.86 (m, 1H), 3.33 (m, 2H), 2.71 (m, 2H), 2.39 (s, 3H), 2.05 (m, 1H), 1.85 (m, 1H), 1.62 (m, 2H), 1.39 (s, 9H), 0.71 (m, 3H); MS (ESI$^+$), 576.17 (M$^+$+H).

B) (±)-N-(3-Aminopropyl)-N-{1-[3-(4-fluorobenzyl)-4-oxo-3,4-dihydropyrrolo [2,1-f ][1,2,4]triazin-2-yl]-propyl}-4-methylbenzamide, trifluoroacetic acid salt To a solution of (±)-{3-[{1-[3-(4-fluorobenzyl)-4-oxo-3,4-dihydropyrrolo[2,1-f][1,2,4]triazin-2-yl]-propyl}-(4-methylbenzoyl)-amino]-propyl}-carbamic acid tert-butyl ester (7 mg, 0.01 mmol) in dichloromethane (1 mL) was added TFA (0.25 mL). The mixture was stirred at ambient temperature for 1 h before being concentrated in vacuo. The resulting residue was dissolved in water then lyophilized to yield the title compound (8 mg, 100%): $^1$H NMR (DMSO-d$_6$, 100° C.) δ 7.57 (m, 1H), 7.41 (m, 2H), 7.20–7.18 (m, 5H), 7.06–6.96 (m, 5H), 6.61 (m, 1H), 5.57 (m, 1H), 3.32 (m, 3H), 2.33 (s, 3H), 2.10 (m, 1H), 1.83 (m, 1H), 1.62 (m, 1H), 1.48 (m, 1H), 1.22 (s, 3H), 0.68 (t, 3H, J=7.15 Hz); HRMS (ESI$^+$) 476.2462 (M$^+$+H) calc, 476.2458 (M$^+$+H). found.

Example 5

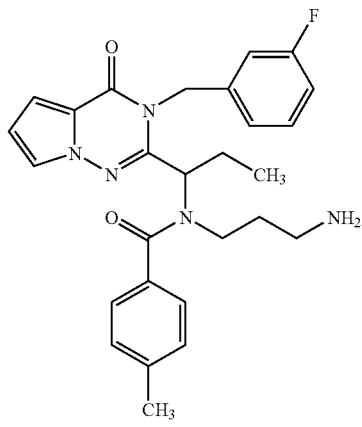

(±)-N-(3-Aminopropyl)-N-{1-[3-(3-fluorobenzyl)-4-oxo-3,4-dihydropyrrolo [2,1-f][1,2,4]triazin-2-yl]-propyl}-4-methylbenzamide, trifluoroacetic acid salt A) (±)-{3-[{1-[3-(3-Fluorobenzyl)-4-oxo-3,4-dihydropyrrolo[2,1-f ][1,2,4]triazin-2-yl]-propyl}-(4-methylbenzoyl)-amino]-propyl}-carbamic acid tert-butyl ester (±)-(3-{(4-Methylbenzoyl)-[1-(4-oxo-3,4-dihydropyrrolo [2,1-f][1,2,4] triazin-2-yl)-propyl]amino}propyl)carbamic acid tert-butyl ester (Example 3 A, 42 mg, 0.09 mmol) was converted to the title compound (7 mg, 13%) in a manner similar to the preparation of (±)-{3-[{1-[3-(4-fluorobenzyl)-4-oxo-3,4-dihydropyrrolo[2,1-f][1,2,4]triazin-2-yl]-propyl}-(4-methylbenzoyl)-amino]-propyl}-carbamic acid tert-butyl ester, except that 3-fluorobenzyl bromide (22 mg, 0.12 mmol) was used instead of 4-fluorobenzyl bromide: $^1$H NMR (CDCl$_3$) δ 7.45–6.96 (m, 10H), 6.62 (m, 1H), 5.95 (m, 1H), 5.86 (m, 1H), 4.90 (m, 1H), 3.86 (m, 1H), 3.33 (m, 2H), 2.71 (m, 2H), 2.39 (s, 3H), 2.05 (m, 1H), 1.85 (m, 1H), 1.60 (m, 1H), 1.40 (s, 9H), 1.05 (m, 1H), 0.72 (m, 3H).

B) (±)-N-(3-Aminopropyl)-N-{1-[3-(3-fluorobenzyl)-4-oxo-3,4-dihydropyrrolo [2,1-f][1,2,4]triazin-2-yl]-propyl}-4-methylbenzamide, trifluoroacetic acid salt (±)-{3-[{1-[3-(3-Fluorobenzyl)-4-oxo-3,4-dihydropyrrolo[2,1-f][1,2,4]triazin-2-yl]-propyl}-(4-methylbenzoyl)amino]propyl}carbamic acid tert-butyl ester (7 mg, 0.01 mmol) was converted to the title compound (6 mg, 83%) in a manner similar to the preparation of (±)-N-(3-aminopropyl)-N-{1-[3-(4-fluorobenzyl)-4-oxo-3,4-dihydro-pyrrolo [2,1-f][1,2,4]triazin-2-yl]-propyl}-4-methylbenzamide, trifluoroacetic acid salt: $^1$H NMR (DMSO-d$_6$, 100° C.) δ 7.54 (m, 1H), 7.40 (m, 2H), 7.25 (m, 1H), 7.18–7.13 (m, 4H), 6.99 (m, 1H), 6.93 (m, 1H), 6.76 (m, 1H), 6.58 (m, 1H), 5.54 (m, 1H), 3.46 (br m, 5H), 2.28 (s, 3H), 2.09 (m, 1H), 1.80 (m, 1H), 1.59 (m, 1H), 1.45 (m, 1H), 1.18 (m, 3H), 0.65 (t, 3H, J=7.15 Hz); HRMS (ESI$^+$) 476.2462 (M$^+$+H) calc, 476.2472 (M$^+$+H). found.

Example 6

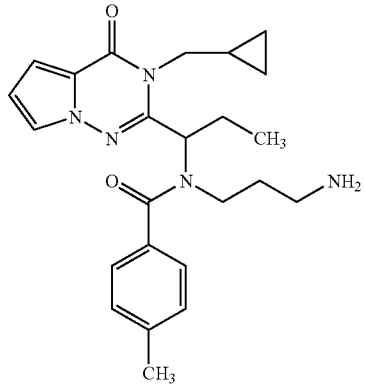

(±)-N-(3-Aminopropyl)-N-[1-(3-cyclopropylmethyl-4-oxo-3,4-dihydropyrrolo[2,1-f][1,2,4]triazin-2-yl)-propyl]-4-methylbenzamide, trifluoroacetic acid salt A) (±)-{3-[[1-(3-Cyclopropylmethyl-4-oxo-3,4-dihydropyrrolo[2,1-f ][1,2,4] triazin-2-yl)-propyl]-(4-methylbenzoyl)-amino]-propyl}-carbamic acid tert-butyl ester (±)-(3-{(4-Methylbenzoyl)-[1-(4-oxo-3,4-dihydropyrrolo [2,1-f][1,2,4] triazin-2-yl)-propyl]amino}propyl)carbamic acid tert-butyl ester (Example 3 A, 42 mg, 0.09 mmol) was converted to the title compound (8 mg, 17%) in a manner similar to the preparation of (±)-{3-[{1-[3-(4-fluorobenzyl)-4-oxo-3,4-dihydropyrrolo[2,1-f][1,2,4]triazin-2-yl]-propyl}-(4-methylbenzoyl)-amino]-propyl}-carbamic acid tert-butyl ester, except that bromo-methylcyclopropane (15 mg, 0.11 mmol) was used instead of 4-fluorobenzyl bromide: $^1$H NMR (CDCl$_3$) δ 7.40–7.22 (m, 5H), 7.04 (m, 1H), 6.57 (m, 1H), 6.00 (m, 1H), 4.41 (m, 1H), 3.81 (m, 1H), 3.65 (m, 1H), 3.40–3.05 (m, 3H), 2.69 (m, 2H), 2.38 (s, 3H), 2.27 (m, 1H), 1.97 (m, 1H), 1.61 (m, 2H), 1.39 (s, 9H), 1.27 (m, 2H), 0.80–1.10 (m, 3H), 0.59 (m, 2H).

B) (±)-N-(3-Aminopropyl)-N-[1-(3-cyclopropylmethyl-4-oxo-3,4-dihydropyrrolo [2,1-f][1,2,4]triazin-2-yl)-propyl]-4-methylbenzamide, trifluoroacetic acid salt (±)-{3-[[1-(3-Cyclopropylmethyl-4-oxo-3,4-dihydropyrrolo [2,1-f][1,2,4] triazin-2-yl)-propyl]-(4-methylbenzoyl) amino]propyl}carbamic acid tert-butyl ester (8 mg, 0.01 mmol) was converted to the title compound (6.6 mg, 100%) in a manner similar to the preparation of (±)-N-(3-aminopropyl)-N-{1-[3-(4-fluorobenzyl)-4-oxo-3,4-dihydropyrrolo [2,1-f][1,2,4]triazin-2-yl]-propyl}-4-methylbenzamide, trifluoroacetic acid salt: $^1$H NMR (DMSO-$d_6$, 100° C.) δ 7.48–7.10 (m, 8H), 6.85 (m, 1H), 6.53 (m, 1H), 3.46–2.67 (m, 3H), 2.28 (m, 4H), 1.93 (m, 1H), 1.59 (m, 1H), 1.45 (m, 1H), 1.18 (m, 4H), 0.98–0.90 (m, 4H), 0.62 (m, 1H), 0.34 (m, 2H), 0.19 (m, 1H); HRMS (ESI$^+$) 422.2556 (M$^+$+H) calc, 422.2564 (M$^+$+H). found.

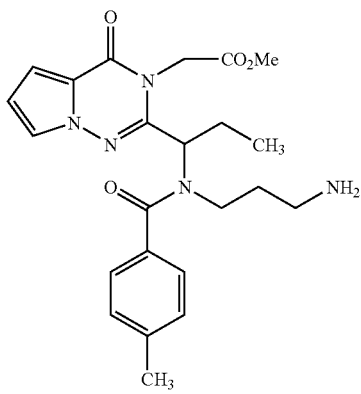

Example 7

(±)-((2-{1-[(3-Aminopropyl)-(4-methylbenzoyl)-amino]-propyl}-4-oxo-4H-pyrrolo[2,1-f][1,2,4]triazin-3-yl)-acetic acid methyl ester, trifluoroacetic acid salt A) (±)-(2-{1-[(3-tert-Butoxycarbonylaminopropyl)-(4-methylbenzoyl)-amino]-propyl}-4-oxo-4H-pyrrolo[2,1-f][1,2,4]triazin-3-yl)-acetic acid methyl ester (±)-(3-{(4-Methylbenzoyl)-[1-(4-oxo-3,4-dihydropyrrolo [2,1-f][1,2,4] triazin-2-yl)-propyl]amino}propyl)carbamic acid tert-butyl ester (Example 3 A, 100 mg, 0.21 mmol) was converted to the title compound (35 mg, 31%) in a manner similar to the preparation of (±)-{3-[{1-[3-(4-fluorobenzyl)-4-oxo-3,4-dihydropyrrolo[2,1-f][1,2,4]triazin-2-yl]-propyl}-(4-methylbenzoyl)-amino]-propyl}-carbamic acid tert-butyl ester, except that methyl bromoacetate (42 mg, 0.27 mmol) was used instead of 4-fluorobenzyl bromide: $^1$H NMR (CDCl$_3$) δ 7.43 (m, 1H), 7.26–7.21 (m, 4H), 7.07 (m, 1H), 6.58 (m, 1H), 5.84 (m, 1H), 5.10 (m, 1H), 4.78 (m, 1H), 3.91 (m, 1H), 3.78 (m, 3H), 3.71 (m, 1H), 3.31 (m, 2H), 2.74 (m, 2H), 2.40 (s, 3H), 2.21 (m, 1H), 2.05 (m, 1H), 1.52 (m, 1H), 1.39 (s, 9H), 1.04 (t, 3H, J=7.15 Hz); MS (ESI$^+$) 540.21 (M$^+$+H).

B) (±)-((2-{1-[(3-Aminopropyl)-(4-methylbenzoyl)-amino]-propyl}-4-oxo-4H-pyrrolo[2,1-f][1,2,4]triazin-3-yl)-acetic acid methyl ester, trifluoroacetic acid salt (±)-(2-{1-[(3-tert-Butoxycarbonylaminopropyl)-(4-methylbenzoyl)amino] propyl}-4-oxo-4H-pyrrolo[2,1-f][1,2,4] triazin-3-yl)acetic acid methyl ester (11 mg, 0.02 mmol) was converted to the title compound (9.2 mg, 82%) in a manner similar to the preparation of (±)-N-(3-aminopropyl)-N-{1-[3-(4-fluorobenzyl)-4-oxo-3,4-dihydropyrrolo [2,1-f][1,2,4] triazin-2-yl]-propyl}-4-methylbenzamide, trifluoroacetic acid salt: $^1$H NMR (DMSO-$d_6$, 100° C.) δ 7.60 (m, 1H), 7.52–7.14 (m, 7H), 6.97 (m, 1H), 6.64 (m, 1H), 4.92 (m, 1H), 4.55 (m, 1H), 3.68 (s, 3H), 3.40–3.25 (m, 3H), 2.45 (m, 2H), 2.36 (s, 3H), 2.26 (m, 1H), 2.00 (m, 1H), 1.68 (m, 1H), 1.53 (m, 1H), 0.96 (t, 3H, J=7.15 Hz); HRMS (ESI$^+$) 440.2298 (M$^+$+H) calc, 440.2295 (M$^+$+H). found.

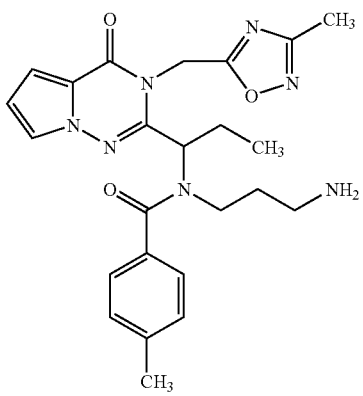

Example 8

(±)-N-(3-Aminopropyl)-4-methyl-N-{1-[3-(3-methyl-[1,2,4]oxadiazol-5-ylmethyl)-4-oxo-3,4-dihydro-pyrrolo[2,1-f][1,2,4]triazin-2-yl]-propyl}-benzamide, trifluoroacetic acid salt A) (±)-[3-((4-Methylbenzoyl)-{1-[3-(3-methyl-[1,2,4]oxadiazol-5-ylmethyl)-4-oxo-3,4-dihydropyrrolo[2,1-f][1,2,4] triazin-2-yl]propyl}-amino)-propyl]-carbamic acid tert-butyl ester To a mixture of (±)-(2-{1-[(3-tert-butoxycarbonylaminopropyl)-(4-methylbenzoyl) amino]propyl}-4-oxo-4H-pyrrolo[2,1-f][1,2,4]triazin-3-yl)acetic acid methyl ester (Example 7 A, 26 mg, 0.05 mmol) and N-hydroxyacetamidine (Tyger Scientific, 6 mg, 0.08 mmol) in DMF (1 mL), under Ar, was treated with sodium hydride (6.5 mg as 60% dispersion in mineral oil, 0.15 mmol) and stirred at ambient temperature overnight before being diluted with ethyl acetate. The organic layer was washed twice with water and once with brine, dried over anhydrous magnesium sulfate, and concentrated in vacuo. The crude product was purified by preparative HPLC (YMC S5 ODS, 20×250 mm, 30 minute gradient from 66–90% aqueous methanol with 0.1% TFA). The appropriate fractions were combined, neutralized with saturated aqueous sodium bicarbonate, and then concentrated in vacuo to remove methanol. The mixture was extracted with ethyl acetate (3×10 mL). The combined organic layers were washed once each with water and brine, dried over anhydrous magnesium sulfate, and concentrated in vacuo to yield the title compound (5 mg, 18%): $^1$H NMR (CDCl$_3$) δ 7.45 (m, 1H), 7.21–7.08 (m, 4H), 7.07 (m, 1H), 6.59 (m, 1H), 5.97 (m, 1H), 5.83 (m, 1H), 5.47 (m, 1H), 3.92

(m, 1H), 3.36 (m, 2H), 2.74 (m, 2H), 2.38 (s, 3H), 2.34 (s, 3H), 2.30–1.98 (m, 2H), 1.74–0.80 (m, 14H); MS (ESI⁺) 564.20 (M⁺+H).

B) (±)-N-(3-Aminopropyl)-4-methyl-N-{1-[3-(3-methyl-[1,2,4]oxadiazol-5-ylmethyl)-4-oxo-3,4-dihydro-pyrrolo[2,1-f][1,2,4]triazin-2-yl]-propyl}benzamide, trifluoroacetic acid salt (±)-[3-((4-Methylbenzoyl)-{1-[3-(3-methyl-[1,2,4]oxadiazol-5-ylmethyl)-4-oxo-3,4-dihydropyrrolo[2,1-f][1,2,4]triazin-2-yl]propyl} amino)propyl]carbamic acid tert-butyl ester (5 mg, 0.01 mmol) was converted to the title compound (6 mg, 100%) in a manner similar to the preparation of (±)-N-(3-aminopropyl)-N-{11-[3-(4-fluorobenzyl)-4-oxo-3,4-dihydropyrrolo [2,1-f][1,2,4]triazin-2-yl]-propyl}-4-methylbenzamide, trifluoroacetic acid salt: ¹H NMR (CD₃OD) δ 7.43 (m, 1H), 7.24–7.04 (m, 4H), 6.96 (m, 1H), 6.60 (m, 1H), 5.40 (m, 2H), 3.56–3.33 (m, 2H), 3.21 (m, 6H), 2.41–2.06 (m, 6H), 1.28–0.71 (m, 7H); HRMS (ESI) 464.2410 (M⁺+H) calc, 464.2425 (M⁺+H). found.

Example 9

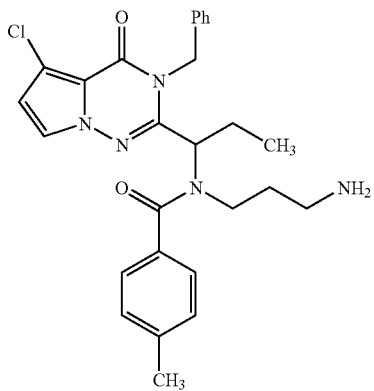

(±)-N-(3-Aminopropyl)-N-[1-(3-benzyl-5-chloro-4-oxo-3,4-dihydropyrrolo[2,1-f][1,2,4]-triazine-2-yl)-propyl]-4-methylbenzamide, trifluoroacetic acid salt A) Methyl 1-amino-3-chloro-1H-pyrrole-2-carboxylate, hydrochloride salt A mixture of sodium hydride (60%, 0.8 g, 20 mmol) and methyl 3-chloro-1H-pyrrole-2-carboxylate (*Tetrahedron*, 1999, 55, 4133–4152; 2.5 g, 15.7 mmol) in DMF (10 mL) at 0° C. was stirred for 25 min, then was added 2,4-dinitrophenolamine (*Tetrahedron Lett.* 1968, 16, 1909–1910 and *J. Heterocyclic Chem.* 1967, 413, 3.80 g, 19.1 mmol) and the reaction mixture was stirred at 0–5° C. for 2.5 h. The mixture was diluted with 10% aqueous LiCl solution and the product was extracted with EtOAc (3×100 mL). The EtOAc solution was washed with 10% LiCl solution (2×80 mL), brine (80 mL), dried over MgSO₄ and concentrated in vacuo to give the crude product as a brown oil. The crude product was treated with 4 N HCl in dioxane (2 mL) in Et₂O (60 mL). The precipitated solid was collected, washed with Et₂O and dried in vacuo to obtain the title compound (3.30 g, 99%): ¹H NMR (DMSO-d₆) δ 7.17 (d, 1H, J=2.2 Hz), 6.68 (d, 1H, J=2.2 Hz), 3.74 (s, 3H).

B) (±)-Methyl 1-{[N-benzyl-2-FMOC-aminobutyrimidoyl]amino}-3-chloro-1H-pyrrole-2-carboxylate A mixture of (±)-N′-benzyl-N-FMOC-2-aminobutyrylthioamide (Example 1 C, 4.0 g, 9.3 mmol), EDCI (5.60 g, 29.2 mmol) and methyl 1-amino-3-chloro-1H-pyrrole-2-carboxylate, hydrochloride salt (3.3 g, 15.6 mmol) in 1,2-dichloroethane (100 mL) was heated at 60° C. with stirring overnight. The reaction mixture was diluted with methylene chloride to 250 mL, washed with H₂O (3×100 mL) and brine (80 mL). The organic solution was separated, dried over MgSO₄ and concentrated. The residue was purified by flash column chromatography (SiO₂, EtOAc/Hexane 1:9 to 2:3) to give the title compound (0.31 g, 6.4%) and the recovered thioamide (0.41 g): ¹H NMR (CDCl₃) δ 7.82 (m, 4H), 7.59 (m, 1H), 7.30 (m, 8H), 6.78 (d, 1H, J=2.75 Hz), 6.11 (d, 1H, J=2.75 Hz), 4.35 (m, 2H), 4.20 (m, 3H), 3.99 (m, 1H), 3.47 (s, 3H), 1.50 (m, 2H), 0.60 (t, 3H, J=7.3 Hz); MS (ESI⁺) 571.38 (M⁺+H).

C) (±)-2-(1-Aminopropyl)-3-benzyl-5-chloro-3-H-pyrrolo [2,1-f][1,2,4]triazine-4-one (±)-Methyl 1-{[N-benzyl-2-FMOC-aminobutyrimidoyl] amino}-3-chloro-1H-pyrrolo-2-carboxylate (1.0 g) was heated at 130° C. under N₂ for 10 h, and the product was purified by preparative HPLC (C₁₈ YMC-Pack ODS, 100× 20 mm, with 0.1% TFA/MeOH/H₂O) to obtain the title compound (98 mg, 44%): ¹H NMR (CDCl₃) δ 7.25 (m, 4H), 7.13 (d, 2H, J=7.15 Hz), 7.03 (d, 1H, J=2.74 Hz), 6.30 (d, 1H, J=2.74 Hz), 5.29 (d, 1H, J=16.5 Hz), 4.96 (d, 1H, J=16.5 Hz), 4.24 (t, 1H, J=5.74 Hz), 1.55 (m, 2H), 0.63 (t, 3H, J=7.15 Hz); ¹³C NMR (CDCl₃) δ 153.4, 146.4, 135.2, 129.3, 128.5, 126.8, 120.2, 114.9, 113.4, 112.1, 51.3, 46.7, 26.6, 8.5; MS (ESI⁺) 317.10 (M⁺+H).

D) (±)-N-(3-N-BOC-Aminopropyl)-N-[1-(3-benzyl-5-chloro-4-oxo-3,4-dihydropyrrolo[2,1-f][1,2,4]triazine-2-yl) propylamine A mixture of (±)-2-(1-aminopropyl)-3-benzyl-5-chloro-3-H-pyrrolo[2,1-f][1,2,4]triazine-4-one (0.09 g, 0.21 mmol), N-BOC-aminopropanal (*J. Med. Chem.* 1985, 28, 317–323, 0.07 g, 0.40 mmol) and HOAc (0.05 mL) in THF (3.0 mL) was stirred at rt for 10 min, then the mixture was treated with NaBH(OAc)₃ (0.16 g, 0.72 mmol) and stirred at rt overnight. The reaction mixture was then diluted with EtOAc to 60 mL, washed with saturated NaHCO₃ solution (20 mL), dried over MgSO₄ and concentrated to an oil. Purification of the residue by flash column chromatography (SiO₂, EtOAc/Hexane 1:3) gave the title compound as a pale oil (0.043 g, 43%): MS (ESI⁺) 474.3 (M⁺+H).

E) (±)-N-(3-Aminopropyl)-N-[1-(3-benzyl-5-chloro-4-oxo-3,4-dihydropyrrolo[2,1-f][1,2,4]triazine-2-yl)-propyl]-4-methylbenzamide, trifluoroacetic acid salt To a solution of (±)-N-(3-N-BOC-aminopropyl)-N-[1-(3-benzyl-5-chloro-4-oxo-3,4-dihydropyrrolo[2,1-f][1,2,4]triazine-2-yl)propylamine (0.04 g, 0.08 mmol) and Et₃N (0.019 mL, 0.14 mmol) in CH₂Cl₂ (4 mL) at rt was added p-toluoyl chloride (0.0134 mL, 0.10 mmol) under N₂ and stirred at rt overnight. The reaction mixture was diluted with EtOAc to 60 mL, washed with 10% citric acid (20 mL), aq. NaHCO₃ solution (20 mL), dried over MgSO₄ and concentrated to an oil. The oil was dissolved in CH₂Cl₂ (0.5 mL) and treated with TFA (0.5 mL) for 30 min at rt. The mixture was concentrated and the residue was purified by preparative HPLC (C₁₈ YMC-Pack ODS, 100×20 mm, with 0.1% TFA/MeOH/H₂O) to obtain the title compound (0.026 g, 51%): ¹³C NMR (CDCl₃) δ 153.6, 146.8, 141.8, 135.5, 131.8, 129.9, 128.6, 127.8, 127.0, 125.8, 120.4, 113.4, 112.6, 60.0, 43.0, 38.8, 37.6, 27.6, 26.2, 21.4, 10.0; MS (ESI⁺) 492.2 (M⁺+H).

Example 10

N-(3-Aminopropyl)-N-[1-(3-benzyl-5-chloro-4-oxo-3,4-dihydropyrrolo[2,1-f][1,2,4]triazin-2-yl)-propyl]-4-methylbenzamide, hydrochloric acid salt (Enantiomer S)

Example 11

N-(3-Aminopropyl)-N-[1-(3-benzyl-5-chloro-4-oxo-3,4-dihydropyrrolo[2,1-f][1,2,4]triazin-2-yl)-propyl]-4-methylbenzamide, hydrochloric acid salt (Enantiomer R)

(±)-N-(3-Aminopropyl)-N-[1-(3-benzyl-5-chloro-4-oxo-3,4-dihydropyrrolo[2,1-f][1,2,4]triazin-2-yl)-propyl]-4-methylbenzamide (Example 9, 0.08 g, 0.15 mmol) was separated by chiral preparative HPLC (Chiralpak AD, 50×500 mm, 20μ column, at 50 mL per minute using 60:40 heptane/isopropyl alcohol with 0.2% diethylamine, λ=278 nm) into Enantiomer A and Enantiomer B.

Enantiomer S chiral analytical HPLC retention time=7.49 min (Chiralpak AD, 4.6×250 mm, 10μ column, at 1 mL per minute using 60:40 heptane/isopropyl alcohol with 0.2% diethylamine, λ=278 nm, chiral HPLC ee=98.2%). Enantiomer A was treated with 1 N aqueous HCl (0.2 mL) then lyophilized affording the HCl salt of Enantiomer A (28.7 mg).

Enantiomer R chiral analytical HPLC retention time=11.16 min (Chiralpak AD, 4.6×250 mm, 10μ column, at 1 mL per minute using 60:40 heptane/isopropyl alcohol with 0.2% diethylamine, λ=278 nm, chiral HPLC ee=96.8%). Enantiomer B was treated with 1 N aqueous HCl (0.2 mL) then lyophilized to afford the HCl salt of Enantiomer B (28.1 mg).

Total recovery of the two enantiomers was 56.8 mg (71%).

The absolute configuration of the compounds of examples 10 and 11 were determined by X-ray crystallography.

Example 12

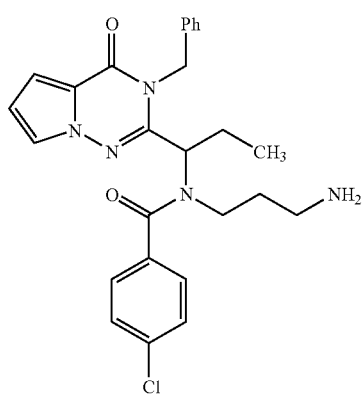

(±)-(3-Amino-propyl)-N-[1-(3-benzyl-4-oxo-3,4-dihydro-pyrrolo[2,1-f][1,2,4]triazin-2-yl)-propyl]-4-chloro-benzamide, hydrochloride salt A) 1-Amino-1H-pyrrole-2-carboxylic acid ethyl ester To a mixture of sodium hydride (60%, 4.31 g, 108 mmol) in DMF (150 mL) at 0° C. was added ethyl pyrrole-1H-2-carboxylate (Lancaster, 10 g, 71.9 mmol) in portions over 30 min. After stirring at 0° C. for 1 h, the light brown mixture was charged with a solution of 2,4-dinitrophenolamine (*Tetrahedron Lett.* 1968, 16, 1909–1910 and *J. Heterocyclic Chem.* 1967, 413, 17.2 g, 86.2 mmole) in DMF (50 mL) by an addition funnel over 30 min. The reaction was stirred at 0° C. for 2.5 h and was then quenched by the slow addition of saturated aqueous Na₂S₂O₃ (100 mL). The reaction mixture was extracted with EtOAc (7×100 mL) and the pooled organic extracts were washed with 10% LiCl solution (300 mL), dried over anhydrous Na₂SO₄, and concentrated in vacuo to give the crude product as a brown oil. Purification of the oil by flash column chromatography (SiO₂, EtOAc/Hexane 1:9 to 1:4) gave the title compound as a yellow oil (10.0 g, 90%): ¹H NMR (CDCl₃) δ 7.03 (t, 1H, J=2.36 Hz), 6.91 (dd, 1H, J=4.16, 2 Hz), 6.08 (d, 1H, J=2.6 Hz), 5.61 (brs, 2H), 4.36 (q, 2H, J=7.12 Hz), 1.43 (t, 3H, J=7.12 Hz); ¹³C NMR (CDCl₃) δ 162.2, 128.8, 120.8, 115.8, 105,9, 60.4, 14.8; MS (ESI⁺)155.05 (M⁺+H).

B) 1-Butyrimidoylamino-1H-pyrrole-2-carboxylic acid ethyl ester

To a solution of 1-amino-1H-pyrrole-2-carboxylic acid ethyl ester (10.8 g, 70.1 mmol) in 250 mL of dioxane in a sealed tube at room temperature was added butyronitrile (61 mL, 700 mmol) followed by 4 N HCl in dioxane (70 mL, 280 mmol). The tube was flushed with Ar, sealed, and heated at 75° C. for 14 h. After cooling to room temperature, the reaction mixture was concentrated in vacuo and then diluted with 240 mL of dioxane. Triethylamine (78 mL, 560 mmol) was added and the reaction was heated at 75° C. for 6 h. After cooling to room temperature, the reaction was concentrated in vacuo to give the crude product. Purification of the crude product by flash column chromatography (SiO₂, EtOAc/Hexane 1:1) gave the title compound as a light brown solid (11.6 g, 74%): ¹H NMR (CDCl₃) δ 6.80 (q, 1H, J=1.96 Hz), 6.59 (t, 1H, J=2.16 Hz), 6.03 (q, 1H, J=2.6 Hz), 4.54 (brs, 2H), 4.11 (q, 2H, J=7.12 Hz), 2.27 (t, 2H, J=7.96 Hz), 1.66 (hex, 2H, J=7.72 Hz), 1.19 (t, 3H, J=7.12 Hz), 0.95 (t, 3H, J=7.32 Hz); ¹³C NMR (CDCl₃) δ 166.7, 160.2, 124.8, 119.8, 116.0, 107.2, 60.0, 35.6, 20.6, 14.9, 14.1; MS (ESI⁺) 224.10 (M⁺+H).

C) 3-Benzyl-2-propyl-3H-pyrrolo[2,1-f][1,2,4]triazin-4-one

To a solution of 1-butyrimidoylamino-1H-pyrrole-2-carboxylic acid ethyl ester (7.6 g, 34 mmol) in dioxane (70 mL) at room temperature was added cesium carbonate (21.7 g, 66.7 mmol). The mixture was heated at 85° C. for 45 min and then benzyl bromide (4.2 mL, 35 mmol) was added. The reaction was stirred at 85° C. for 1 h. After cooling to room temperature, the reaction was filtered through a plug of silica gel and concentrated in vacuo. Purification of the crude product by flash column chromatography (SiO₂, EtOAc/Hexane 1:4) gave the title compound as a white solid (8.9 g, 99%): ¹H NMR (CDCl₃) δ 7.22 (m, 6H), 6.96 (m, 1H), 6.43 (m, 1H), 5.17 (s, 2H), 2.47 (q, 2H, J=7.44 Hz), 1.63 (m, 2H), 0.88 (t, 3H, J=7.4 Hz); ¹³C NMR (CDCl₃) δ 155.7, 149.7, 136.9, 129.3, 128.0, 126.8, 121.0, 118.4, 110.9, 108.8, 45.2, 34.6, 20.5, 14.1; MS (ESI⁺) 268.12 (M⁺+H).

D) (±)-3-Benzyl-2-(1-hydroxy-propyl)-3H-pyrrolo[2,1-f][1,2,4]triazin-4-one

To a solution of 3-benzyl-2-propyl-3H-pyrrolo[2,1-f][1,2,4]triazin-4-one (2.0 g, 7.48 mmol) in THF (45 mL) at −78° C. was added KHMDS (0.5 M in toluene, 17.2 mL, 8.6 mmol) dropwise. After stirring at −78° C. for 10 min, the orange solution was charged with a solution of racemic 2-benzenesulfonyl-3-phenyloxaziridine (2.15 g, 8.23 mmol) in THF (5 mL). The pale yellow solution was stirred at −78° C. for 25 min and was then quenched with 50 mL of saturated NaHCO₃ solution. The mixture was extracted with EtOAc (3×50 mL) and the pooled organic extracts were dried over anhydrous MgSO₄ and concentrated in vacuo. Purification of the crude product by flash column chromatography (SiO₂, EtOAc/Hexane 1:4) gave the title compound as a colorless viscous oil which solidified upon standing (1.40 g, 66%): $^1$H NMR (CDCl₃) δ 7.25 (m, 5H), 7.12 (t, 1H, J=1.4 Hz), 7.01 (m, 1H), 6.49 (m, 1H), 5.34 (d, 1H, J=16.1 Hz), 5.18 (d, 1H, J=16.2 Hz), 4.45 (m, 1H), 2.55 (brs, 1H), 1.78 (m, 1H), 1.63 (m, 1H), 0.88 (t, 3H, J=7.36 Hz); $^{13}$C NMR (CDCl₃) δ 155.4, 150.7, 136.7, 129.4, 128.2, 126.7, 121.4, 118.5, 111.5, 109.6, 71.0, 44.8, 29.8, 10.3; MS (ESI⁺) 284.17 (M⁺+H).

E) (±)-{3-[1-(3-Benzyl-4-oxo-3,4-dihydro-pyrrolo[2,1-f][1,2,4]triazin-2-yl)-propylamino]-propyl}-carbamic acid tert-butyl ester To a solution of (±)-3-benzyl-2-(1-hydroxy-propyl)-3H-pyrrolo[2,1-f][1,2,4]triazin-4-one (0.70 g, 2.47 mmol) in methylene chloride (20 mL) at 0° C. was added triethylamine (517 μL, 3.71 mmol) followed by methanesulfonyl chloride (290 μL, 3.71 mmol). The reaction was stirred at room temperature for 45 min and was then diluted methylene chloride (10 mL) and water (10 mL). The layers were separated and the aqueous layer was extracted with methylene chloride (10 mL). The combined organic extracts were washed with brine (10 mL), dried over anhydrous MgSO₄, and concentrated in vacuo. The crude mesylate was treated with N-BOC-1,3-diaminopropane (Fluka, 1.29 g, 7.41 mmol) and NMP (20 mL) at 75° C. for 14 h. After cooling to room temperature, the reaction was diluted with saturated NaHCO₃ solution (30 mL) and EtOAc (30 mL). The layers were separated and the aqueous layer was extracted with EtOAc (2×30 mL). The combined organic extracts were washed with 10% LiCl solution (30 mL), dried over anhydrous MgSO₄, and concentrated in vacuo. Purification of the crude product by flash column chromatography (SiO₂, EtOAc/Hexane 1:1) gave the title compound as a colorless viscous oil (610 mg, 61%): $^1$H NMR (CDCl₃) δ 7.25 (m, 6H), 7.01 (m, 1H), 6.47 (m, 1H), 5.66 (d, 1H, J=16.2 Hz), 5.04 (brs, 1H), 4.85 (d, 1H, J=16.1 Hz), 3.48 (m, 1H), 2.91 (m, 2H), 2.42 (m, 1H), 1.96 (m, 1H), 1.64 (m, 2H), 1.34 (s, 9H), 1.28 (m, 2H), 0.86 (t, 3H, J=7.28 Hz); $^{13}$C NMR (CDCl₃) δ 156.3, 155.7, 151.6, 137.1, 129.4, 128.1, 126.8, 121.3, 118.4, 111.2, 109.2, 79.3, 59.9, 45.8, 44.5, 39.7, 29.8, 28.8, 28.6, 11.2; MS (ESI⁺) 440.29 (M⁺+H).

F) (±)-{3-[1-(3-Benzyl-4-oxo-3,4-dihydro-pyrrolo[2,1-f][1,2,4]triazin-2-yl)-propyl]-(4-chloro-benzoyl)-amino]-propyl}-carbamic acid tert-butyl ester To a solution of (±)-{3-[1-(3-benzyl-4-oxo-3,4-dihydro-pyrrolo[2,1-f][1,2,4]triazin-2-yl)-propylamino]-propyl}-carbamic acid tert-butyl ester (610 mg, 1.39 mmole) in methylene chloride (10 mL) at 0° C. was added triethylamine (290 μL, 2.08 mmol) followed by 4-chlorobenzoyl chloride (265 mL, 2.08 mmol). After stirring at 0° C. for 1.5 h, the reaction was quenched with 10 mL of saturated NaHCO₃ solution and extracted with EtOAc (3×20 mL). The pooled organic extracts were dried over anhydrous MgSO₄ and concentrated in vacuo. Purification of the crude product by flash column chromatography (SiO₂, EtOAc/Hexane 4:1) gave the title compound as a white foam (755 mg, 94%): $^1$H NMR (CDCl₃) δ 7.22 (m, 11H), 6.52 (m, 1H), 5.83 (m, 2H), 4.82 (d, 1H, J=16.0 Hz), 4.00 (m, 1H), 3.21 (m, 2H), 2.65 (m, 2H), 1.97 (m, 1H), 1.75 (m, 1H), 1.32 (s, 11H), 0.62 (t, 3H, J=6.84 Hz); $^{13}$C NMR (CDCl₃) δ 171.8, 156.1, 155.6, 146.9, 137.0, 136.1, 135.0, 129.3, 129.2, 128.0, 127.2, 121.5, 118.4, 111.8, 109.7, 79.3, 54.9, 44.6, 42.5, 38.0, 31.9, 38.7, 24.7, 10.8; MS (ESI⁺) 578.31 (M⁺+H).

G) (±)-(3-Amino-propyl)-N-[1-(3-benzyl-4-oxo-3,4-dihydro-pyrrolo[2,1-f][1,2,4]triazin-2-yl)-propyl]-4-chloro-benzamide, hydrochloride salt A solution of (±)-{3-[1-(3-benzyl-4-oxo-3,4-dihydro-pyrrolo[2,1-f][1,2,4]triazin-2-yl)-propyl]-(4-chloro-benzoyl)-amino]-propyl}-carbamic acid tert-butyl ester (1.09 g, 1.89 mmole) in 4 N HCl/dioxane (10 mL) was stirred at room temperature for 2 h. The reaction was concentrated in vacuo to give a white foam. The crude product was lyophilized with acetonitrile/water to give the title compound as a white powder (970 mg, 99%): MS (ESI⁺) 478.24 (M⁺+H).

Example 13

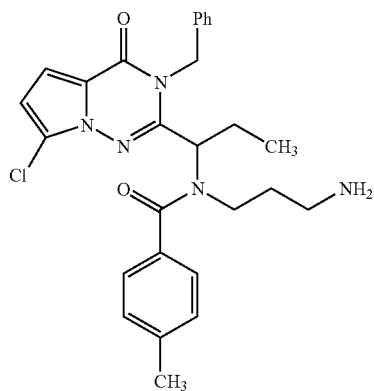

(±)-N-(3-Aminopropyl)-N-[1-(3-benzyl-7-chloro-4-oxo-3,4-dihydropyrrolo[2,1-f][1,2,4]-triazine-2-yl)-propyl]-4-methylbenzamide, hydrochloride salt A) Methyl 1-amino-5-chloro-1H-pyrrole-2-carboxylate, hydrochloride salt A mixture of sodium hydride (60%, 1.01 g, 25 mmol) and methyl 5-chloro-1H-pyrrole-2-carboxylate (*J. Chem. Soc.* 1965, 459–470, 2.96 g, 19.6 mmol) in DMF (40 mL) at 0° C. was stirred for 20 min, then was added 2,4-dinitrophenolamine (*Tetrahedron Lett.* 1968, 16, 1909–1910 and *J. Heterocyclic Chem.* 1967, 413, 3.90 g, 19.6 mmol) and the reaction mixture was stirred at 0° C. to rt overnight. The reaction mixture was diluted with saturated NaHCO₃ solution and the product was extracted with EtOAc (3×100 mL). The EtOAc solution was washed with saturated NaHCO₃ solution (4×60 mL), 10% LiCl solution (80 mL), brine (80 mL), dried over MgSO₄ and concentrated in vacuo to give the crude product as a brown oil. The crude product was treated with 4 N HCl in dioxane in Et₂O. The precipitated solid was collected, washed with Et₂O and dried in vacuo to obtain the title compound (1.91 g, 50%): $^1$H NMR (DMSO-d₆) δ 6.76 (d, 1H, J=4.4 Hz), 6.11 (d, 1H, J=4.4 Hz), 4.23 (q, 2H, J=6.02 Hz), 1.28 (t, 3H, J=6.02 Hz); $^{13}$C NMR (DMSO-d₆) δ 159.9, 122.9, 120.3, 114.0, 104.6, 59.8, 14.3.

B) (±)-Methyl 1-{[N-benzyl-2-FMOC-aminobutyrimidoyl]amino}-3-chloro-1H-pyrrolo-2-carboxylate A mixture of (±)-N'-benzyl-N-FMOC-2-aminobutyrylthioamide (Example 1 C, 3.06 g, 7.1 mmol), EDCI (2.80 g, 14.6 mmol) and ethyl 1-amino-5-chloro-1H-pyrrole-2-carboxylate (1.6 g, 7.1 mmol) in CH₂Cl₂ (30 mL) was stirred at rt overnight. The reaction mixture was diluted with methylene chloride to 120 mL, washed with aq. NaHCO₃ solution and brine and dried over MgSO₄ and concentrated. The oily residue was dissolved in CH₂Cl₂ (30 mL) and added to EDCI (4.0 g, 20.9 mmol). The mixture was stirred at rt for two days, diluted with methylene chloride to 160 mL, washed with aq. NaHCO$_3$ solution (60 mL), brine (80 mL) and dried over MgSO$_4$. Concentration and purification of the crude product by flash column chromatography (SiO$_2$, EtOAc/Hexane 8:92 to 1:4) gave the title compound (1.27 g, 30%): $^1$H NMR (CDCl$_3$) δ 7.76 (m, 2H), 7.59 (m, 11H), 7.40 (m, 2H), 7.26 (m, 8H), 6.92 (m, 1H), 6.11 (m, 1H), 4.35 (m, 3H), 4.23 (m, 3H), 1.28 (m, 3H), 1.05 (m, 2H); MS (ESI$^+$) 585.27 (M$^+$+H).

C) (±)-[1-(3-Benzyl-7-chloro-4-oxo-3,4-dihydro-pyrrolo[2,1-f][1,2,4]triazin-2-yl)-propyl]-carbamic acid 9H-fluoren-9-yl methyl ester (±)-Methyl 1-{[N-benzyl-2-FMOC-aminobutyrimidoyl]amino}-3-chloro-1H-pyrrolo-2-carboxylate (1.26 g) was heated at 149° C. in xylene (50 mL) under N$_2$ for 1 week and concentrated to dryness. Purification of the crude product by flash column chromatography (SiO$_2$, EtOAc/hexane 8:92 to 1:4) gave the title compound as light brown foam (0.81 g, 68%): $^1$H NMR (CDCl$_3$) δ 7.74 (m, 2H), 7.58 (d, 2H, J=7.7 Hz), 7.30 (m, 10H), 7.10 (d, 1H, J=4.4 Hz), 6.52 (d, 1H, J=4.4 Hz), 5.82 (d, 1H, J=15.7 Hz), 5.22 (d, 1H, J=9.9 Hz), 5.00 (d, 1H, J=15.7 Hz), 4.83 (m, 1H), 4.48 (m, 2H), 4.21 (m, 1H), 1.61 (m, 2H), 0.64 (t, 3H, J=7.4 Hz); MS (ESI$^+$) 539.29, 540.26, 541.28 (M$^+$+H).

D) (±)-2-(1-Aminopropyl)-3-benzyl-7-chloro-3-H-pyrrolo[2,1-f][1,2,4]triazine-4-one A solution of (±)-[1-(3-benzyl-7-chloro-4-oxo-3,4-dihydro-pyrrolo[2,1-f][1,2,4]triazin-2-yl)-propyl]-carbamic acid 9H-fluoren-9-ylmethyl ester (0.92 g, 1.7 mmol) and piperidine (0.5 mL) in DMF (10 mL) was allowed to stand at rt for 30 min. The reaction mixture was diluted with EtOAc to 100 mL, washed with 10% LiCl solution (2×50 mL) and dried over MgSO$_4$. Concentration and purification of the crude product by flash column chromatography (SiO$_2$, EtOAc/hexane 1:1) gave the title compound as colorless oil (0.462 g, 85.5%): $^1$H NMR (CDCl$_3$) δ 7.26 (m, 2H), 7.20 (m, 1H), 7.10 (d, 2H, J=7.15 Hz), 7.00 (d, 1H, J=4.4 Hz), 6.42 (d, 1H, J=4.4 Hz), 5.43 (d, 1H, J=16.5 Hz), 5.23 (d, 1H, J=16.5 Hz), 3.67 (t, 1H, J=6.62 Hz), 1.83 (m, 1H), 1.57 (m, 1H), 0.83 (t, 3H, J=7.15 Hz); $^{13}$C NMR (CDCl$_3$) δ 154.6, 136.3, 129.0, 127.8, 126.3, 117.7, 117.2, 110.0, 108.4, 53.6, 44.4, 29.7, 10.5; MS (ESI$^+$), 316.99, 319.31 (M$^+$+H).

E) (±)-N-{3-[1-(3-Benzyl-7-chloro-4-oxo-3,4-dihydro-pyrrolo[2,1-f][1,2,4]triazin-2-yl)-propylamino]-propyl}-carbamic acid tert-butyl ester A mixture of (±)-2-(1-aminopropyl)-3-benzyl-7-chloro-3-H-pyrrolo[2,1-f][1,2,4]triazine-4-one (0.45 g, 1.42 mmol), N-BOC-aminopropanal (*J. Med. Chem.*, 1985, 28, 317–323, 2.36 g, 13.6 mmol) and HOAc (0.2 mL) in MeOH (12 mL) was treated with NaBH(OAc)$_3$ (1.5 g, 6.7 mmol) and stirred at rt overnight. The reaction mixture was quenched with saturated NaHCO$_3$ solution, extracted with EtOAc (3×80 mL). The EtOAc solution was dried over MgSO$_4$ and concentrated to an oil. Purification of the crude product by flash column chromatography (SiO$_2$, EtOAc/Hexane 3.5:6.5 to 3:2) gave the title compound as a pale oil (0.52 g, 77.6%): MS (ESI$^+$) 474.24, 474.26 (M$^+$+H).

F) (±)-N-{3-[[1-(3-Benzyl-7-chloro-4-oxo-3,4-dihydro-pyrrolo[2,1-f][1,2,4]triazin-2-yl)-propyl]-(4-methyl-benzoyl)-amino]-propyl}-carbamic acid tert-butyl ester To a solution of (±)-N-{3-[1-(3-benzyl-7-chloro-4-oxo-3,4-dihydro-pyrrolo[2,1-f][1,2,4]triazin-2-yl)-propylamino]-propyl}-carbamic acid tert-butyl ester (0.51 g, 1.08 mmol) and Et$_3$N (0.25 mL, 1.79 mmol) in CH$_2$Cl$_2$ (10 mL) at rt was added p-toluoyl chloride (0.21 mL, 1.58 mmol) under N$_2$ and stirred at rt for 3 hr. The reaction mixture was diluted with CH$_2$Cl$_2$ to 100 mL, washed with aq. NaHCO$_3$ solution (30 mL), dried over MgSO$_4$. Concentration and purification of the crude product by flash column chromatography (SiO$_2$, EtOAc/hexane 1.5:8.5 to 1:3) gave the title compound as pale oil (0.43 g, 67%): $^1$H NMR (CDCl$_3$) δ 7.30 (m, 2H), 7.24 (m, 1H), 7.15 (m, 2H), 7.10 (d, 1H, J=4.4 Hz), 6.53 (d, 1H, J=4.4 Hz), 5.91 (m, 1H), 4.95 (m, 1H), 3.35 (m, 2H), 2.70 (m, 1H), 2.36 (s, 3H), 2.05 (m, 1H), 1.95 (m, 1H), 1.43 (m, 3H), 1.35 (s, 9H), 0.67 (m, 3H); MS (ESI$^+$) 592.15 (M$^+$+H).

G) (±)-N-(3-Amino-propyl)-N-[1-(3-benzyl-7-chloro-4-oxo-3,4-dihydro-pyrrolo[2,1-f][1,2,4]triazin-2-yl)-propyl]-4-methyl-benzamide, hydrochloride salt A mixture of {3-[[1-(3-benzyl-7-chloro-4-oxo-3,4-dihydro-pyrrolo[2,1-f][1,2,4]triazin-2-yl)-propyl]-(4-methyl-benzoyl)-amino]-propyl}-carbamic acid tert-butyl ester (0.42 g, 0.71 mmol) and 4 N HCl in dioxane (4.5 mL, 18 mmol) in dioxane (5 mL) stirred at rt for 6.5 h. After concentration the mixture was diluted with water, washed with Et$_2$O (50 mL) and lyophilized to obtain the title compound (0.342 g, 91%): $^{13}$C NMR (DMSO-d$_6$) δ 153.0, 128.6, 128.3, 126.9, 125.8, 125.5, 117.6, 115.3, 110.0, 108.3, 53.8, 44.2, 41.2, 36.2, 28.3, 23.4, 20.6, 10.1; MS (ESI$^+$) 492.16, 493.22 (M$^+$+H).

Example 14

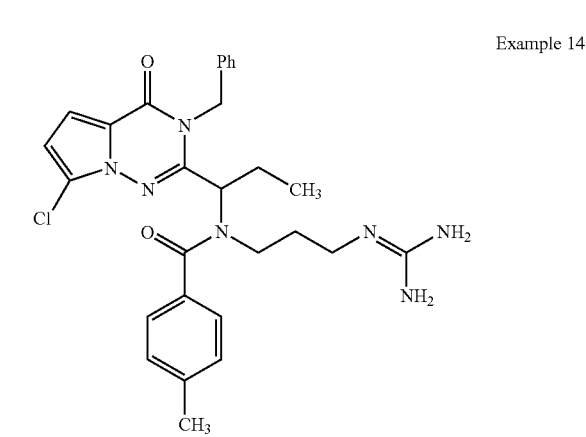

(±)-N-[1-(3-Benzyl-7-chloro-4-oxo-3,4-dihydro-pyrrolo[2,1-A][1,2,4]triazin-2-yl)-propyl]-N-(3-guanidino-propyl)-4-methyl-benzamide, trifluoroacetic acid salt A mixture of Example 13 (38 mg), bis-Boc-thiourea (48 mg, 0.088 mmol) and mercury chloride (65 mg) in DMF (1.2 mL) was allowed to stand at rt for 30 min. EtOAc (40 mL) and water (10 mL) were added to the mixture, the solid was filtered and organic layer was separated from the filtrate, dried over MgSO$_4$ and concentrated to obtain the crude product as a viscous material. This material was used directly for the next step. This material was mixed with CH$_2$Cl$_2$ (4.5 mL) and TFA (1.5 mL) and allowed to stand at rt for 1.5 h. The reaction mixture was concentrated in vacuo and the residue was purified by preparative HPLC to give the title compound (19 mg, 0.03 mM, 34% yield) as a beige solid: MS (ESI$^+$) 534, 536 (M$^+$+H).

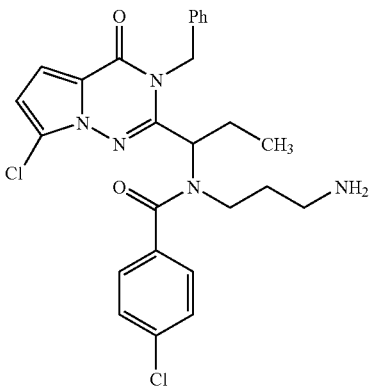

(±)-N-(3-Aminopropyl)-N-[1-(3-benzyl-7-chloro-4-oxo-3,4-dihydro-pyrrolo[2,1-f][1,2,4]triazin-2-yl)-propyl]-4-chlorobenzamide, trifluoroacetic acid salt To a solution of (±)-N-{3-[1-(3-benzyl-7-chloro-4-oxo-3,4-dihydro-pyrrolo[2,1-f][1,2,4]triazin-2-yl)-propylamino]-propyl}-carbamic acid tert-butyl ester (Example 13 E, 0.3 g, crude mixture) and Et$_3$N (0.3 mL) in CH$_2$Cl$_2$ (6 mL) at rt was added 4-chlorobenzoyl chloride (0.2 mL) under N$_2$ and stirred at rt overnight. The reaction mixture was diluted with EtOAc to 60 mL, washed with aq. NaHCO$_3$ solution and brine, dried over MgSO$_4$ and concentrated to oily residue. The residue was dissolved in CH$_2$Cl$_2$ (2 mL) and treated with TFA (1.5 mL) for 1 h. Concentration and purification of the crude product by preparative HPLC (C$_{18}$ YMC-Pack ODS, 100×20 mm, with 0.1% TFA/MeOH/H$_2$O) gave the title compound as light yellow foam (8.1 mg): $^{13}$C NMR (CDCl$_3$) δ 153.6, 146.8, 141.8, 135.5, 131.8, 129.9, 128.6, 127.8, 127.0, 125.8, 120.4, 113.4, 112.6, 60.0, 43.0, 38.8, 37.6, 27.6, 26.2, 21.4, 10.0; MS (ESI$^+$) 512.18, 514.17 (M$^+$+H).

Example 16

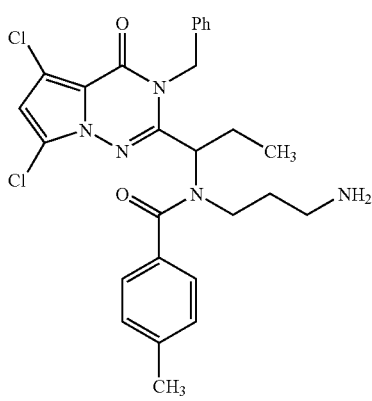

(±)-N-(3-Aminopropyl)-N-[1-(3-benzyl-5,7-dichloro-4-oxo-3,4-dihydropyrrolo[2,1-f][1,2,4]-triazine-2-yl)-propyl]-4-methylbenzamide, trifluoroacetic acid salt A) Ethyl 1-amino-3,5-chloro-1H-pyrrole-2-carboxylate, hydrochloride salt A mixture of sodium hydride (60%, 0.89 g, 22.3 mmol) and ethyl 3,5-dichloro-1H-pyrrole-2-carboxylate (*J. Chem. Soc.* 1965, 459–470, 2.9 g, 13.9 mmol) in DMF (40 mL) at 0° C. was stirred for 20 min, then was added 2, 4-dinitrophenolamine (*Tetrahedron Lett.* 1968, 16, 1909–1910 and *J. Heterocyclic Chem.* 1967, 413, 3.58 g, 18 mmol) and the reaction mixture was stirred at 0° C. to rt overnight. The reaction mixture was diluted with saturated NaHCO$_3$ solution and the product was extracted with EtOAc (3×100 mL). The EtOAc solution was washed with saturated NaHCO$_3$ solution and brine, dried over MgSO$_4$. Concentration and purification of the crude product by flash column chromatography (SiO$_2$, EtOAc/hexane 5:95 to 1:9) gave the title compound (1.89 g, 61%): MS (ESI$^+$) 222.07 (M$^+$+H).

B) (±)-Methyl 1-{[N-benzyl-2-FMOC-aminobutyrimidoyl]amino}-3,5-dichloro-1H-pyrrolo-2-carboxylate A mixture of (±)-N'-benzyl-N-FMOC-2-aminobutyrylthioamide (Example 1 C, 3.06 g, 7.1 mmole), EDCI (3.3 g, 7.66 mmol) and ethyl 1-amino-3,5-dichloro-1H-pyrrole-2-carboxylate (1.71 g, 7.67 mmol) in CH$_2$Cl$_2$ (30 mL) was stirred at rt for 10 days. Additional EDCI was added to the reaction mixture until the reaction was complete. The reaction mixture was diluted with EtOAc to 300 mL, washed with water, brine and dried over MgSO$_4$. Concentration and purification of the crude product by flash column chromatography (SiO$_2$, EtOAc/Hexane 1:9 to 1.5:8.5) gave the title compound (0.12 g, 2.5%): $^1$H NMR (CDCl$_3$) δ 7.73 (m, 2H), 7.59 (m, 1H), 7.28 (m, 8H), 6.25 (m, 1H), 4.62 (m, 1H), 4.50 (m, 1H), 4.36 (m, 2H), 4.23 (m, 3H), 2.00 (m, 1H), 1.86 (m, 1H), 1.34 (m, 2H), 1.26 (m, 2H), 1.04 (m, 3H); MS (ESI$^+$) 619.16, 621.14 (M$^+$+H).

C) (±)-2-(1-Aminopropyl)-3-benzyl-5,7-dichloro-3-H-pyrrolo[2,1-f][1,2,4]triazine-4-one (±)-Methyl 1-{[N-benzyl-2-FMOC-aminobutyrimidoyl]amino}-3,5-chloro-1H-pyrrolo-2-carboxylate (0.1 g) was heated at 145–150° C. in xylene (10 mL) under N$_2$ for 15 h and concentrated to dryness. Purification of the crude product by flash column chromatography (SiO$_2$, EtOAc/hexane/MeOH 1:9:0.005 to 1:4:0.005) gave the title compound as a light brown foam (40 mg, 60%): $^1$H NMR (CDCl$_3$) δ 7.24 (m, 3H), 7.13 (m, 2H), 6.38 (m, 1H), 5.43 (d, 1H, J=16.5 Hz), 4.90 (d, 1H, J=16.5 Hz), 4.34 (m 1H), 1.59 (m, 2H), 0.63 (m, 3H); MS (ESI$^+$) 351.10, 353.08 (M$^+$+H).

D) (±)-N-(3-N-BOC-Aminopropyl)-N-[1-(3-benzyl-5,7-dichloro-4-oxo-3,4dihydro-pyrrolo-[2,1-f][1,2,4]triazine-2-yl)propylamine A mixture of (±)-2-(1-aminopropyl)-3-benzyl-5,7-dichloro-3-H-pyrrolo[2,1-f][1,2,4]triazine-4-one (40 mg, 0.11 mmol), N-BOC-aminopropanal (*J. Med. Chem.* 1985, 28, 317–323, 76 mg, 0.44 mmol) and HOAc (0.1 mL) in MeOH (3.5 mL) was treated with NaBH(OAc)$_3$ (52 mg, 0.23 mmol) and stirred at rt for 2.5 h. The reaction mixture was quenched with saturated NaHCO$_3$ solution, and concentrated. Purification of the residue by preparative HPLC (C$_{18}$ YMC-Pack ODS, 100×20 mm, with 0.1% TFA/MeOH/H$_2$O) gave the title compound as a pale oil (46 mg, 80%): $^1$H NMR (CDCl$_3$) δ 7.28 (m, 3H), 7.22 (m, 1H), 7.12 (d, 2H, J=7.15 Hz), 6.45 (s, 1H), 5.43 (m, 1H), 4.90 (m, 1H), 2.93 (m 1H), 2.42 (m, 2H), 2.12 (m, 1H), 1.70 (m, 1H), 1.59 (m, 2H), 1.40 (m, 2H), 1.37 (m, 1H), 1.33 (s, 9H), 0.84 (t, 3H, J=7.15 Hz); MS (ESI$^+$) 351.10, 353.08 (M$^+$+H).

E) (±)-N-(3-Aminopropyl)-N-[1-(3-benzyl-5,7-dichloro-4-oxo-3,4-dihydropyrrolo[2,1-f][1,2,4]-triazine-2-yl)-propyl]-4-methylbenzamide, trifluoroacetic acid salt To a solution of (±)-N-(3-N-BOC-aminopropyl)-N-[1-(3-benzyl-7-chloro-4-oxo-3,4-dihydropyrrolo[2,1-f][1,2,4]triazine-2-yl)propylamine (40 mg, 0.079 mmol) and Et$_3$N (0.028 mL, 0.20 mmol) in CH$_2$Cl$_2$ (10 mL) at rt was added p-toluoyl chloride (0.017 mL, 0.13 mmol) under N$_2$ and stirred at rt overnight. The reaction mixture was diluted with CH$_2$Cl$_2$ to 20 mL, washed with aq. NaHCO$_3$ solution, dried over MgSO$_4$ and concentrated. The solid was dissolved in CH$_2$Cl$_2$ (0.5 mL), combined with TFA (0.5 mL) and stirred at rt for 30 min. Concentration and purification of the crude product by preparative HPLC [C]$_8$ YMC-Pack ODS, 100× 20 mm, with 0.1% TFA/MeOH/H$_2$O) gave the title compound (10 mg, 20%): $^1$H NMR (D$_2$O) δ 7.44 (m, 2H), 7.37 (m, 2H), 7.28 (m, 3H), 7.21 (m, 1H), 6.87 (d, 1H, J=7.15 Hz), 6.81 (d, 1H, J=8.8 Hz), 6.61 (d, 1H, J=7.15 Hz), 5.87 (m, 1H), 5.54 (m, 1H), 5.36 (m, 1H), 5.22 (m, 1H), 4.81 (m, 1H), 4.16 (m, 1H), 3.79 (m, 1H), 3.37 (m, 2H), 3.05 (m, 1H), 2.55 (m, 1H), 2.44 & 2.38 (2s, 3H), 2.30 (m, 1H), 2.05 (m, 2H), 1.80 (m, 1H), 1.50 (m, 1H), 0.92 & 0.67 (2 t, 3H, J=7.15 Hz); MS (ESI$^+$) 526.11, 528.12 (M$^+$+H).

Example 17

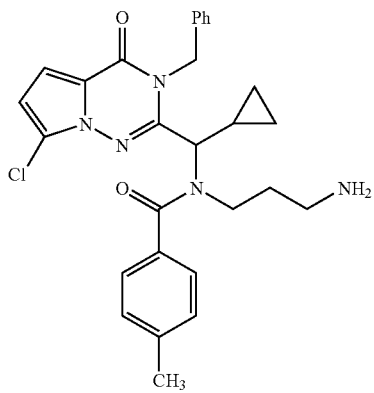

(±) —N-(3-Amino-propyl)-N-[(3-benzyl-7-chloro-4-oxo-3,4-dihydro-pyrrolo[2,1-f][1,2,4]triazin-2-yl)-cyclopropyl-methyl]-4-methyl-benzamide, hydrochloride salt A) 7-Chloro-2-methyl-3H-pyrrolo[2,1-f][1,2,4]triazin-4-one A mixture of methyl 1-amino-5-chloro-1H-pyrrole-2-carboxylate hydrochloride (Example 13 A, 2.2 g, 9.8 mmol) and 4 N HCl in dioxane (6.0 mL, 24 mmol) in acetonitrile (90 mL) was placed in a sealed tube and heated at 82° C. overnight. The reaction mixture was concentrated and diluted with fresh acetonitrile (100 mL) and triethylamine (5 mL). The reaction mixture was heated at 85° C. overnight, concentrated to dryness and diluted with EtOAc to 150 mL. The EtOAc solution was washed with 1 N HCl, followed by saturated NaHCO$_3$ solution and brine. The solution was dried over MgSO$_4$ and concentrated to a solid. The solid was triturated with Et$_2$O/hexane to give the title compound as a brown solid (1.15 g, 64%): $^1$H NMR (CDCl$_3$) δ 6.99 (d, 1H, J=4.38 Hz), 6.42 (d, 1H, J=4.38 Hz), 2.40 (s, 3H); MS (ESI$^+$) 183.98, 185.97 (M$^+$+H).

B) 3-Benzyl-7-chloro-2-methyl-3H-pyrrolo[2,1-f][1,2,4]triazin-4-one

To a stirred mixture of 7-chloro-2-methyl-3H-pyrrolo[2,1-f][1,2,4]triazin-4-one (1.10 g, 5.99 mmol) and Cs$_2$CO$_3$ (2.25 g, 6.9 mmol) in dioxane (20 mL) was added benzyl bromide (0.76 mL, 6.16 mmol) and heated at 95° C. under nitrogen for 3 h. The reaction mixture was cooled to rt, diluted with water and stirred for 1 h. The precipitated solid was collected and washed with water, dried in vaccum over P$_2$O$_5$ at 35° C. to give the title compound (1.41 g, 87%): $^1$H NMR (CDCl$_3$) δ 7.26 (m, 2H), 7.20 (m, 1H), 7.13 (m, 2H), 6.98 (d, 1H, J=4.4 Hz), 6.40 (d, 1H, J=4.4 Hz), 5.19 (s, 2H), 2.35 (s, 3H); 3C NMR (CDCl$_3$) δ 154.0, 148.0, 135.8, 129.0, 127.8, 126.5, 117.7, 116.5, 109.7, 108.2, 45.7, 20.1; MS (ESI$^+$) 274.04, 276.06 (M$^+$+H).

C) 3-Benzyl-7-chloro-2-(2-dimethylamino-vinyl)-3H-pyrrolo[2,1-f][1,2,4]triazin-4-one A mixture of 3-benzyl-7-chloro-2-methyl-3H-pyrrolo[2,1-f][1,2,4]triazin-4-one (1.60 g, 5.85 mmol), N,N-dimethylformamide dimethyl acetal (5.6 mL, 39.6 mmol) and MgSO$_4$ (5.0 g, 41.5 mmol) in DMF (20 mL) was sealed under nitrogen and heated at 145° C. overnight. The reaction mixture was cooled to 0° C., poured into ice water and stirred for 1 h. The solid was collected and washed with water, dried under vaccum over P$_2$O$_5$ to give the title compound (1.84 g, 96%): $^1$H NMR (CDCl$_3$) δ 7.50 (d, 1H, J=12.56 Hz), 7.30 (m, 2H), 7.24 (m, 4H), 6.96 (d, 1H, J=4.48 Hz), 6.38 (d, 1H, J=4.68 Hz), 5.27 (s, 2H), 2.83 (s, 3H).

D) 3-Benzyl-7-chloro-4-oxo-3,4-dihydro-pyrrolo[2,1-f][1,2,4]triazine-2-carbaldehyde A mixture of 3-benzyl-7-chloro-2-(2-dimethylamino-vinyl)-3H-pyrrolo[2,1-f][1,2,4]-triazin-4-one (1.84 g, 5.59 mmole) and sodium periodate (6.0 g, 28 mmol) in THF (70 mL) and pH 7 buffer was stirred at rt under nitrogen for 45 min. The reaction mixture was filtered through Celite®, the filtrate was extracted with EtOAc (2×80 mL). The EtOAc solution was dried over MgSO$_4$. Concentration and purification of the crude product by flash column chromatography (SiO$_2$, EtOAc/hexane 1.5:8.5 to 4:1) gave the title compound as a white solid (1.36 g, 84%): $^1$H NMR (CDCl$_3$) δ 9.48 (s, 1H), 7.20 (m, 5H), 7.10 (d, 1H, J=4.4 Hz), 6.60 (d, 1H, J=4.4 Hz), 5.68 (s, 2H); MS (ESI$^+$) 288.08 (M$^+$+H).

E) (±)-3-Benzyl-7-chloro-2-(cyclopropyl-hydroxy-methyl)-3H-pyrrolo[2,1-f][1,2,4] triazin-4-one To a solution of 3-benzyl-7-chloro-4-oxo-3,4-dihydro-pyrrolo[2,1-f][1,2,4]triazine-2-carbaldehyde (1.50 g, 5.21 mmol) in anhydrous CH$_2$Cl$_2$ (20 mL) at −76° C. under nitrogen was added dropwise cyclopropylmagnesium bromide (Boulder Scientific, 0.76 M, 20 mL, 15.2 mmol) in THF over 15 min. The reaction mixture was stirred at −70–50° C. for 1 h, quenched with aq. NH$_4$Cl and 1 N HCl, and extracted with EtOAc (3×70 mL). The EtOAc layers were dried and concentrated. Purification of the crude product by flash column chromatography (SiO$_2$, EtOAc/hexane 1.5:8.5 to 1:4) gave the title compound as a pale oil (1.2 g, 70%): $^1$H NMR (CDCl$_3$) δ 7.24 (m, 2H), 7.19 (m, 1H), 7.09 (m, 2H), 7.00 (d, 1H, J=4.4 Hz), 6.44 (d, 1H, J=4.4 Hz), 5.33 (q, 2H, AB), 4.10 (t, 1H, J=7.15 Hz), 2.62 (d, 1H, J=7.7 Hz), 1.40 (m, 1H), 0.51 (m, 2H), 0.32 (m, 1H), 0.14 (m, 1H); $^{13}$C NMR (CDCl$_3$) δ 154.3, 150.5, 136.1, 129.0, 127.8, 126.2, 117.8, 117.3, 110.2, 108.6, 72.76, 44.6, 15.5, 3.0; MS (ESI$^+$) 330.10 (M$^+$+H), 352.13, 354.13 (M$^+$+Na).

F) (±)-3-Benzyl-7-chloro-2-(chloro-cyclopropyl-methyl)-3H-pyrrolo[2,1-f][1,2,4]triazin-4-one To a stirred solution of 3-benzyl-7-chloro-2-(cyclopropyl-hydroxy-methyl)-3H-pyrrolo[2,1-f][1,2,4]triazin-4-one (1.40 g, 4.24 mmol) and pyridine (1.5 mL, 18.5 mmol) in CH$_2$Cl$_2$ (20 mL) was added thionyl chloride (2 M, 4.5 mL, 9.0 mmol) at 0° C. under nitrogen and stirred for 20 min. The reaction mixture was then stirred at rt overnight, poured into ice water, and extracted with CH$_2$Cl$_2$ (3×40 mL). The organic layers were washed with brine and dried over MgSO₄. Concentration and purification of the crude product by flash column chromatography (SiO₂, EtOAc/hexane 1:9) gave the title compound as a white solid (0.96 g, 65%): ¹H NMR (CDCl₃) δ 7.22 (m, 3H), 7.04 (m, 3H), 6.48 (d, 1H, J=4.4 Hz), 6.05 (d, 1H, J=16.5 Hz), 4.68 (d, 1H, J=16.5 Hz), 3.81 (d, 1H, J=10.45 Hz), 1.96 (m, 1H), 1.19 (m, 1H), 0.72 (m, 1H), 0.57 (m, 1H), 0.22 (m, 1H), −0.35 (m, 1H); ¹³C NMR (CDCl₃) δ 154.2, 148.2, 136.4, 129.2, 128.0, 125.8, 118.0, 117.6, 110.6, 109.0, 62.5, 44.1, 15.3, 7.22, 6.19; MS (ESI⁺) 348.02 (M⁺+H), 370.01 (M⁺+Na).

G) (±)-(3-{[(3-Benzyl-7-chloro-4-oxo-3,4-dihydro-pyrrolo[2,1-f][1,2,4]triazin-2-yl)-cyclopropyl-methyl]-amino}-propyl)-carbamic acid tert-butyl ester A solution of 3-benzyl-7-chloro-2-(cyclopropyl-hydroxymethyl)-3H-pyrrolo[2,1-f][1,2,4]triazin-4-one (0.32 g, 0.92 mmol) and N-BOC-1,3-diaminopropane (Fluka, 1.0 g, 5.7 mmol) in xylene (12 mL) was heated at 110° C. under nitrogen for 4 days. The solvent was removed under reduced pressure. Purification of the residue by flash column chromatography (SiO₂, EtOAc/hexane 1:3 to 3:2) gave the title compound as a light yellow oil (0.31 g, 62%): ¹H NMR (CDCl₃) δ 7.25 (m, 3H), 7.20 (m, 1H), 7.07 (d, 2H, J=7.15 Hz), 7.00 (d, 1H, J=4.95 Hz), 6.44 (d, 1H, J=4.95 Hz), 5.41 (m, 1H), 4.82 (m, 1H), 3.33 (m 1H), 3.03 (m, 2H), 2.40 (m, 2H), 1.52 (m, 2H), 1.35 (s, 9H), 1.30 (m, 2H), 1.19 (m, 2H), 0.52 (m, 1H), 0.35 (m, 1H), 0.13 (m, 1H); MS (ESI⁺) 486.17, 488.17 (M⁺+H).

H) (±)-{3-[[(3-Benzyl-7-chloro-4-oxo-3,4-dihydro-pyrrolo[2,1-f][1,2,4]triazin-2-yl)-cyclopropyl-methyl]-(4-methyl-benzoyl)-amino]-propyl}-carbamic acid tert-butyl ester To a solution of (±)-(3-{[(3-benzyl-7-chloro-4-oxo-3,4-dihydro-pyrrolo[2,1-f][1,2,4]-triazin-2-yl)-cyclopropyl-methyl]-amino}propyl)carbamic acid tert-butyl ester (0.30 g, 0.62 mmol) and Et₃N (0.13 mL, 0.93 mmol) in CH₂Cl₂ (10 mL) at rt was added p-toluoyl chloride (0.10 mL, 0.76 mmol) under N₂ and it was stirred at rt for 50 min. The reaction mixture was diluted with EtOAc, washed with saturated NaHCO₃ solution, and dried over MgSO₄. Concentration and purification of the residue by flash column chromatography (SiO₂, EtOAc/hexane 1:4) gave the title compound as an oil (0.244 g, 66%): ¹H NMR (CDCl₃) δ 7.22 (m, 2H), 7.13 (m, 3H), 7.04 (d, 1H, J=4.4 Hz), 6.48 (d, 1H, J=4.4 Hz), 5.90 (d, 1H, J=15.95 Hz), 5.12 (d, 1H, J=9.9 Hz), 4.83 (d, 1H, J=15.95 Hz), 4.03 (m, 1H), 3.54 (m, 1H), 3.45 (m, 1H), 2.74 (m, 2H), 2.31 (s, 3H), 1.66 (m, 2H), 1.29 (s, 9H), 1.19 (m, 3H), 0.80 (m, 1H), 0.42 (m, 1H), 0.32 (m, 2H); ¹³C NMR (CDCl₃) δ 172.9, 155.7, 154.6, 148.8, 139.8, 136.8, 133.2, 129.2, 128.8, 127.7, 126.8, 126.3, 117.7, 117.2, 110.3, 108.5, 57.9, 44.4, 42.7, 37.9, 30.9, 28.2, 21.4, 13.4, 5.24, 3.80; MS (ESI⁺) 626.16, 628.14 (M⁺+Na).

I) (±)-N-(3-Amino-propyl)-N-[(3-benzyl-7-chloro-4-oxo-3,4-dihydro-pyrrolo[2,1-f][1,2,4]triazin-2-yl)-cyclopropyl-methyl]-4-methyl-benzamide, hydrochloride salt A mixture of {3-[[(3-benzyl-7-chloro-4-oxo-3,4-dihydro-pyrrolo[2,1-f][1,2,4]triazin-2-yl)-cyclopropyl-methyl]-(4-methyl-benzoyl)-amino]-propyl}-carbamic acid tert-butyl ester (0.24 g, 0.39 mmol) and 4 N HCl in dioxane (10 mL, 16 mmol) in Et₂O (10 mL) was stirred at rt for two days. After concentration, the residue was diluted with water, washed with Et₂O twice and lyophilized to obtain the title compound (0.14 g, 66%): ¹³C NMR (D₂O) δ 174.1, 155.5, 148.4, 141.0, 136.3, 132.1, 129.7, 129.5, 128.9, 127.7, 126.1, 117.7, 117.2, 111.0, 108.8, 71.7, 70.9, 60.4, 43.4, 42.4, 36.9, 28.1, 20.7, 13.3; MS (ESI⁺) 504.17, 506.25 (M⁺+H).

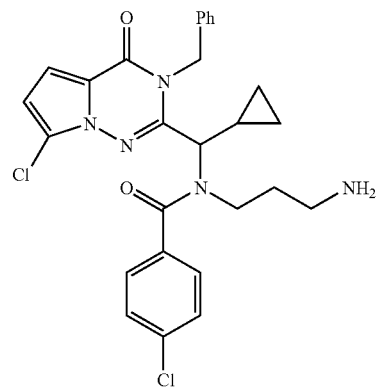

Example 18

(±)-N-(3-Amino-3-methyl-butyl)-N-[(3-benzyl-7-chloro-4-oxo-3,4-dihydro-pyrrolo[2,1-f][1,2,4]triazin-2-yl)-cyclopropyl-methyl]-4-chlorobenzamide, trifluoroacetic acid salt To a solution of (±)-(3-{[(3-benzyl-7-chloro-4-oxo-3,4-dihydro-pyrrolo[2,1-f][1,2,4]-triazin-2-yl)-cyclopropyl-methyl]-amino propyl)carbamic acid tert-butyl ester (Example 17 G, 20 mg, 0.04 mmol) and Et₃N (0.011 mL, 0.08 mmol) in CH₂Cl₂ (1 mL) at rt was added p-toluoyl chloride (0.006 mL, 0.047 mmol) under N₂ and the resulting mixture was stirred at rt for 30 min. The reaction mixture was then diluted with saturated NaHCO₃ solution, extracted with CH₂Cl₂ (20 mL). The organic solution was dried over MgSO₄ and concentrated to a light yellow residue. The residue was dissolved in CH₂Cl₂ (0.5 mL) and treated with TFA (0.3 mL) for 30 min. The reaction mixture was purified by preparative HPLC (C₁₈ YMC-Pack ODS, 100×20 mm, with 0.1% TFA/MeOH/H₂O) to afford the title compound (6.5 mg, 25%): ¹H NMR (D₂O) δ 7.46 (m, 4H), 7.20 (d, 1H, J=4.4 Hz), 7.16 (m, 2H), 6.90 (m, 2H), 6.80 (d, 1H, J=4.4 Hz), 5.52 (d, 1H, J=17.6 Hz), 5.21 (m, 2H), 3.52 (m, 2H), 2.66 (m, 2H), 2.03 (m, 2H), 1.66 (m, 2H), 0.71 (m, 2H), 0.50 (m, 1H), 0.32 (m, 1H); MS (ESI⁺) 524.19, 526.18 (M⁺+H).

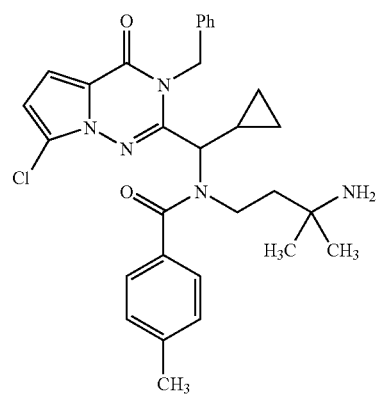

Example 19

(±)-N-(3-Amino-3-methyl-butyl)-N-[(3-benzyl-7-chloro-4-oxo-3,4-dihydropyrrolo[2,1-f][1,2,4]triazin-2-yl)-cyclopropyl-methyl]-4-methyl-benzamide, trifluroacetic acid A) (±)-2-(amino-cyclopropyl-methyl)-3-benzyl-7-chloro-3H-pyrrolo[2,1-f][1,2,4]triazin-4-one A mixture of 3-benzyl-7-chloro-2-(cyclopropyl-hydroxymethyl)-3H-pyrrolo[2,1-f][1,2,4]triazin-4-one (Example 17 G, 0.10 g, 0.29 mmol) and sodium azide (30 mg, 0.46 mmol) in DMF (2 mL) was stirred at rt under nitrogen overnight. The reaction mixture was diluted with EtOAc to 40 mL, washed with water and brine, dried over MgSO$_2$ and concentrated to a pale oil. The oil was dissolved in THF (6 mL) and water (0.2 mL), flushed with nitrogen and treated with triphenylphosphine (0.15 g, 0.58 mmol). The reaction mixture was heated at 66° C. for 5 h. The solvents were removed under reduced pressure. Purification of the residue by flash column chromatography (SiO$_2$, EtOAc/hexane/MeOH/NH$_4$OH 500:500:50:5) gave the title compound as a colorless oil (69 mg, 73%): $^1$H NMR (CDCl$_3$) δ 7.35 (m, 4H), 7.22 (d, 1H, J=7.7 Hz), 7.11 (m, 1H), 6.54 (m, 1H), 5.65 (m, 1H), 5.37 (m, 1H), 3.73 (m 1H), 2.00 (m, 1H),1.60 (m, 1H), 1.33 (m, 1H), 0.58 (m, 1H), 0.29 (m, 2H); MS (ESI$^+$) 329.09, 331.07 (M$^+$+H).

B) (±)-N-(3-Amino-3-methyl-butyl)-N-[(3-benzyl-7-chloro-4-oxo-3,4-dihydropyrrolo [2,1-f][1,2,4]triazin-2-yl)-cyclopropyl-methyl]-4-methyl-benzamide, trifluroacetic acid A solution of 3-benzyl-7-chloro-2-(cyclopropyl-hydroxymethyl)-3H-pyrrolo[2,1-f][1,2,4]triazin-4-one (69 mg, 0.21 mmol) and (1,1-dimethyl-3-oxo-propyl)-carbamic acid tert-butyl ester (Example 50 D, 90 mg, 0.45 mmol) in MeOH (3 mL) was stirred at rt under nitrogen for 15 min, then treated with 1 drop of HOAc, followed by NaBH(OAc)$_3$ (0.13 g, 0.58 mmol). The reaction mixture was stirred at rt overnight, quenched with aq. NaHCO$_3$ solution, extracted with EtOAc, dried over MgSO$_4$ and concentrated to an oil. To a solution of the oil and Et$_3$N (0.25 mL, 1.79 mmol) in CH$_2$Cl$_2$ (5 mL) was added p-toluoyl chloride (0.16 mL, 1.2 mmol) at rt under nitrogen and stirred at rt for 30 min. The reaction mixture was quenched with aq. NaHCO$_3$ solution and extracted with CH$_2$Cl$_2$ (20 mL). The organic phases were dried over MgSO$_4$ and concentrated to a light yellow residue. The residue was dissolved in CH$_2$Cl$_2$ (1 mL), treated with TFA (0.5 mL) and stirred at rt for 30 min. The mixture was concentrated to dryness and purified by preparative HPLC (C$_{18}$ YMC-Pack ODS, 100×20 mm, with 0.1% TFA/MeOH/H$_2$O) to give the title compound (10 mg, 66%): $^1$H NMR (CDCl$_3$) δ 7.35 (m, 1H), 7.25 (m, 2H), 7.15 (m, 1H), 7.10 (m, 1H), 7.01 (d, 1H, J=4.4 Hz), 6.47 (d, 1H, J=4.4 Hz), 5.91 (d, 1H, J=15.95 Hz), 5.10 (d, 1H, J=9.35 Hz), 4.73 (d, 1H, J=15.95 Hz), 3.70 (m 1H), 3.36 (m, 1H), 2.35 (m, 1H), 2.27 (s, 3H), 1.97 (m, 1H),1.61 (m, 1H), 1.39 (m, 1H), 0.98 (s, 3H), 0.69 (s, 3H), 0.41 (m, 1H), 0.28 (m, 2H); MS (ESI$^+$) 632.18 (M$^+$+H), 654.24, 657.35 (M$^+$+Na).

Example 20

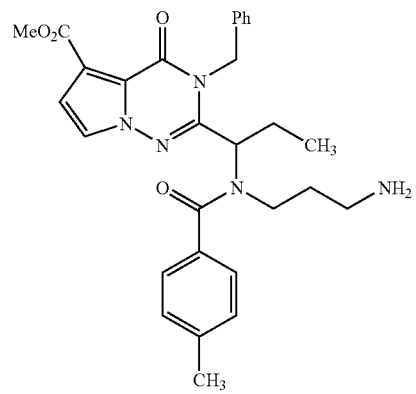

(±)-2-{1-[(3-Amino-propyl)-(4-methyl-benzoyl)-amino]-propyl}-3-benzyl-4-oxo-3,4-dihydro-pyrrolo[2,1-f][1,2,4]triazine-5-carboxylic acid methyl ester, hydrochloride salt A) 1-Amino-1H-pyrrole-2,3-dicarboxylic acid diethyl ester, hydrochloride salt 1H-Pyrrole-2,3-dicarboxylic acid diethyl ester (*Liebigs Ann. Chem.* 1987, 1117–1119, 1.23 g, 5.8 mmol) was added to a 0° C. mixture of NaH (60%, 0.35 g, 8.8 mmol) in DMF (20 mL). The resulting reaction mixture was stirred at 0° C. for 20 min and 2,4-dinitrophenyl hydroxylamine (*Tetrahedron Lett.* 1968, 16, 1909–1910 and *J. Heterocyclic Chem.* 1967, 413, 1.39 g, 7.0 mmol) was added portionwise. The reaction mixture was stirred for 1 h at 0° C., quenched with H$_2$O (200 ml), and extracted with EtOAc (3×75 ml). The combined organic extracts were washed with LiCl (10%, 4×70 ml), the organic layer dried (Na$_2$SO$_4$), filtered and concentrated in vacuo. The residue was treated with 4 N HCl in dioxane (2.0 ml) and concentrated in vacuo to afford the title compound as a white solid (0.55 g, 59%): $^1$H NMR (DMF-d$_7$) δ 7.14–7.15 (m, 1H), 6.54–6.58 (m, 3H), 4.37–4.53 (m, 4H), 1.39–1.51 (m, 6H); MS (ESI$^+$) 227 (M$^+$+H).

B) 2-Methyl-4-oxo-3,4-dihydro-pyrrolo[2,1-f][1,2,4]triazine-5-carboxylic acid ethyl ester Trifluoroacetic acid (0.45 ml, 5.85 mmol) was added to a solution of 1-amino-1H-pyrrole-2,3-dicarboxylic acid diethyl ester, hydrochloride salt in CH$_3$CN (20 ml) and heated to 85° C. for 12 h. The reaction mixture was concentrated in vacuo, diluted with CH$_3$CN (20 ml), treated with triethylamine (1.36 ml, 11.9 mmol), and heated to 85° C. for 6 h. The reaction mixture was concentrated in vacuo, dissolved in EtOAc and the organic layer washed with 1 N HCl (1×50 ml), saturated NaHCO$_3$ (3×50 ml), dried (Na$_2$SO$_4$), filtered and concentrated in vacuo to afford the title compound as a solid (0.20 g, 54%): $^1$H NMR (CDCl$_3$) δ 7.27–7.32 (m, 1H), 7.01–7.02 (m, 1H), 4.32–4.38 (m, 2H), 2.41 (s, 3H), 1.90 (br m, 1H), 1.35–1.40 (m, 3H); MS (ESI$^+$) 222 (M$^+$+H).

C) 3-Benzyl-2-methyl-4-oxo-3,4-dihydro-pyrrolo[2,1-f][1,2,4]triazine-5-carboxylic acid ethyl ester Benzyl bromide (0.112 ml, 0.945 mmol) was added to a solution of 2-methyl-4-oxo-3,4-dihydro-pyrrolo[2,1-f][1,2,4]triazine-5-carboxylic acid ethyl ester (0.19 g, 0.86 mmol) and $Cs_2CO_3$ (0.34 g, 1.06 mmol) in dioxane (5 mL) and the reaction mixture was heated to 95° C. for 3 h. The reaction mixture was quenched with saturated NaCl (100 mL), extracted with $CHCl_3$ (3×50 mL), the combined organic extracts dried ($Na_2SO_4$), filtered and concentrated in vacuo. The residue was purified by flash column chromatography on silica gel eluting with 1/1 hexane/EtOAc to afford the title compound as a solid (0.19 g, 70%): $^1H$ NMR ($CDCl_3$) δ 7.22–7.35 (m, 6H), 7.00–7.01 (m, 1H), 5.28 (s, 2H), 4.38 (q, 2H, J=7.19 Hz), 2.38 (s, 3H), 1.38 (t, 3H, J=7.09 Hz); MS (ESI$^+$) 312 (M$^+$+H).

D) 3-Benzyl-2-(2-dimethylamino-vinyl)-4-oxo-3,4-dihydro-pyrrolo[2,1-f][1,2,4]triazine-5-carboxylic acid methyl ester Dimethylformamide dimethylacetal (0.625 ml, 4.75 mmol) was added to a solution of 3-benzyl-2-methyl-4-oxo-3,4-dihydro-pyrrolo[2,1-f][1,2,4]triazine-5-carboxylic acid ethyl ester (0.18 g, 0.58 mmol) in DMF (1.0 mL) with 4 Å molecular sieves and the reaction mixture was heated to 140° C. in a sealed tube for 16 h. The reaction mixture was concentrated in vacuo, diluted with EtOAc (50 ml), the organic layer washed with LiCl (10%, 3×50 mL), dried ($Na_2SO_4$), filtered and concentrated in vacuo to afford the title compound (0.18 g, 85%): $^1H$ NMR ($CDCl_3$) δ 7.46 (d, 1H, J=12.44 Hz), 7.25–7.33 (m, 5H), 7.19 (m, 1H), 6.99 (m, 1H), 5.30 (s, 2H), 4.58 (d, 1H, J=12.49 Hz), 3.90 (s, 3H), 2.85 (s, 6H); MS (ESI$^+$) 353 (M$^+$+H).

E) 3-Benzyl-2-formyl-4-oxo-3,4-dihydro-pyrrolo[2,1-f][1,2,4]triazine-5-carboxylic acid methyl ester Sodium periodate (0.52 g, 2.4 mmol) was added to pH 7 buffer solution (2.5 ml) of 3-benzyl-2-(2-dimethylamino-vinyl)-4-oxo-3,4-dihydro-pyrrolo[2,1-f][1,2,4]triazine-5-carboxylic acid methyl ester (0.17 g, 0.48 mmol) in THF (3.0 mL) at room temperature. The reaction mixture was stirred at room temperature for 1 h. The reaction mixture was filtered through Celite® and the solids were washed with EtOAc (30 mL). The filtrate was washed with saturated NaCl (2×30 ml), dried ($Na_2SO_4$), filtered and concentrated in vacuo to afford the titled compound as a solid (0.15 g, 100%): $^1H$ NMR ($CDCl_3$) δ 9.41 (s, 1H), 7.16–7.40 (m, 7H), 5.68 (s, 2H), 3.88 (s, 3H); MS (ESI$^+$) 312 (M$^+$+H).

F) (±)-3-Benzyl-2-(1-hydroxy-propyl)-4-oxo-3,4-dihydro-pyrrolo[2,1-f][1,2,4]triazine-5-carboxylic acid methyl ester Ethyl magnesium bromide (1 M, 0.77 ml, 0.77 mmol) was added dropwise to a –78° C. solution of 3-benzyl-2-formyl-4-oxo-3,4-dihydro-pyrrolo[2,1-f][1,2,4]triazine-5-carboxylic acid methyl ester (0.12 g, 0.39 mmol) in $CH_2Cl_2$ (6.0 mL) over 45 min. The reaction mixture was stirred at –78° for 30 min, quenched with saturated $NH_4Cl$ (10 mL) and warmed to room temperature. The reaction mixture was extracted with $CHCl_3$ (3×25 mL), dried ($Na_2SO_4$), filtered and concentrated in vacuo. The residue was purified by flash column chromatography on silica gel eluting with 1/1 hexane/EtOAc to afford the title compound (0.070 g, 50%) as a solid: MS (ESI$^+$) 342 (M$^+$+H).

G) (±)-3-Benzyl-2-(1-methanesulfonyloxy-propyl)-4-oxo-3,4-dihydro-pyrrolo[2,1-f][1,2,4]triazine-5-carboxyic acid methyl ester Methanesulfonyl chloride (0.024 ml, 0.31 mmol) was added to a 0° C. solution of 3-benzyl-2-(1-hydroxy-propyl)-4-oxo-3,4-dihydro-pyrrolo[2,1-f][1,2,4]triazine-5-carboxylic acid methyl ester (0.007, 0.21 mmol) and triethylamine (0.052 mL, 0.37 mmol) in $CH_2Cl_2$ (1.0 mL) and the mixture was stirred at 0° C. for 30 min. The reaction mixture was then quenched with saturated $NaHCO_3$ (3.0 mL), extracted with EtOAc (3×3 ml). The combined organic layers were dried ($Na_2SO_4$), filtered and concentrated in vacuo to afford the title compound (0.043 g, 50%) which was used without further purification: MS (ESI$^+$) 420 (M$^+$+H).

H) (±)-3-Benzyl-2-[1-(3-tert-butoxycarbonylamino-propylamino)-propyl]-4-oxo-3,4-dihydro-pyrrolo[2,1-f][1,2,4]triazine-5-carboxylic acid methyl ester (3-Amino-propyl)-carbamic acid tert-butyl ester (Fluka, 0.054 ml, 0.31 mmol) was added to a solution of 3-benzyl-2-(1-methanesulfonyloxy-propyl)-4-oxo-3,4-dihydro-pyrrolo[2,1-f][1,2,4]triazine-5-carboxyic acid methyl ester (0.086 g, 0.21 mmol) and triethylamine (0.086 mL, 0.616 mmol) in DMF (1.0 mL) and the reaction mixture was heated to 75° C. for 4 h. The reaction mixture was quenched with saturated $NaHCO_3$ (2 mL) and extracted with EtOAc (3×10 mL). The combined organic extracts were washed with 10% LiCl (4×10 mL), dried ($Na_2SO_4$), filtered and concentrated in vacuo. The residue was purified by flash column chromatography on silica gel eluting with 8/1 to 1/1 hexane/EtOAc to afford the title compound (0.013 g, 14%) as a solid: $^1H$ NMR ($CDCl_3$) δ 6.98–7.26 (m, 8H), 5.75 (m, 1H), 4.95 (m, 2H), 3.86 (s, 3H), 3.65 (m, 1H), 3.00 (m, 2H), 2.45 (m, 1H), 2.00 (m, 1H), 1.50–1.75 (m, 4H) 1.36 (s, 9H), 0.88 (m, 3H); MS (ESI$^+$) 498 (M$^+$+H); HRMS (ESI$^+$) calculated: 498.2716 (M$^+$+H), found: 498.2720 (M$^+$+H).

I) (±)-3-Benzyl-2-{1-[(3-tert-butoxycarbonylamino-propyl)-(4-methyl-benzoyl)-amino]-propyl}-4-oxo-3,4-dihydro-pyrrolo[2,1-f][1,2,4]triazine-5-carboxylic acid methyl ester Triethylamine (0.011 mL, 0.079 mmol) was added to a solution of 3-benzyl-2-[1-(3-tert-butoxycarbonylamino-propylamino)-propyl]-4-oxo-3,4-dihydro-pyrrolo[2,1-f][1,2,4]triazine-5-carboxylic acid methyl ester (0.013 g, 0.026 mmol) and 4-methyl-benzoyl chloride (0.01 mL, 0.079 mmol) in $CH_2Cl_2$ (0.50 mL) at 0 C. The reaction mixture was stirred at 0° C. for 4 h, quenched with saturated $NaHCO_3$ (3 mL) and extracted with EtOAc (3×10 mL). The combined organic extracts were dried ($Na_2SO_4$), filtered and concentrated in vacuo. The residue was purified by flash column chromatography on silica gel eluting with 8/1 to 1/1 hexane/EtOAc to afford the title compound (0.015 g, 94%) as a solid: $^1H$ NMR ($CDCl_3$) δ 7.02–7.32 (m, 11H), 5.95 (m, 3H), 4.85 (m, 1H), 3.86 (s, 3H), 3.25 (m, 2H), 2.65 (m, 2H), 2.32 (s, 3H), 2.00 (m, 1H), 1.80 (m, 1H), 1.60 (m, 1H), 1.32 (s, 9H), 0.85 (m, 1H), 0.65 (m, 3H); MS (ESI$^+$) 616 (M$^+$+H); HRMS (ESI$^+$) calculated: 616.3135 (M$^+$+H). found: 616.3110 (M$^+$+H).

J) (±)-2–11-[(3-Amino-propyl)-(4-methyl-benzoyl)-amino]-propyl]-3-benzyl-4-oxo-3,4-dihydro-pyrrolo[2,1-f][1,2,4]triazine-5-carboxylic acid methyl ester, hydrochloride salt Anhydrous HCl in dioxane (4 M, 0.20 ml, 0.80 mmol) was added to 3-benzyl-2-{1-[(3-tert-butoxycarbonylamino-propyl)-(4-methyl-benzoyl)-amino]-propyl}-4-oxo-3,4-dihydro-pyrrolo[2,1-f][1,2,4]triazine-5-carboxylic acid methyl ester (0.003 g, 0.004 mmol) and the reaction mixture was stirred at 0° C. for 4 h. The reaction mixture was concentrated in vacuo, dissolved in aqueous $CH_3CN$ and lyophilized to afford the title compound (0.0021 g, 72%) as a white solid: MS (ESI$^+$) 516 (M$^+$+H); HRMS (ESI$^+$) calculated: 516.2611 (M$^+$+H), found: 516.2591 (M$^+$+H).

Example 21

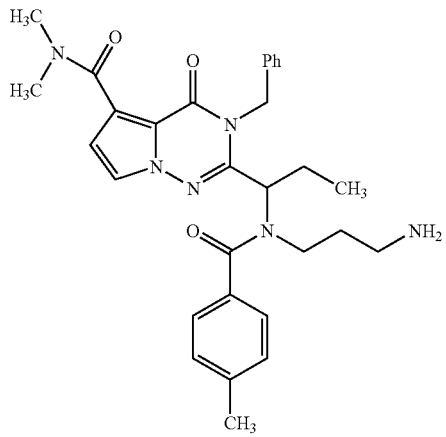

(±)-2-{1-[(3-Amino-propyl)-(4-methyl-benzoyl)-amino]-propyl}-3-benzyl-4-oxo-3,4-dihydro-pyrrolo[2,1-f][1,2,4]triazine-5-carboxylic acid dimethylamide, hydrochloride salt A) (±)-3-Benzyl-2-{1-[(3-tert-butoxycarbonylamino-propyl)-(4-methyl-benzoyl)-amino]-propyl}-4-oxo-3,4-dihydro-pyrrolo[2,1-f][1,2,4]triazine-5-carboxylic acid A mixture of lithium hydroxide (2 N, 0.122 mL, 0.24 mmol) and 3-benzyl-2-{1-[(3-tert-butoxycarbonylamino-propyl)-(4-methyl-benzoyl)-amino]-propyl}-4-oxo-3,4-dihydro-pyrrolo[2,1-f][1,2,4]triazine-5-carboxylic acid methyl ester, (Example 20 I, 0.003 g, 0.0049 mmol) in MeOH/THF (1:1, 0.20 mL) at 0° C. was stirred for 4 h. The reaction mixture was quenched with 1 N HCl (5 mL), extracted with EtOAc (3×10 ml), the combined organic extracts dried (Na$_2$SO$_4$), filtered and concentrated in vacuo to give the crude product as a solid. This crude product (0.0029 g, 60%) was used without further purification: MS (ESI$^+$) 602 (M$^+$+H).

B) (±)-{3-[[1-(3-Benzyl-5-dimethylcarbamoyl-4-oxo-3,4-dihydro-pyrrolo[2,1-f][1,2,4]triazin-2-yl)-propyl]-(4-methyl-benzoyl)-amino]-propyl}-carbamic acid tert-butyl ester A mixture of 3-benzyl-2-{1-[(3-tert-butoxycarbonylamino-propyl)-(4-methyl-benzoyl)-amino]-propyl}-4-oxo-3,4-dihydro-pyrrolo[2,1-f]-[1,2,4]triazine-5-carboxylic acid (0.0029 g, 0.0048 mmol), HOBt (0.0013 g, 0.0097 mmol), EDCI (0.002 g, 0.0097 mmol), dimethylamine (2 M in THF, 0.024 ml, 0.048 mmol) and DIPEA (0.003 mL, 0.019 mmol) in DMF (0.5 mL) were stirred at room temperature for 16 h. The reaction mixture was concentrated under vacuum, dissolved in EtOAc (3 mL). The organic solution was washed with 10% LiCl (3×2 mL), dried (Na$_2$SO$_4$), filtered and concentrated in vacuo. The residue was purified by flash column chromatography on silica gel eluting with 3/1 hexane/EtOAc to afford title compound as a solid (0.001 g, 33%): MS (ESI$^+$) 629 (M$^+$+H).

C) (±)-2-{1-[(3-Amino-propyl)-(4-methyl-benzoyl)-amino]-propyl}-3-benzyl-4-oxo-3,4-dihydro-pyrrolo[2,1-f][1,2,4]triazine-5-carboxylic acid dimethylamide, hydrochloride salt Anhydrous 4 N HCl in dioxane (0.04 mL 0.159 mmol) was added to 3-[[1-(3-benzyl-5-dimethylcarbamoyl-4-oxo-3,4-dihydro-pyrrolo[2,1-f][1,2,4]triazin-2-yl)-propyl]-(4-methyl-benzoyl)-amino]-propyl}-carbamic acid tert-butyl ester (0.001 g, 0.00159 mmol) and the resulting reaction mixture was stirred at 0° C. for 3 h and then concentrated in vacuo. The residue was dissolved in aqueous acetonitrile and lyophilized to afford title compound (0.001 g, 100%) as a white solid: MS (ESI$^+$) 529 (M$^+$+H). HRMS (ESI$^+$) calculated: 529.2927 (M$^+$+H). found: 529.2926 (M$^+$+H).

Example 22

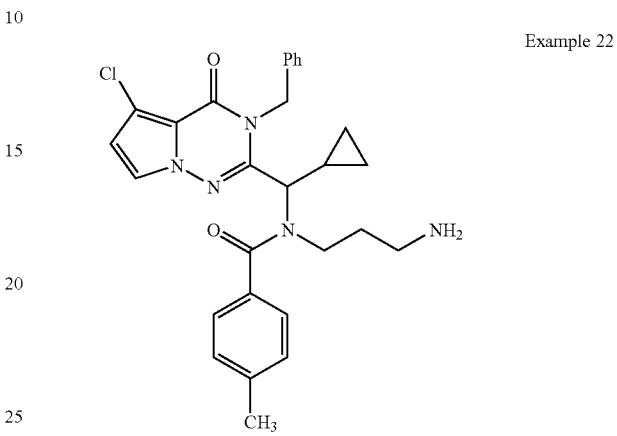

(±)-N-(3-Amino-propyl)-N-[(3-benzyl-5-chloro-4-oxo-3,4-dihydro-pyrrolo[2,1-f][1,2,4]triazin-2-yl)-cyclopropyl-methyl]-4-methyl-benzamide, hydrochloride salt A) 1-Amino-3-chloro-1H-pyrrole-2-carboxylic acid methyl ester, hydrochloride salt 1-Amino-3-chloro-1H-pyrrole-2-carboxylic acid methyl ester, hydrochloride salt was prepared from 3-chloro-1H-pyrrole-2-carboxylic acid methyl ester (*Tetrahedron* 1999, 4133–4152) using the same amination procedure outlined in Example 20 A.

B) 5-Chloro-2-methyl-3H-pyrrolo[2,1-f][1,2,4]triazin-4-one

A mixture of 1-amino-3-chloro-1H-pyrrole-2-carboxylic acid methyl ester, hydrochloride salt (11.0 g, 52.1 mmol) and trifluoroacetic acid (6.0 mL, 77.9 mmol) in acetonitrile (230 mL) was heated at 85° C. overnight. The reaction mixture was concentrated and treated with fresh acetonitrile (200 mL) and triethylamine (22.0 mL, 157.8 mmol). The reaction mixture was heated at 85° C. overnight and concentrated to small volume and diluted with water (100 mL). The mixture was then stirred at rt for 20 min. The precipitate was collected, washed with water and dried to give the title compound as a brown solid (7.67 g, 80%): $^1$H NMR (CD$_3$OD): δ 7.28 (s, 1H), 6.42 (s, 1H), 2.20 (s, 3H); MS (ESI$^+$) 184.02, 186.10 (M$^+$+H).

C) 3-Benzyl-5-chloro-2-methyl-3H-pyrrolo[2,1-f][1,2,4]triazin-4-one

Benzyl bromide (9.97 ml, 83.9 mmol) was added to a solution of 5-chloro-2-methyl-3H-pyrrolo[2,1-f][1,2,4]triazin-4-one (14 g, 76.3 mmol) and Cs$_2$CO$_3$ (29.7 g, 91.5 mmol) in dioxane (300 mL). The reaction mixture was stirred at 95° C. for 3 h, cooled to room temperature, filtered through Celite® and the filtrate concentrated in vacuo. The residue was dissolved in CHCl$_3$ (100 mL), treated with saturated NaCl solution (200 mL), and extracted with CHCl$_3$ (3×100 mL). The combined organic extracts were dried (Na₂SO₄), filtered and concentrated in vacuo. The residue was triturated with Et₂O, the solid filtered, washed with petroleum ether and dried in vacuo to afford the title compound (19.5 g, 94%) as a white solid: ¹H NMR (DMF-d₇) δ 7.57 (m, 1H), 7.32–7.41 (m, 5H), 6.65 (m, 1H), 5.31 (s, 2H), 2.38 (s, 3H); MS (ESI⁺) 274 (M⁺+H), HRMS (ESI⁺): calculated: 274.0747 (M⁺+H). found: 274.0757 (M⁺+H).

D) 3-Benzyl-5-chloro-2-(2-dimethylamino-vinyl)-3H-pyrrolo[2,1-f][1,2,4]triazin-4-one Dimethylformamide dimethylacetal (20 ml, 152 mmol) was added to a solution of 3-benzyl-5-chloro-2-methyl-3H-pyrrolo[2,1-f][1,2,4]triazin-4-one (9.0 g, 33 mmol) in DMF (100 mL) with MgSO₄ (5 g) and the reaction mixture was heated to 140° C. in a sealed tube for 16 h. The reaction mixture was concentrated in vacuo, the residue dissolved with EtOAc (50 mL) and a solid was precipitated by addition of petroleum ether (300 mL). The solid was filtered, washed with petroleum ether and dried in vacuo to afford title compound (5.4 g, 50%) as a solid: ¹H NMR (CDCl₃) δ 7.22 (d, 1H, J=12.43 Hz), 7.08–7.19 (m, 5H), 6.97 (m, 1H), 6.23 (m, 1H), 5.08 (s, 2H), 4.40 (d, 1H, J=12.49 Hz), 2.67 (s, 6H); MS (ESI⁺) 329 (M⁺+H).

E) 3-Benzyl-5-chloro-4-oxo-3,4-dihydro-pyrrolo[2,1-f][1,2,4]triazine-2-carbaldehyde Sodium periodate (17.3 g, 80.7 mmol) was added to a pH 7.0 buffered solution (75 mL) of 3-benzyl-5-chloro-2-(2-dimethylamino-vinyl)-3H-pyrrolo[2,1-f][1,2,4]triazin-4-one (5.3 g, 16.1 mmol) in THF (150 mL) at room temperature. The reaction mixture was stirred at room temperature for 1.5 h. The reaction mixture was filtered through Celite® and the solids washed with CHCl₃ (100 ml). The filtrate was wash with saturated NaCl (2×50 mL), dried (Na₂SO₄), filtered and concentrated in vacuo. The solid was azeotroped with toluene (2×50 mL) to afford the title compound as a solid (4.6 g, 100%): TLC, R_f=0.5 (2/1 hexane/EtOAc, UV); ¹H NMR (CDCl₃) δ 9.34 (s, 1H), 7.33 (m, 1H), 7.16–7.27 (m, 5H), 6.60 (m, 1H), 5.62 (s, 2H).

F) (±)-3-Benzyl-5-chloro-2-(cyclopropyl-hydroxy-methyl)-3H-pyrrolo[2,1-f][1,2,4]triazin-4-one Cyclopropyl magnesium bromide (Boulder Scientific, 0.78 M, 8.92 ml, 6.96 mmol) was added dropwise to a −78° C. solution of 3-benzyl-5-chloro-4-oxo-3,4-dihydro-pyrrolo[2,1-f][1,2,4]triazine-2-carbaldehyde (1.0 g, 3.48 mmol) in CH₂Cl₂ (20 mL) over 45 min. The reaction mixture was stirred at −78° C. for 30 min, warmed to room temperature and quenched with saturated NH₄Cl (100 mL). The reaction mixture was extracted with CHCl₃ (3×75 mL), dried (Na₂SO₄), filtered and concentrated in vacuo. The residue was purified by reverse phase C-18 chromatography eluting over a 30 minute gradient with 45–90% aqueous methanol with 0.1% TFA to afford the title compound (0.54 g, 48%) as a solid: ¹H NMR (DMF-d₇) δ 7.68 (m, 1H), 7.26–7.38 (m, 5H), 6.71 (m, 1H), 6.28 (d, 1H, J=6.41 Hz), 5.71 (m, 1H), 5.28 (m, 1H), 3.86 (m, 1H), 1.46 (m, 1H), 0.57–0.59 (m, 1H), 0.38–0.46 (m, 2H), 0.13 (m, 1H); MS (ESI⁺) 330 (M⁺+H); HRMS (ESI⁺) calculated: 330.1009 (M⁺+H). found: 330.1000 (M⁺+H).

G) (±)-3-Benzyl-5-chloro-2-(chloro-cyclopropyl-methyl)-3H-pyrrolo[2,1-f][1,2,4]triazin-4-one Thionyl chloride (2 M in CH₂Cl₂, 1.52 ml, 3.04 mmol) was added to solution of 3-benzyl-5-chloro-2-(cyclopropyl-hydroxy-methyl)-3H-pyrrolo[2,1-f][1,2,4]triazin-4-one (0.5 g, 1.52 mmol) and pyridine (0.49 mL, 6.08 mmol) in CH₂Cl₂ (10 ml) at 0° C. The reaction mixture was stirred at 0° C. for 45 min and then quenched by pouring on to ice. The solution was treated with 1 N HCl (100 mL) and extracted with CHCl₃ (3×100 mL). The combined organic extracts were washed with saturated NaHCO₃ (100 mL), dried (Na₂SO₄), filtered and concentrated in vacuo. The residue was purified by flash column chromatography on silica gel eluting with 4/1 hexane/EtOAc to afford the title compound (0.368 g, 70%) as a solid: ¹H NMR (DMF-d₇) δ 7.96 (m, 1H), 7.47–7.60 (m, 5H), 6.97 (m, 1H), 5.94 (m, 1H), 5.22 (m, 1H), 4.63 (d, 1H, J=9.99 Hz), 2.09–2.12 (m, 1H), 0.98–1.05 (m, 1H), 0.86–0.97 (m, 1H), 0.68–0.71 (m, 1H), 0.23–0.27 (m, 1H); MS (ESI⁺) 348 (M⁺+H), HRMS (ESI⁺) calculated: 348.0670 (M⁺+H). found: 348.0686 (M⁺+H).

H) (±)-(3-{[(3-Benzyl-5-chloro-4-oxo-3,4-dihydro-pyrrolo[2,1-f][1,2,4]triazin-2-yl)-cyclopropyl-methyl]-amino}-propyl)-carbamic acid tert-butyl ester (3-Amino-propyl)-carbamic acid tert-butyl ester (Fluka, 0.527 mL, 3.02 mmol) was added to a solution of 3-benzyl-5-chloro-2-(chloro-cyclopropyl-methyl)-3H-pyrrolo[2,1-f][1,2,4]triazin-4-one (0.35 g, 1.01 mmol) in NMP (3.3 mL) at room temperature. The reaction mixture was degassed with N₂ and then stirred at 100° C. for 12 h. The reaction mixture was cooled to room temperature and the crude product was purified by loading directly onto a reverse phase C-18 HPLC with a 30 min gradient eluting with 45–90% aqueous methanol with 0.1% TFA to afford the title compound (0.397 g, 81%) as a solid: ¹H NMR (DMF-d₇) 7.74 (m, 1H), 7.35–7.49 (m, 5H), 6.85 (m, 2H), 5.85 (m, 1H), 5.45 (m, 1H), 3.15–3.25 (m, 3H), 2.70–2.85 (m, 2H), 2.55 (br m, 1H), 1.55–165 (m, 2H), 1.47 (s, 9H), 1.40 (br m, 1H), 0.65–0.75 (m, 1H), 0.41–0.46 (m, 2H), 0.15 (br m, 1H); MS (ESI⁺) 486 (M⁺+H); HRMS (ESI⁺) calculated: 486.2272 (M⁺+H). found: 486.2256 (M⁺+H).

I) (±)-{3-[[(3-Benzyl-5-chloro-4-oxo-3,4-dihydro-pyrrolo[2,1-f][1,2,4]triazin-2-yl)-cyclopropyl-methyl]-(4-methyl-benzoyl)-amino]-propyl}-carbamic acid tert-butyl ester Triethylamine (0.425 mL, 3.05 mmol) was added to a 0° C. solution of (3-{[(3-benzyl-5-chloro-4-oxo-3,4-dihydro-pyrrolo[2,1-f][1,2,4]triazin-2-yl)-cyclopropyl-methyl]-amino}-propyl)-carbamic acid tert-butyl ester (0.74 g, 1.52 mmol) and 4-methylbenzoyl chloride (0.403 mL, 3.05 mmol) in CH₂Cl₂ (10 mL) and was stirred at 0° for 1.5 h. The reaction mixture was quenched with 1 N HCl (30 mL) and extracted with CHCl₃ (3×50 mL). The combined organic extracts were washed with saturated NaHCO₃ (1×100 mL), dried (Na₂SO₄), filtered and concentrated in vacuo. The residue was purified by flash column chromatography on silica gel eluting with 3/1 hexane/EtOAc to afford the title compound (0.90 g, 98%) as a solid: MS (ESI⁺) 604 (M⁺+H); HRMS (ESI⁺) calculated: 604.2691 (M⁺+H). found: 604.2702 (M⁺+H).

J) (±)-N-(3-Amino-propyl)-N-[(3-benzyl-5-chloro-4-oxo-3,4-dihydro-pyrrolo[2,1-f][1,2,4]triazin-2-yl)-cyclopropyl-methyl]-4-methyl-benzamide, hydrochloride salt Anhydrous HCl in dioxane (4 M, 10 mL, 40 mmol) was added to 3-[[(3-benzyl-5-chloro-4-oxo-3,4-dihydro-pyrrolo[2,1-f][1,2,4]triazin-2-yl)-cyclopropyl-methyl]-(4-methyl-benzoyl)-amino]-propyl}-carbamic acid tert-butyl ester (0.895 g, 1.48 mmol) and the reaction mixture was stirred at 0° C. for 1 h. The reaction mixture was warmed to room temperature, stirred for 2, concentrated in vacuo, dissolved in aqueous CH₃CN (25 mL) and lyophilized to afford the title compound (0.756 g, 95%) as a white solid: ¹H NMR (DMF-d₇) δ 0.12 (br m, 1H), 0.70–0.85 (m, 2H), 0.95 (br m, 1H), 2.15 (br m, 2H), 2.55 (br m, 1H), 2.61 (s, 3H), 2.90–3.01 (2H), 3.85–4.00 (m, 2H), 5.15 (br m, 1H), 5.45 (br m, 1H), 5.95 (br m, 1H), 7.00 (m, 1H), 7.51–7.66 (m, 9H), 8.05 (m, 1H), 8.80 (br m, 2H); MS (ESI+) 504 (M++H); HRMS (ESI+) calculated: 504.2166 (M++H). found: 504.2156 (M++H). Analysis for $C_{28}H_{30}N_5O_2Cl \cdot 0.94\ H_2O \cdot 1.0\ HCl \cdot 0.12\ C_4H_8O_2$ Calc: C, 60.43; H 6.03; N, 12.37; Cl, 12.53. Found: C 60.43; H, 5.92; N, 11.82; Cl, 12.97.

Example 23

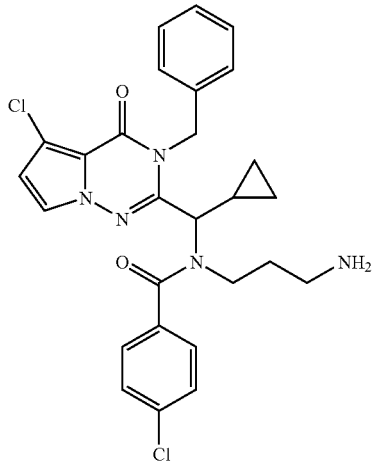

(±)-N-(3-amino-propyl)-N-[(3-benzyl-5-chloro-4-oxo-3,4-dihydro-pyrrolo[2,1-f][1,2,4]triazin-2-yl)-cyclopropyl-methyl]-4-chloro-benzamide, hydrochloride salt A) (±)-{3-[[(3-Benzyl-5-chloro-4-oxo-3,4-dihydro-pyrrolo[2,1-f][1,2,4]triazin-2-yl)-cyclopropyl-methyl]-(4-chloro-benzoyl)-amino]-propyl}-carbamic acid tert-butyl ester (±)-(3-{[(3-Benzyl-5-chloro-4-oxo-3,4-dihydro-pyrrolo[2,1-f][1,2,4]triazin-2-yl)-cyclopropyl-methyl]-amino}-propyl)-carbamic acid tert-butyl ester (Example 22H, 16 mg, 0.033 mmol) in methylene chloride (1.5 mL) was treated with triethylamine (5 µL, 0.036 mmol), and p-chlorobenzoyl chloride (6 mg, 0.034 mmol) at 0° C. and the resulting mixture was stirred at room temperature for 1 h. The mixture was diluted with methylene chloride (5 mL), washed with saturated sodium bicarbonate, dried (MgSO4) and concentrated. The residue was purified by flash column chromatography on silica gel eluting with ethyl acetate/hexanes to give the title compound (8 mg) as a clear oil: MS (ESI+) 604.2 (M++H).

B) (±)-N-(3-amino-propyl)-N-[(3-benzyl-5-chloro-4-oxo-3,4-dihydro-pyrrolo[2,1-f][1,2,4]triazin-2-yl)-cyclopropyl-methyl]-4-chloro-benzamide, hydrochloride salt {3-[[(3-Benzyl-5-chloro-4-oxo-3,4-dihydro-pyrrolo[2,1-f][1,2,4]triazin-2-yl) cyclopropyl-methyl]-(4-chloro-benzoyl)-amino]-propyl}-carbamic acid tert-butyl ester (8 mg) was treated with 4 N HCl/dioxane (1 mL) and the resulting mixture stirred at room temperature for 18 h. The mixture was concentrated under high vacuum to give the title compound (6 mg) as a white solid: 1H NMR (DMSO-d6) δ −0.35 (m, 1H), 0.40 (m, 1H), 0.50 (m, 1H), 0.57 (m, 1H), 1.53 (m, 1H), 1.80 (m, 1H), 1.89 (m, 1H), 2.56 (m, 2H), 3.56 (m, 2H), 4.85 (m, 1H), 5.16 (m, 1H), 5.80 (m, 1H), 6.66 (m, 1H), 7.23 (bs, 3H), 7.25 (m, 2H), 7.30–7.40 (m, 4H), 7.46–7.49 (m, 3H), 7.56 (m, 1H), 7.99 (m, 1H); HRMS (ESI+) 524.1629 (M+H)+ for $C_{27}H_{28}N_5O_2Cl_2$.

Example 24

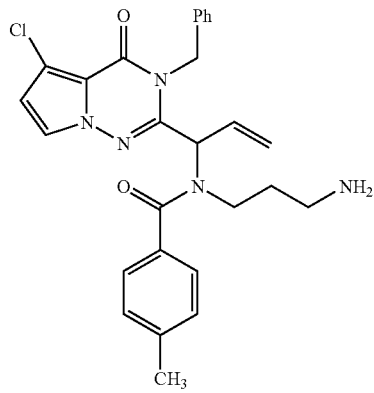

(±)-N-(3-Amino-propyl)-N-[1-(3-benzyl-5-chloro-4-oxo-3,4-dihydro-pyrrolo[2,1-f][1,2,4]triazin-2-yl)-allyl]-4-methyl-benzamide, trifluoroacetic acid salt A) (±)-3-Benzyl-5-chloro-2-(1-hydroxy-allyl)-3H-pyrrolo[2,1-f][1,2,4]triazin-4-one To a solution of 3-benzyl-5-chloro-4-oxo-3,4-dihydro-pyrrolo[2,1-f][1,2,4]triazine-2-carbaldehyde (Example 22 E, 287 mg, 1 mmol) in THF (4 mL) at −50° C. was added a vinylmagnesium bromide solution (1.5 mL of 1 M solution) under Ar. The mixture was stirred for 2 h, slowly warmed to rt over 2 h and stirred at rt for 30 min. The reaction mixture was quenched by the addition of 0.2 mL of HOAc followed by water (15 mL) and EtOAc (40 mL). The organic layer was dried over MgSO4 and concentrated in vacuo to obtain the crude title compound as a brown solid (315 mg, 100%) which was used in the next step without any further purification: 1H NMR (CDCl3) δ 7.10–7.50 (m, 6H), 6.47 (s, 1H), 6.01 (m, 1H), 5.05–5.25 (m, 4H), 5.05 (s, 1H); 13C NMR (CDCl3): δ 153.9, 149.8, 135.9, 135.4, 128.8, 127.7, 126.3, 119.8, 118.5, 113.6, 111.6, 70.4, 44.1.

B) (±)-{3-[1-(3-Benzyl-5-chloro-4-oxo-3,4-dihydro-pyrrolo[2,1-f][1,2,4]triazin-2-yl)-allylamino]-propyl}-carbamic acid tert-butyl ester To a solution of (±)-3-benzyl-5-chloro-2-(1-hydroxy-allyl)-3H-pyrrolo[2,1-f][1,2,4]triazin-4-one (315 mg, 1 mmol) in THF (4 mL) and pyridine (0.5 mL) at an ice bath temperature was added methansulfonyl chloride (85 µL), and the mixture was left at 5° C. for 8 h and then at rt for 8 h. EtOAc (40 mL) and 1 N aq HCl (10 mL) were added to the reaction mixture, the organic layer was separated, washed with water and dilute aq NaHCO3 (10 mL), dried over MgSO4 and concentrated to obtain the crude mesylate compound (250 mg, 63%) as a brown solid which was used directly in the next step: 1H NMR (CDCl3) δ 7.20–7.37 (m, 5H), 6.52 (s, 1H), 6.30 (m, 1H), 6.00 (d, 1H, J=7 Hz), 4.87–5.25 (m, 4H), 3.70 (s, 3H).

A mixture of the above crude mesylate intermediate (250 mg), N-Boc-propyldiamine (Fluka, 300 mg) in EtOH (3.5 mL) was heated at 65° C. for 8 h. After concentrating the mixture in vacuo, EtOAc (40 mL) and water (10 mL) were added to the residue, the organic layer was separated, dried over MgSO4 and concentrated to obtain the crude title compound (280 mg, 59% overall) as a viscous brown solid. This material was used directly in the next step. 1H NMR (CDCl₃) δ 7.15–7.35 (m, 5H), 6.46 (s, 1H), 5.89 (m, 1H), 5.22 (d, 1H, J=7 Hz), 4.87–5.25 (m, 4H), 2.75–3.31 (m, 4H), 1.66 (m, 2H), 1.40 (s, 9H).

C) (±)-N-(3-Amino-propyl)-N-[1-(3-benzyl-5-chloro-4-oxo-3,4-dihydro-pyrrolo[2,1-f][1,2,4]triazin-2-yl)-allyl]-4-methyl-benzamide, trifluoroacetic acid salt To a mixture of crude (±)-{3-[1-(3-benzyl-5-chloro-4-oxo-3,4-dihydro-pyrrolo[2,1-f][1,2,4]triazin-2-yl)-allylamino]-propyl}-carbamic acid tert-butyl ester (280 mg, 0.59 mmol) and Et₃N in CH₂Cl₂ (5 mL) at rt was added p-toluoyl chloride (180 μL). The reaction mixture was allowed to stand at rt for 5 h. Aqueous NaHCO₃ solution (15 mL) and CH₂Cl₂ (30 mL) were added, the organic layer was separated, dried over MgSO₄ and concentrated to obtain the crude product as a viscous brown material. This material was mixed with CH₂Cl₂ (8 mL) and TFA (1 mL) and allowed to stand at rt for 1 h. The reaction mixture was concentrated in vacuo and the residue was purified by preparative HPLC to afford the title compound (45 mg, 15%) as a beige solid: MS (ESI⁺) 490, 492 (M⁺+H).

Example 25

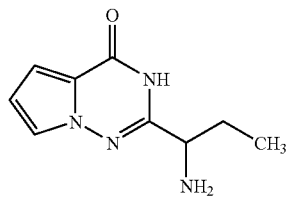

(±)-2-(1-Amino-propyl)-3H-pyrrolo[2,1-f][1,2,4]triazin-4-one, hydrochloride salt A) (±)-1-[[2-BOC-aminobutyryl]amino]pyrrole-2-carboxamide PyBOP was added to a solution of the d,l-N-BOC-α-aminobutyric acid (*J. Org. Chem.* 1990, 55, 3186–3194, 8.10 g, 40.0 mmol), diisopropylethylamine (774 mg, 60.0 mmol) and DMF (100 mL) at room temperature. The reaction mixture was stirred for 10 min. 1-Aminopyrrole-2-carboxamide (*J. Heterocyclic Chem.* 1994, 31, 781–786) was added to the resulting mixture and stirred at room temperature for 18 h. The mixture was concentrated under reduced pressure and the residue partitioned between ethyl acetate and saturated aqueous sodium bicarbonate. The organic phase was washed with water, brine, dried (MgSO₄) and concentrated in vacuo to a gum. The crude product was purified by flash column chromatography on silica gel eluting with ethyl acetate/hexanes to give the title compound (9.5 g, 77%) as a white solid: ¹H NMR (DMSO-d₆) δ 0.98 (t, 3H, J=7.15 Hz), 1.49 (s, 9H), 1.65 (m, 1H), 1.96 (m, 1H), 3.27 (m, 1H), 3.43 (m, 1H), 4.08 (m, 1H), 6.15 (s, 1H), 6.91 (s, 1H), 7.05 (s, 1H), 7.51 (bs, 1H).

B) (±)-[1-(4-Oxo-3,4-dihydro-pyrrolo[2,1-f][1,2,4]triazin-2-yl)-propyl]-carbamic acid tert-butyl ester A mixture of 1-[[2-BOC-aminobutyryl]amino]pyrrole-2-carboxamide (10.0 g, 32.2 mmol), 1 M KOH (150 mL), and ethanol (150 mL) was stirred at reflux for 18 h then cooled to room temperature and acidified to pH 4 using 2 M KHSO₄. The precipitate was collected by filtration, washed with water, dried on the funnel, suspended in toluene (3×150 mL) and concentrated to dryness to give the title compound (7.4 g, 78%) as a white solid: ¹H NMR (DMSO-d₆) δ 0.88 (t, 3H, J=7.15 Hz), 1.36 (s, 9H), 1.69 (m, 1H), 1.76 (m, 1H), 4.22 (s, 1H), 6.51 (s, 1H), 6.86 (s, 1H), 7.09 (s, 1H), 7.55 (brs, 1H).

C) (±)-2-(1-Amino-propyl)-3H-pyrrolo[2,1-f][1,2,4]triazin-4-one, hydrochloride salt A solution of [1-(4-oxo-3,4-dihydro-pyrrolo[2,1-f][1,2,4]triazin-2-yl)-propyl]-carbamic acid tert-butyl ester (10 mg, 0.034 mmol) in absolute methanol (0.5 mL) was treated with 2 N HCl/diethyl ether (2 mL) and the mixture stirred at room temperature overnight. The resulting white suspension was concentrated under vacuum and the solid residue triturated with diethyl ether and dried under vacuum to give the title compound (6 mg, 77%) as white powder: ¹H NMR (DMSO-d₆) δ 1.08 (t, 3H, J=7.15 Hz), 2.02 (m, 1H), 2.11 (m, 1H), 4.20 (s, 1H), 6.60 (s, 1H), 7.03 (s, 1H), 7.54 (s, 1H).

Example 26

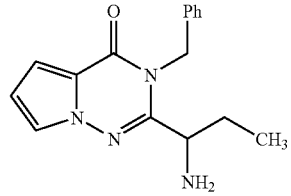

(±)-2-(1-Amino-propyl)-3-benzyl-3H-pyrrolo[2,1-f][1,2,4]triazin-4-one, hydrochloride salt A) (±)-[1-(3-Benzyl-4-oxo-3,4-dihydro-pyrrolo[2,1-f][1,2,4]triazin-2-yl)-propyl]-carbamic acid tert-butyl ester A mixture of the 1-(4-oxo-3,4-dihydro-pyrrolo[2,1-f][1,2,4]triazin-2-yl)-propyl]-carbamic acid tert-butyl ester (Example 25 B, 2.90 g, 10.0 mmol) and 1,4-dioxane (120 mL) was treated with cesium carbonate (6.50 g, 20.0 mmol) and stirred at room temperature for 40 min. Benzylbromide (1.88 g, 11.0 mmol) was added to the mixture and that was then refluxed under nitrogen for 3.5 h. The 1,4-dioxane was removed under vacuum and the residue diluted with water (175 mL) and extracted with diethyl ether (2×125 mL). The extracts were pooled, dried (MgSO₄) and concentrated to give a mixture of O-benzylated and N-benzylated products. The mixture was purified by flash column chromatography on silica gel using 1:19 ethyl acetate/hexanes to elute the O-benzylated product and then 1:4 ethyl acetate/hexanes to elute the N-benzylated product. The fractions containing the N-benzylated product were concentrated to yield 1-(3-benzyl-4-oxo-3,4-dihydro-pyrrolo[2,1-f][1,2,4]triazin-2-yl)-propyl-carbamic acid tert-butyl ester (3.0 g, 79%) as a white solid: ¹H NMR (DMSO-d₆) δ 0.53 (t, 3H, J=7.15 Hz), 1.20 (s, 9H), 1.52 (q, 2H, J=7.15 Hz), 4.38 (m, 1H), 4.83 (m, 1H), 5.55 (m, 1H), 6.47 (m, 1H), 6.80 (m, 1H), 7.06–7.20 (m, 5H), 7.33 (s, 1H), 7.48 (s, 1H).

B) (±)-2-(1-Amino-propyl)-3-benzyl-3H-pyrrolo[2,1-f][1,2,4]triazin-4-one, hydrogen chloride salt A mixture of 1-(3-benzyl-4-oxo-3,4-dihydro-pyrrolo[2,1-f][1,2,4]triazin-2-yl)-propyl]-carbamic acid tert-butyl ester (2.90 g, 7.59 mmol) and 4 N HCl/1,4-dioxane (150 mL) was stirred at room temperature for 90 min. The mixture was then concentrated under vacuum to give the title compound (2.40 g, 100%) as an off-white solid: ¹H NMR (DMSO-d₆) δ 0.51 (t, 3H, J=7.15 Hz), 1.57 (m, 2H), 4.15 (m, 1H), 5.02 (m, 1H), 5.18 (m, 1H), 6.46 (s, 1H), 7.04–7.18 (m, 5H) 6.82 (s, 1H), 7.42 (s, 1H), 8.53 (bs, 3H).

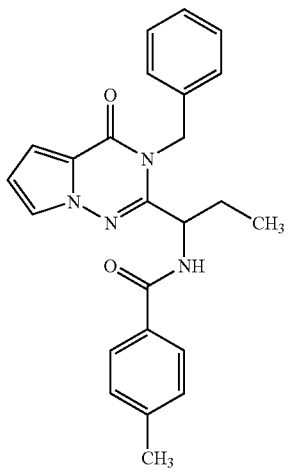

(±)-N-[1-(3-Benzyl-4-oxo-3,4-dihydro-pyrrolo[2,1-f][1,2,4]triazin-2-yl)-propyl]-4-methyl-benzamide Triethylamine (15 µL, 0.11 mmol) and p-toluyl chloride (15 mg, 0.098 mmol) were added to a solution of 2-(1-amino-propyl)-3-benzyl-3H-pyrrolo[2,1-f][1,2,4]triazin-4-one (Example 26, 25 mg, 0.089 mmol) in methylene chloride (1 mL) and the mixture was stirred at room temperature for 45 min. The mixture was diluted with methylene chloride (5 mL), washed with saturated $NaHCO_3$, dried ($MgSO_4$) and concentrated to give a yellow oil. The crude product was purified by flash column chromatography on silica gel eluting with ethyl acetate/hexanes to give the title compound (30 mg, 86%): $^1$H NMR (DMSO-$d_6$) δ 0.71 (t, 3H, J=7.15 Hz), 1.81 (m, 2H), 2.34, (s, 3H), 5.01 (m, 1H), 5.03 (m, 1H), 5.55 (m, 1H), 6.62 (s, 1H), 6.97 (s, 1H), 7.22–7.24 (m, 5H), 7.30–7.33 (m, 2H), 7.64 (bs, 1H), 7.73 (s, 2H), 8.86 (s, 1H).

Example 28

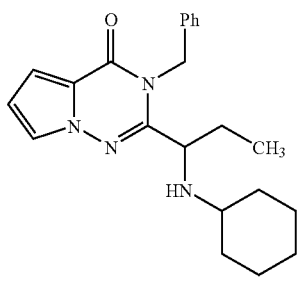

(±)-3-Benzyl-2-(1-cyclohexylamino-propyl)-3H-pyrrolo[2,1-f][1,2,4]triazin-4-one

Acetic acid (65 µl, 0.95 mmol) and sodium triacetoxyborohydride (200 mg, 0.95 mmol) were added to a solution of 2-(1-amino-propyl)-3-benzyl-3H-pyrrolo[2,1-f][1,2,4]triazin-4-one (Example 26, 180 mg, 0.64 mmol) and cyclohexanone (62 mg, 0.64 mmol) in 1,2-dichloroethane (5 mL). The mixture was stirred for 4 h at room temperature concentrated under reduced pressure and the residue partitioned between ethyl acetate and saturated sodium bicarbonate. The organic phase was separated, dried ($MgSO_4$) and concentrated to give the title compound (211 mg, 91%) as a white solid: $^1$H NMR (DMSO-$d_6$) δ 0.69–1.19 (m, 10H), 1.38–1.89 (m, 6H), 1.99 (m, 1H), 3.63 (m, 1H), 4.82 (m, 1H), 5.80 (m, 1H), 6.55 (s, 1H), 7.06 (s, 1), 7.15 (m, 2H), 7.22–7.35 (m, 4H).

Example 29

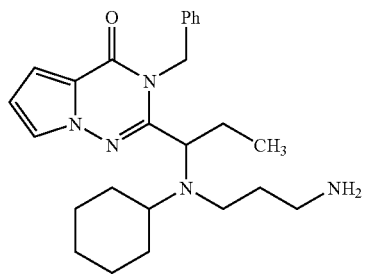

(±)-2-{1-[(3-Amino-propyl)-cyclohexyl-amino]-propyl}-3-benzyl-3H-pyrrolo[2,1-f][1,2,4]triazin-4-one, bistrifluoracetic acid salt A) (±)-(3-{[1-(3-benzyl-4-oxo-3,4-dihydro-pyrrolo[2,1-f][1,2,4]triazin-2-yl)-propyl]-cyclohexyl-amino}-propyl)-carbamic acid 9H-fluoren-9-ylmethyl ester A mixture of 3-benzyl-2-(1-cyclohexylamino-propyl)-3H-pyrrolo[2,1-f][1,2,4]triazin-4-one (Example 28, 150 mg, 0.41 mmol), (3-oxo-propyl)-carbamic acid 9H-fluoren-9-ylmethyl ester (*Org. Lett.* 2002, 4, 3001–3003, 184 mg, 0.62 mmol), acetic acetic (1.5 eq), 4 Å molecular sieves (100 mg), and 1,2-dichloroethane (10 mL) was stirred at room temperature for 30 min, then treated with sodium triacetoxyborohydride (130 mg, 0.62 mmol). After 3 h, the mixture was filtered and the filtrate washed with saturated sodium bicarbonate and water, dried ($MgSO_4$), and concentrated. The residue was purified by flash column chromatography on silica gel eluting with ethyl acetate/hexanes to give the title compound as a white solid (115 mg, 44%): MS (ESI$^+$) 644.44 (M$^+$+H).

B) (±)-2-{1-[(3-Amino-propyl)-cyclohexyl-amino]-propyl}-3-benzyl-3H-pyrrolo[2,1-f][1,2,4]triazin-4-one, bis trifluoroacetic acid salt A mixture of (3-{[1-(3-benzyl-4-oxo-3,4-dihydro-pyrrolo[2,1-f][1,2,4]triazin-2-yl)-propyl]-cyclohexyl-amino}-propyl)-carbamic acid 9H-fluoren-9-ylmethyl ester (110 mg, 0.17 mmol), THF (2 mL) and piperidine (1 mL) was stirred at room temperature for 18 h and then concentarted under vacuum. The residue was purified by preprative HPLC on a Shimadzu S5 VP-ODS 20×100 mm column using methanol:water containing 0.1% trifluroacetic acid as the eluent. The fractions containing the product were combined and concentrated under vacuum to give a gum. The gum was redissolved in absolute methanol, dried ($Na_2SO_4$) and concentrated to give the title compound as a pale yellow solid (55 mg, 50%): $^1$H NMR (DMSO-$d_6$) δ 0.55 (t, 3H, J=7.15 Hz), 0.86 (m, 1H), 1.02 (m, 3H), 1.30–1.54 (m, 8H), 2.32–2.45 (m, 3H), 2.46–2.62 (m, 2H), 2.75 (m, 1H), 3.48 (m, 1H), 5.20 (m, 1H), 5.49 (m, 1H), 6.55 (s, 1H), 6.88 (s, 1H), 7.02 (m, 2H), 7.18 (m, 1H), 7.26 (m, 2H), 7.49 (bs, 3H), 7.58 (s, 1H); MS (ESI$^+$) 422.1 (M$^+$+H).

Example 30

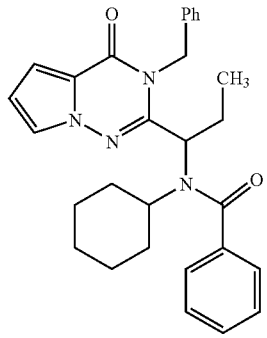

(±)-N-[1-(3-Benzyl-4-oxo-3,4-dihydro-pyrrolo[2,1-f]
[1,2,4]triazin-2-yl)-propyl]-N-cyclohexyl-benzamide 3-Benzyl-2-(1-cyclohexylamino-propyl)-3H-pyrrolo[2,1-f][1,2,4]triazin-4-one (Example 28, 26.3 mg, 0.072 mmol) in CHCl$_3$ (1.5 mL) at 25° C. was treated with benzoylchloride (34.9 mg, 0.248 mmol) and triethylamine (16.8 mg, 0.166 mmol). The resulting mixture was stirred at 25° C. for 18 h, then concentrated under vacuum and purified by preparative HPLC using a YMC S10 ODS 20×100 mm column affording the desired compound (8.0 mg, 23.7%) as a colorless film: LC/MS 94% at 4.42 min (ESI$^+$) 469 (M$^+$+H).

Example 31

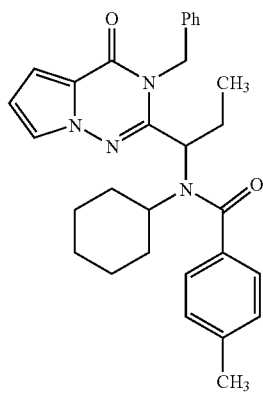

(±)-N-[1-(3-Benzyl-4-oxo-3,4-dihydro-pyrrolo[2,1-f]
[1,2,4]triazin-2-yl)-propyl]-N-cyclohexyl-4-methyl-
benzamide 3-Benzyl-2-(1-cyclohexylamino-propyl)-3H-pyrrolo[2,1-f][1,2,4]triazin-4-one (Example 28, 26.3 mg, 0.072 mmol) in CHCl$_3$ (1.5 mL) at 25° C. was treated with p-toluoyl chloride (38.3 mg, 0.248 mmol) and triethylamine (16.8 mg, 0.166 mmol). The resulting mixture was stirred at 25° C. for 18 h, then concentrated under vacuum and purified by preparative HPLC using a YMC S10 ODS 20×100 mm column affording the desired compound (5.5 mg, 15.8%) as a colorless film: LC/MS 89% at 4.48 min (ESI$^+$) 483 (M$^+$+H).

Example 32

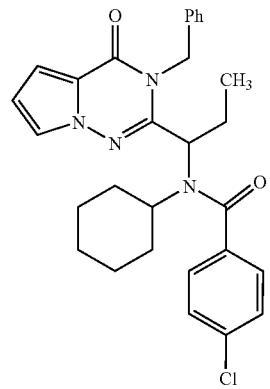

(±)-N-[1-(3-Benzyl-4-oxo-3,4-dihydro-pyrrolo[2,1-f]
[1,2,4]triazin-2-yl)-propyl]-4-chloro-N-cyclohexyl-
benzamide 3-Benzyl-2-(1-cyclohexylamino-propyl)-3H-pyrrolo[2,1-f][1,2,4]triazin-4-one (Example 28, 26.3 mg, 0.072 mmol) in CHCl$_3$ (1.5 mL) at 25° C. was treated with 4-chlorobenzoyl chloride (43.4 mg, 0.248 mmol) and triethylamine (16.8 mg, 0.166 mmol). The resulting mixture was stirred at 25° C. for 18 h, then concentrated under vacuum and purified by preparative HPLC using a YMC S10 ODS 20×100 mm column affording the desired compound (4.5 mg, 12.4%) as a colorless film: LC/MS 80% at 4.47 min (ESI$^+$) 503 (M$^+$+H).

Example 33

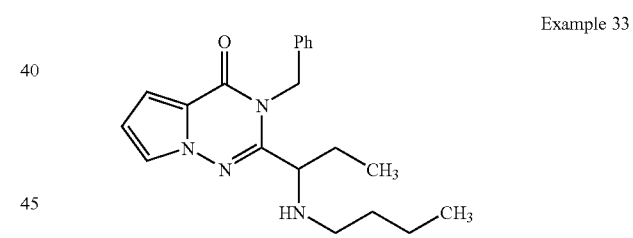

(±)-3-Benzyl-2-(1-butylamino-propyl)-3H-pyrrolo[2,
1-f][1,2,4]triazin-4-one, trifluoroacetic acid salt 2-(1-Amino-propyl)-3-benzyl-3H-pyrrolo[2,1-f][1,2,4]triazin-4-one (Example 26, 15 mg, 0.047 mmol) and butanal (4.0 mg, 0.0565 mmol) were dissolved in CH$_3$OH (2.5 mL) and stirred for 1 h at 25° C. The mixture was then treated with NaBH(OAc)$_3$ (11.97 mg, 0.0565 mmol) and stirred for 18 h. The reaction mixture was concentrated under vacuum and purified by preparative HPLC using a YMC S10 ODS 30×100 mm column affording the desired material (9.0 mg, 57%) as a colorless film: $^1$H NMR (CD$_3$OD, 400 MHz) δ 7.58 (m, 1H), 7.38 (m, 2H), 7.32 (m, 2H), 7.13 (m, 1H), 6.75 (m, 1H), 5.73 (d, 1H, J=16.5 Hz), 5.03 (d, 1H, J=16.5 Hz), 4.45 (t, 1H, J=5.5 Hz), 2.75 (m, 1H), 2.51 (m, 1H), 2.00 (m, 2H), 1.35 (m, 2H), 1.16 (m, 2H), 0.94 (t, 3H, J=7.7 Hz), 0.85 (t, 3H J=7.7 Hz); LC/MS (ESI$^+$) 339 (M$^+$+H).

Example 34

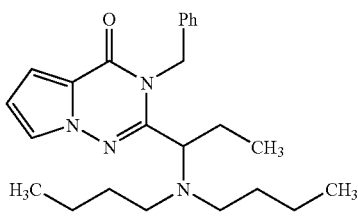

(±)-3-Benzyl-2-(1-dibutylamino-propyl)-3H-pyrrolo
[2,1-f][1,2,4]triazin-4-one, trifluoroacetic acid salt 2-(1-Amino-propyl)-3-benzyl-3H-pyrrolo[2,1-f][1,2,4]
triazin-4-one (Example 26, 15 mg, 0.047 mmol) and butanal
(17.0 mg, 0.235 mmol) were dissolved in $CH_3OH$ (2.5 mL)
and stirred for 1 h at 25° C. The mixture was then treated
with $NaBH(OAc)_3$ (49.8 mg, 0.235 mmol) and stirred for 18
h. The reaction mixture was concentrated under vacuum and
purified by preparative HPLC using a YMC S10 ODS
30×100 mm column affording the desired compound (18.0
mg, 97%) as a colorless film: $^1H$ NMR ($CD_3OD$, 400 MHz,
130° C.) δ 7.59 (s, 1H), 7.32 (m, 5H), 7.19 (m, 1H), 6.72 (m,
1H), 5.82 (d, 1H, J=16.5 Hz), 5.00 (d, 1H, J=16.5 Hz), 4.5
(m, 1H), 2.5 (m, 3H), 2.19 (m, 1H), 2.12 (m, 1H), 1.05–1.60
(bm, 8H), 0.75–1.03 (bm, 10H); LC/MS ($ESI^+$) 395 ($M^+$+
H).

Example 35

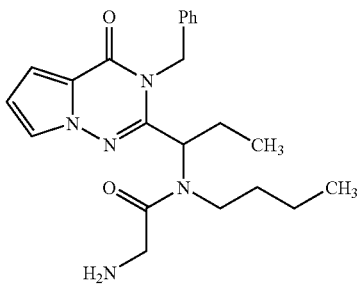

(±)-2-Amino-N-[1-(3-benzyl-4-oxo-3,4-dihydro-
pyrrolo[2,1-f][1,2,4]triazin-2-yl)-propyl]-N-butyl-
acetamide, trifluoroacetic acid salt 3-Benzyl-2-(1-butylamino-propyl)-3H-pyrrolo[2,1-f][1,
2,4]triazin-4-one (Example 33, 28.0 mg, 0.0828 mmol) in
$CH_2Cl_2$ (5 mL) was treated with N-BOC-glycine (21.7 mg,
0.124 mmol) and diisopropylcarbodiimide (15.6 mg, 0.124
mmol) and stirred for 4 h at 25° C. The mixture was
concentrated under vacuum and purified by preparative
HPLC using a YMC S10 ODS 20×100 mm column. The
product was dissolved in $CH_2Cl_2$ (5 mL) and treated with
TFA (1 mL). The resulting mixture was stirred at 25° C. for
0.5 h, then concentrated under vacuum and purified by
preparative HPLC using a YMC S10 ODS 20×100 mm
column affording the desired compound (19 mg, 45%) as a
colorless film: LC/MS 95% at 3.04 min ($ESI^+$) 396 ($M^+$+H).

Example 36

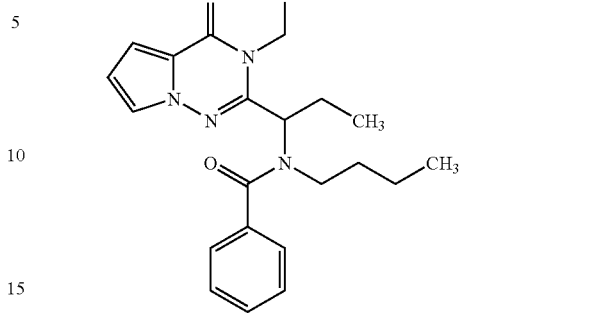

(±)-N-[1-(3-Benzyl-4-oxo-3,4-dihydro-pyrrolo[2,1-f]
[1,2,4]triazin-2-yl)-propyl]-N-butyl-benzamide, trif-
luoroacetic acid salt 3-Benzyl-2-(1-butylamino-propyl)-3H-pyrrolo[2,1-f][1,
2,4]triazin-4-one (Example 33, 28.0 mg, 0.0828 mmol) in
$CHCl_3$ (5 mL) was treated with benzoylchloride (28.8 μL,
0.248 mmol) and $Et_3N$ (23.0 μL, 0.166 mmol), then stirred
for 18 h at 25° C. The mixture was concentrated under
vacuum and purified by preparative HPLC using a YMC S10
ODS 20×100 mm column affording the desired compound
(21.6 mg, 68%) as a colorless film: LC/MS 98% at 3.84 min
($ESI^+$) 443 ($M^+$+H).

Example 37

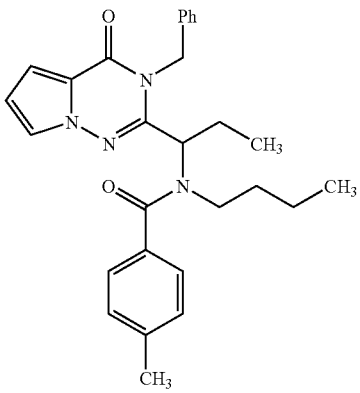

(±)-N-[1-(3-Benzyl-4-oxo-3,4-dihydro-pyrrolo[2,1-f]
[1,2,4]triazin-2-yl)-propyl]-N-butyl-4-methyl-benza-
mide, trifluoroacetic acid salt 3-Benzyl-2-(1-butylamino-propyl)-3H-pyrrolo[2,1-f][1,
2,4]triazin-4-one (Example 33, 28.0 mg, 0.0828 mmol) in
$CHCl_3$ (5 mL) was treated with p-toluoylchloride (32.9 μL,
0.248 mmol) and $Et_3N$ (23.0 μL, 0.166 mmol), then stirred
for 18 h at 25° C. The mixture was concentrated under
vacuum and purified by preparative HPLC using a YMC S10
ODS 20×100 mm column affording the desired compound
(24.2 mg, 64%) as a colorless film: LC/MS 93% at 3.96 min
($ESI^+$) 457 ($M^+$+H).

Example 38

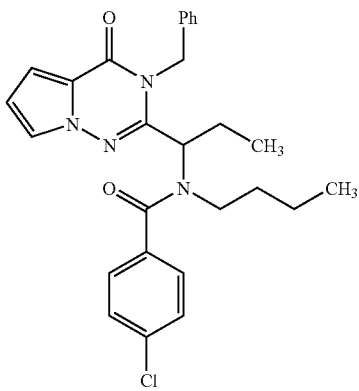

(±)-N-[1-(3-Benzyl-4-oxo-3,4-dihydro-pyrrolo[2,1-f]
[1,2,4]triazin-2-yl)-propyl]-N-butyl-4-chloro-benzamide, trifluoroacetic acid salt 3-Benzyl-2-(1-butylamino-propyl)-3H-pyrrolo[2,1-f][,2,4]triazin-4-one (Example 33, 28.0 mg, 0.0828 mmol) in CHCl$_3$ (5 mL) was treated with 4-chloro-benzoylchloride (31.5 μL, 0.248 mmol) and Et$_3$N (23.0 μL, 0.166 mmol), then stirred for 18 h at 25° C. The mixture was concentrated under vacuum and purified by preparative HPLC using a YMC S10 ODS 20×100 mm column affording the desired compound (24.2 mg, 45%) as a colorless film: LC/MS 92% at 4.02 min (ESI$^+$) 477 (M$^+$+H).

Example 39

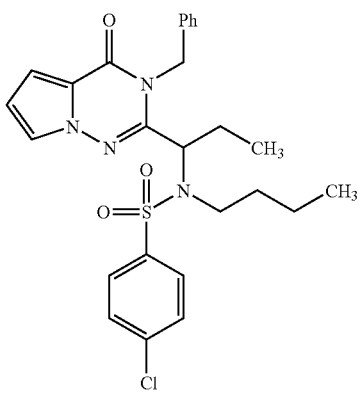

(±)-N-[1-(3-Benzyl-4-oxo-3,4-dihydro-pyrrolo[2,1-f]
[1,2,4]triazin-2-yl)-propyl]-N-butyl-4-chloro-benzenesulfonamide 3-Benzyl-2-(1-butylamino-propyl)-3H-pyrrolo[2,1-f][1,2,4]triazin-4-one (Example 33, 28.0 mg, 0.0828 mmol) in CHCl$_3$ (5 mL) was treated with 4-chloro-benzenesulfonylchloride (52.3 mg, 0.248 mmol) and Et$_3$N (23.0 μL, 0.166 mmol), then stirred for 18 h at 25° C. The mixture was concentrated under vacuum and purified by preparative HPLC using a YMC S10 ODS 20×100 mm column affording the desired compound (3.0 mg, 7.0%) as a colorless film: LC/MS 88% at 4.13 min (ESI$^+$) 513 (M$^+$+H).

Example 40

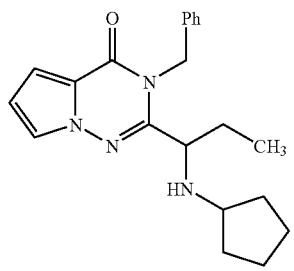

(±)-3-Benzyl-2-(1-cyclopentylamino-propyl)-3H-pyrrolo[2,1-f][1,2,4]triazin-4-one A mixture of 2-(1-amino-propyl)-3-benzyl-3H-pyrrolo[2,1-f][1,2,4]triazin-4-one (Example 26, 50 mg, 0.16 mmol), cyclopentanone (13 mg, 0.16 mmol), anhydrous sodium acetate (26 mg, 0.32 mmol), 4 Å molecular sieves (50 mg) and 1,4-dioxane (10 mL) was stirred at room temperture for 40 min. The mixture was treated with sodium triacetoxyborohydride (51 mg, 0.24 mmol) in one portion and stirred at room temperature for 40 h. Additional portions of cyclopentanone (0.16 mmol) and sodium triacetoxyborohydride (0.16 mmol) were added to the mixture which was stirred for an additional 3.5 hours then filtered. The filtrate was partitioned between ethyl acetate and saturated sodium bicarbonate, the ethyl acetate phase washed with brine, dried (MgSO$_4$) and concentrated. The residue was purified by flash column chromatography on silica gel eluting with ethyl acetate to give the title compound (40 mg, 71%): $^1$H NMR (DMSO-d$_6$) δ 0.88 (t, 3H, J=7.15 Hz), 0.95 (m, 1H), 1.05 (m, 1H), 1.20 (m, 1H), 1.31 (m, 1H), 1.33 (m, 1H), 1.50–1.72 (m, 6H), 2.72 (m, 1H), 3.53 (m, 1H), 4.95 (m, 1H), 5.58 (m, 1H), 6.54 (s, 1H), 7.08 (s, 1H) 7.16 (s 2H), 7.24–7.35 (m, 3H), 7.35 (s, 1H).

Example 41

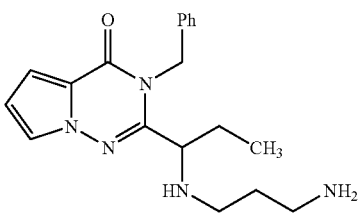

(±)-2-[1-(3-Amino propylamino)-propyl]-3-benzyl-3H-pyrrolo[2,1-f][1,2,4]triazin-4-one, bis trifluoroacetic acid salt A) (±)-{3-[1-(3-Benzyl-4-oxo-3,4-dihydro-pyrrolo[2,1-f][1,2,4]triazin-2-yl)-propylamino]-propyl}-carbamic acid 9H-fluoren-9-ylmethyl ester A mixture of 2-(1-amino-propyl)-3-benzyl-3H-pyrrolo[2,1-f][1,2,4]triazin-4-one (180 mg, 0.64 mmol), acetic acid (Example 26, 65 μl, 0.95 mmol), 3-oxo-propyl-carbamic acid 9H-fluoren-9-ylmethyl ester (*Org. Lett.* 2002, 4, 3001–3003), 1,4-dioxane (5 mL), and 4 Å molecular sieves was stirred at room temperature for 15 min then treated with sodium triacetoxyborohydride (112 mg, 0.53 mmol). After 45 min, the reaction was diluted with methylene chloride (25 mL), filtered, washed with saturated sodium bicarbonate, dried (MgSO$_4$) and concentrated. The residue was purified by flash column chromatography on silica gel eluting with ethyl acetate/hexanes to give the desired compound (170 mg, 32%): MS (ESI$^+$) 562.2 (M$^+$+H).

B) (±)-2-[1-(3-amino propylamino)-propyl]-3-benzyl-3H-pyrrolo[2,1-f][1,2,4]triazin-4-one, bis trifluoroacetic acid salt A solution of (3-{[1-(3-benzyl-4-oxo-3,4-dihydro-pyrrolo [2,1-!] [1,2,4]triazin-2-yl)-propyl]-cyclohexyl-amino}-propyl)-carbamic acid 9H-fluoren-9-yl methyl ester (56 mg, 0.10 mmol) in THF (4 mL) was treated with piperidine (0.5 mL) and stirred at room temperature for 3.5 h. The mixture was concentrated and the residue was purified by flash column chromatography on silica gel eluting with CH$_2$Cl$_2$/MeOH/NH$_4$OH (9:1:0.01, v/v/v). The fractions containing the product were combined and concentrated to give the title compound (10 mg, 18%) which was converted to the bis-trifluoroacetic acid salt by treatment with TFA/methanol followed by evaporation under vacuum: $^1$H NMR (DMSO-d$_6$) δ 1.85 (t, 3H, J=7.15 Hz), 1.39 (m, 2H), 1.61 (m, 1H), 1.75 (m, 1H), 2.32 (m, 1H), 2.55 (m, 1H), 3.40 (m, 2H), 3.48 (m, 1H), 5.44 (m, 2H), 6.66 (s, 1H), 7.02 (s, 1H), 7.24 (m, 2H), 7.30–7.36 (m, 1H), 7.39–7.42 (m, 3H), 7.68 (s, 1H); MS (ESI$^+$) 340.0 (M$^+$+H).

zaldehyde (249 mg, 2.34 mmol) were dissolved in CH$_3$OH (25 mL) and stirred for 1 h at 25° C. The mixture was then treated with NaBH(OAc)$_3$ (600 mg, 2.82 mmol) and stirred for 18 h. The reaction mixture was concentrated under vacuum and purified by preparative HPLC using a YMC S10 ODS 30×100 mm column affording Example 42 (250 mg, 71%) as a colorless film: $^1$H NMR (CD$_3$OD, 400 MHz) δ 7.59 (m, 1H), 7.20–7.40 (m, 10H), 7.15 (d, 2H, J=8 Hz), 7.12 (m, 1H), 6.67 (m, 1H), 5.3 (d, 1H, J=17 Hz), 5.14 (d, 1H, J=17 Hz), 4.5 (t, 1H, J=6 Hz), 4.13 (d, 1H, J=13 Hz), 4.03 (d, 1H, J=13 Hz), 1.95 (q, 2H, J=7 Hz), 0.75 (t, 3H, J=7 Hz); MS (ESI$^+$) 373 (M$^+$+H) and Example 43 (10.0 mg, 2.0%) as a white solid: $^1$H NMR (CD$_3$OD, 400 MHz) δ 7.45 (m, 1H), 7.24 (m, 8H), 7.20 (m, 2H), 7.11 (m, 3H), 6.52 (m, 3H), 5.58 (d, 1H, J=16.5 Hz), 4.68 (d, 1H, J=16.5 Hz), 4.00 (m, 2H), 3.73 (m, 3H), 2.26 (m, 1H), 2.02 (m, 1H), 0.60 (t, 3H, J=7.0 Hz); MS (ESI$^+$) 463 (M$^+$+H).

Example 44

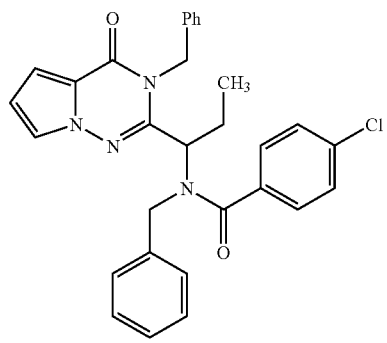

(±)—N-Benzyl-N-[1-(3-benzyl-4-oxo-3,4-dihydro-pyrrolo[2,1-f][1,2,4]triazin-2-yl)-propyl]-4-chloro-benzamide, trifluoroacetic acid salt 3-Benzyl-2-(1-benzylamino-propyl)-3H-pyrrolo[2,1-f][1,2,4]triazin-4-one (Example 42, 23.1 mg, 0.062 mmol) in CHCl$_3$ (5 mL) was treated with 4-chlorobenzoylchloride (43.4 mg, 0.248 mmol) and Et$_3$N (23.0 μL, 0.166 mmol), then stirred for 18 h at 25° C. The mixture was concentrated under vacuum and purified by preparative HPLC using a YMC S10 ODS 20×100 mm column affording the desired compound (20.5 mg, 65%) as a colorless film: LC/MS 88% at 3.89 min (ESI$^+$) 511 (M$^+$+H).

Example 42 and Example 43

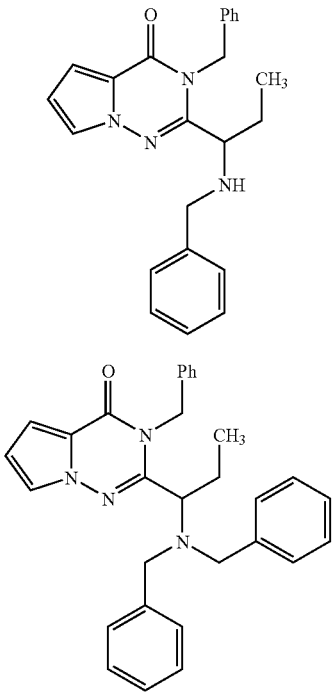

(±)-3-Benzyl-2-(1-benzylamino-propyl)-3H-pyrrolo [2,1-f][1,2,4]triazin-4-one, trifluoroacetic acid salt (Example 42) and (±)-3-Benzyl-2-(1-dibenzy-lamino-propyl)-3H-pyrrolo[2,1-f][1,2,4]triazin-4-one, trifluoroacetic acid salt (Example 43)

2-(1-Amino-propyl)-3-benzyl-3H-pyrrolo[2,1-f][1,2,4]triazin-4-one (Example 26, 300 mg, 0.94 mmol) and ben- Example 45

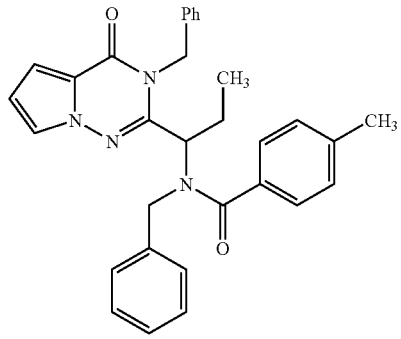

(±)-N-Benzyl-N-[1-(3-benzyl-4-oxo-3,4-dihydro-pyrrolo[2,1-f][1,2,4]triazin-2-yl)-propyl]-4-methyl-benzamide 3-Benzyl-2-(1-benzylamino-propyl)-3H-pyrrolo[2,1-f][,2,4]triazin-4-one (Example 42, 23.1 mg, 0.062 mmol) in CHCl₃ (5 mL) was treated with p-toluoylchloride (38.2 mg, 0.248 mmol) and Et₃N (23.0 µL, 0.166 mmol), then stirred for 18 h at 25° C. The mixture was concentrated under vacuum and purified by preparative HPLC using a YMC S10 ODS 20×100 mm column affording the desired compound (21.2 mg, 70%) as a colorless film: LC/MS 87% at 3.87 min (ESI⁺) 491 (M⁺+H).

Example 46

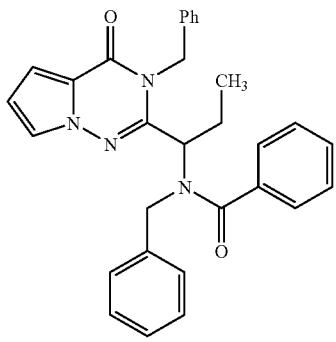

(±)-N-Benzyl-N-[1-(3-benzyl-4-oxo-3,4-dihydro-pyrrolo[2,1-f][1,2,4]triazin-2-yl)-propyl]-benzamide 3-Benzyl-2-(1-benzylamino-propyl)-3H-pyrrolo[2,1-f][1,2,4]triazin-4-one (Example 42, 23.1 mg, 0.062 mmol) in CHCl₃ (5 mL) was treated with benzoylchloride (28.8 µL, 0.248 mmol) and Et₃N (23.0 µL, 0.166 mmol), then stirred for 18 h at 25° C. The mixture was concentrated under vacuum and purified by preparative HPLC using a YMC S10 ODS 20×100 mm column affording the desired compound (22 mg, 83%) as a colorless film: LC/MS 87% at 3.72 min (ESI⁺) 477 (M⁺+H).

Example 47

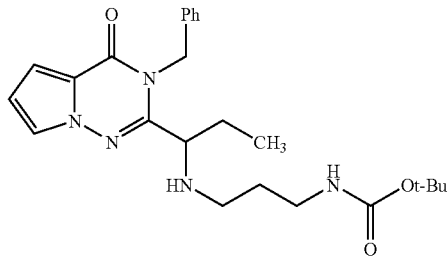

(±)-{3-[1-(3-Benzyl-4-oxo-3,4-dihydro-pyrrolo[2,1-f][1,2,4]triazin-2-yl)-propylamino]-propyl}-carbamic acid tert-butyl ester 2-(1-Amino-propyl)-3-benzyl-3H-pyrrolo[2,1-f][1,2,4]triazin-4-one (Example 26, 300 mg, 0.94 mmol) and (3-oxo-propyl)-carbamic acid tert-butyl ester (*J. Med. Chem.* 1985, 28, 317–323, 982 mg, 5.64 mmol) were dissolved in CH₃OH (20 mL) and stirred for 1 h at 25° C. The mixture was then treated with NaBH(OAc)₃ (1.19 g, 5.64 mmol) and stirred for 18 h. The reaction mixture was concentrated under vacuum and purified by preparative HPLC using a YMC S10 ODS 30×250 mm column affording the desired compound (300 mg, 73%) as a colorless film: ¹³C NMR (CD₃OD, 100 MHz) δ 160.8, 160.49, 154.89, 144.86, 136.06, 129.09, 128.04, 126.52, 121.79, 117.72, 115.16, 111.60, 109.53, 79.20, 57.97, 44.32, 27.38, 26.55, 25.5, 7.58; LC/MS (ESI⁺) 440 (M⁺+H).

Example 48

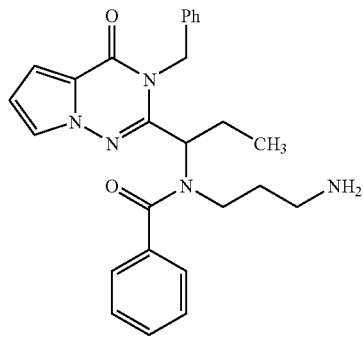

(±)-N-(3-Amino-propyl)-N-[1-(3-benzyl-4-oxo-3,4-dihydro-pyrrolo[2,1-f][1,2,4]triazin-2-yl)-propyl]-benzamide A) (±)-(2-{Benzoyl-[1-(3-benzyl-4-oxo-3,4-dihydro-pyrrolo[2,1-f][1,2,4]triazin-2-yl)-propyl]-amino}-1,1-dimethyl-ethyl)-carbamic acid tert-butyl ester {3-[1-(3-Benzyl-4-oxo-3,4-dihydro-pyrrolo[2,1-f][1,2,4]triazin-2-yl)-propylamino]-propyl}-carbamic acid tert-butyl ester (Example 47, 25 mg, 0.0569 mmol) in CHCl₃ (10 mL) at 25° C. was treated with benzoylchloride (28.8 µL, 0.248 mmol) and triethylamine (23.0 µL, 0.166 mmol). The resulting mixture was stirred at 25° C. for 18 h, then concentrated under vacuum and purified by preparative HPLC using a YMC S10 ODS 20×100 mm column affording the desired compound (13.7 mg, 44.3%) as a colorless film: LC/MS (ESI⁺) 558 (M⁺+H).

B) (±)-N-(3-Amino-propyl)-N-[1-(3-benzyl-4-oxo-3,4-dihydro-pyrrolo[2,1-f][1,2,4]triazin-2-yl)-propyl]-benzamide The above compound A was dissolved in CH₂Cl₂ (5 mL) and treated with TFA (1.0 mL). After stirring at 25° C. for 0.5 h, the mixture was concentrated under vacuum and purified by preparative HPLC using a YMC S10 ODS 20×100 mm column affording the desired compound (5.6 mg, 21.3%) as a colorless film: LC/MS (ESI⁺) 458 (M⁺+H).

Example 49

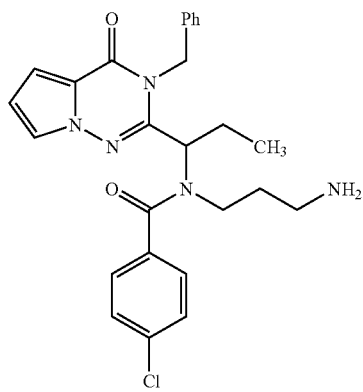

(±)-N-(3-Amino-propyl)-N-[1-(3-benzyl-4-oxo-3,4-dihydro-pyrrolo[2,1-f][1,2,4]triazin-2-yl)-propyl]-4-chloro-benzamide, trifluoroacetic acid salt A) (±)-{3-[[1-(3-Benzyl-4-oxo-3,4-dihydro-pyrrolo[2,1-f][1,2,4]triazin-2-yl)-propyl]-(4-chloro-benzoyl)-amino]-propyl}-carbamic acid tert-butyl ester {3-[1-(3-Benzyl-4-oxo-3,4-dihydro-pyrrolo[2,1-f][1,2,4]triazin-2-yl)-propylamino]-propyl}-carbamic acid tert-butyl ester (Example 47, 25 mg, 0.0569 mmol) in CHCl$_3$ (10 mL) at 25° C. was treated with 4-chloro-benzoylchloride (31.5 μL, 0.248 mmol) and triethylamine (23.0 μL, 0.166 mmol). The resulting mixture was stirred at 25° C. for 18 h, then concentrated under vacuum and purified by preparative HPLC using a YMC S10 ODS 20×100 mm column affording the desired compound (17.2 mg, 52.3%) as a colorless film: LC/MS 86% at 3.74 min (ESI$^+$) 578 (M$^+$+H).

B) (±)-N-(3-Amino-propyl)-N-[1-(3-benzyl-4-oxo-3,4-dihydro-pyrrolo[2,1-f][1,2,4]triazin-2-yl)-propyl]-4-chloro-benzamide, trifluoroacetic acid salt {3-[[1-(3-Benzyl-4-oxo-3,4-dihydro-pyrrolo[2,1-f][1,2,4]triazin-2-yl)-propyl]-(4-chloro-benzoyl)-amino]-propyl}-carbamic acid tert-butyl ester (14.8 mg, 0.026 mmol) in CH$_2$Cl$_2$ (5.0 mL) was treated with TFA (1.0 mL) and stirred at 25° C. for 0.5 h. The mixture was concentrated under vacuum and purified by preparative HPLC using a YMC S10 ODS 20×100 mm column affording the desired compound (6.5 mg, 52%) as a colorless film: LC/MS 82% at 2.98 min (ESI$^+$) 478 (M$^+$+H).

Example 50

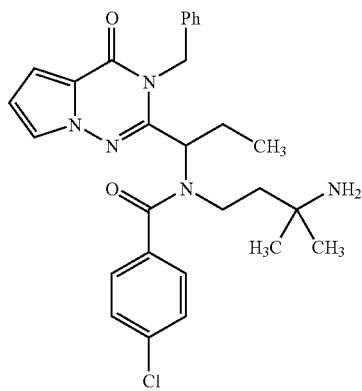

(±)-N-(3-Amino-3-methyl-butyl)-N-[1-(3-benzyl-4-oxo-3,4-dihydropyrrolo[2,1-f][1,2,4]triazin-2-yl)-propyl]-4-chloro-benzamide, trifluoroacetic acid salt A) 2,4,4-Trimethyl-5,6-dihydro-4H-[1,3]oxazine Acetonitrile (22.6 g, 0.25 mol) was dripped into concentrated H$_2$SO$_4$ (150 mL) at 0° C. Upon complete addition of acetonitrile, 3-methyl-butane-1,3-diol (Fluka, 22.6 g, 0.55 mol) was added over 0.5 h maintaining the reaction temperature at or below 5° C. The resulting mixture was stirred for 1.5 h at 5° C. then poured onto crushed ice. When the ice had melted, the aqueous was extracted with ether (2×250 mL). The organic was discarded and the aqueous was treated with 40% NaOH to pH 12. The basic aqueous was extracted with ether. The organic was washed with brine and dried (MgSO$_4$). The ether was removed under vacuum at 25° C. affording the desired product as a colorless oil (25.4 g, 50%): $^1$H NMR (DMSO-d$_6$) δ 4.04 (t, 2H, J=6 Hz), 1.72 (s, 3H), 1.61 (t, 2H, J=6 Hz), 1.07 (s, 6H).

B) 3-Amino-3-methyl-butan-1-ol 2,4,4-Trimethyl-5,6-dihydro-4H-[1,3]oxazine (25.2 g, 0.20 mol) was dissolved in 6 N NaOH (65 mL, 0.40 mol) and stirred at 80° C. for 18 h. The resulting mixture was cooled to 25° C. and extracted with CH$_2$Cl$_2$ (3×100 mL). The organic was dried (MgSO$_4$) and concentrated to afford the desired material as a colorless oil (5.1 g, 20%): $^1$H NMR (DMSO-d$_6$) δ 3.55 (t, 2H, J=7 Hz), 1.47 (t, 2H, J=7 Hz), 1.03 (s, 6H).

C) (3-Hydroxy-1,1-dimethyl-propyl)-carbamic acid tert-butyl ester

3-Amino-3-methyl-butan-1-ol (5.0 g, 0.04 mol) was dissolved in 150 mL CH$_2$Cl$_2$ and treated with di-tert-butyl dicarbonate (11.12 g, 0.05 mol). The resulting mixture was stirred for 18 h at 25° C. The mixture was concentrated to the desired material as an amber oil (9.8 g, 100%): $^1$H NMR (DMSO-d$_6$) δ 3.55 (s, 1H), 4.43 (t, 1H, J=5 Hz), 3.46 (m, 2H), 1.71 (t, 2H, J=7 Hz), 1.37 (s, 9H), 1.12 (s, 6H).

D) (1,1-Dimethyl-3-oxo-propyl)-carbamic acid tert-butyl ester (3-Hydroxy-1,1-dimethyl-propyl)-carbamic acid tert-butyl ester (9.8 g, 0.048 mol) was dissolved in DMSO (160 mL). The solution was treated with Et$_3$N (20.2 mL, 0.145 mol) followed by a solution of pyridine sufurtrioxide complex (23.2 g, 0.145 mol) in DMSO (160 mL). Upon complete addition, the solution was stirred for 1 h at 25° C. The mixture was diluted with brine and extracted with Et$_2$O (3×125 mL). The organic phase was washed with 10% citric acid(aq), saturated NaHCO$_3$ and brine. The organic phase was dried (MgSO$_4$) and concentrated to the desired material as a yellow oil (8.3 g, 56%): $^1$H NMR (DMSO-d$_6$) δ 9.67 (t, 1H, J=3 Hz), 2.66 (s, 2H), 1.37 (s, 9H), 1.28 (s, 6H).

E) (±)-{3-[1-(3-Benzyl-4-oxo-3,4-dihydro-pyrrolo[2,1-f][1,2,4]triazin-2-yl)-propylamino]-1,1-dimethyl-propyl}-carbamic acid tert-butyl ester (1,1-Dimethyl-3-oxo-propyl)-carbamic acid tert-butyl ester (19 mg, 0.564 mmol) and 2-(1-amino-propyl)-3-benzyl-3H-pyrrolo[2,1-f][1,2,4]triazin-4-one (Example 26, 120 mg, 0.376 mmol) were stirred in CH$_3$OH (10 mL) for 1 h at 25° C. The mixture was then treated with NaBH(OAc)$_3$ (119 mg, 0.564 mmol) and stirred for 12 h at 25° C. The mixture was concentrated under vacuum and purified by preparative HPLC using a YMC S10 ODS 30×100 mm column affording the desired material (100 mg, 57%) as a colorless oil: $^{13}$C NMR (CDCl$_3$ 100 MHz) δ 161.54, 154.93, 154.42, 144.72, 135.84, 129.53, 128.58, 127.27, 121.99, 117.28, 114.95, 111.94, 110.48, 79.81, 58.05, 51.12, 44.61, 43.07, 35.91, 28.17, 27.07, 26.53, 8.55; LC/MS (ESI$^+$) 468 (M$^+$+H).

F) (±)-N-(3-Amino-3-methyl-butyl)-N-[1-(3-benzyl-4-oxo-3,4-dihydropyrrolo[2,1-f][1,2,4]triazin-2-yl)-propyl]-4-chloro-benzamide, trifluoroacetic acid salt The above product E (80 mg, 0.171 mmol) was dissolved in CHCl$_3$ (30 mL) and treated with 4-chloro-benzoylchloride (89.9 mg, 0.514 mmol) and triethylamine (34.7 mg, 0.34 mmol). The resulting mixture was stirred at 25° C. for 18 h. The mixture was concentrated under vacuum and purified by preparative HPLC using a YMC S10 ODS 30×100 mm column affording a colorless film. The residue was dissolved in CH$_2$Cl$_2$ (10.0 mL) and treated with TFA (1.5 mL). The mixture was stirred at 25° C. for 1 h, then concentrated in vacuo affording the desired material as a white solid (40 mg, 46%): $^1$H NMR (DMSO-$d_6$, 400 MHz) δ 7.57 (m, 3H), 7.39 (m, 2H), 7.25 (m, 2H), 7.13 (m, 3H), 6.95 (m, 1H), 6.59 (s, 1H), 5.65 (m, 2H), 5.55 (d, 1H, J=17 Hz), 4.78 (d, 1H, J=17 Hz), 3.15 (m, 2H), 1.99 (m, 1H), 1.77 (m, 1H), 1.45 (m, 1H), 1.14 (m, 2H), 0.68 (s, 6H), 0.65 (s, 3H); LC/MS (ESI$^+$) 506 (M$^+$+H).

Example 51

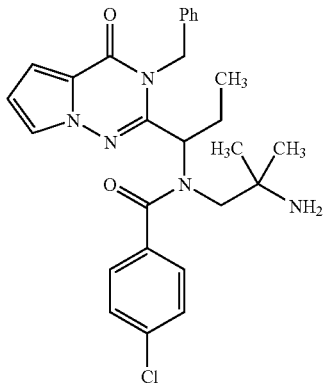

(±)-N-(2-Amino-2-methyl-propyl)-N-[1-(3-benzyl-4-oxo-3,4-dihydro-pyrrolo[2,1-f][1,2,4]triazin-2-yl)-propyl]-4-chloro-benzamide, trifluoroacetic acid salt A) (2-Hydroxy-1,1-dimethyl-ethyl)-carbamic acid tert-butyl ester 2-Amino-2-methyl-propan-1-ol (53 g, 0.59 mol) and di-tert-butyl dicarbonate (65.0 g, 0.297 mol) were combined in H$_2$O (500 mL) and stirred at 25° C. for 1 h. The reaction mixture was extracted with CHCl$_3$ (2×250 mL) The organics were dried and concentrated to a white amorphous solid which was recrystallized from hot hexanes to afford desired material (30 g, 53%) as a white solid: $^{13}$C NMR (CD$_3$OD, 100 MHz) δ 157.76, 80.135, 70.095, 54.992, 29.247, 24.695.

B) (1,1-Dimethyl-2-oxo-ethyl)-carbamic acid tert-butyl ester (2-Hydroxy-1,1-dimethyl-ethyl)-carbamic acid tert-butyl ester (11.3 g, 0.06 mol) and triethylamine (18.2 g, 0.18 mol) in DMSO (180 mL) at 25° C. was treated with a solution of pyridine-sulfurtrioxide complex (28.6 g, 0.18 mol) in DMSO (150 mL). The resulting mixture was stirred for 0.5 h, poured into H$_2$O (100 mL) and extracted with ether (3×100 mL). The organics were washed with 10% citric acid$_{(aq)}$ (250 mL), saturated NaHCO$_3$ (250 mL) and then with brine (2×250 mL). The organics were dried and concentrated to an off-white solid which was recrystallized from hexanes to afford the desired material (8.0 g, 71%) as white needles: $^{13}$C NMR (DMSO-$d_6$, 100 MHz) δ 202.07, 155.58, 78.95, 58.64, 28.42, 21.58.

C) (±)-{2-[1-(3-Benzyl-4-oxo-3,4-dihydro-pyrrolo[2,1-f][1,2,4]triazin-2-yl)-propylamino]-1,1-dimethyl-ethyl}-carbamic acid tert-butyl ester (1,1-Dimethyl-2-oxo-ethyl)-carbamic acid tert-butyl ester (88.0 mg, 0.047 mmol) and 2-(1-amino-propyl)-3-benzyl-3H-pyrrolo[2,1-f][1,2,4]triazin-4-one (Example 26, 100 mg, 0.314 mmol) in CH$_3$OH (20 mL) was stirred at 25° C. for 1 h and then treated with NaCNBH$_3$ (29.5 mg, 0.47 mmol). The mixture was stirred for 0.5 h at which time a white precipitate had formed. The precipitate was collected, washed with cold CH$_3$OH and air dried to afford the desired material (55 mg, 39%) as a white crystalline solid: $^1$H NMR (DMSO-$d_6$, 400 MHz) δ 7.36 (s, 1H), 7.10 (m, 5H), 6.82 (s, 1H), 6.46 (s, 1H), 5.47 (s, 1H), 5.20 (m, 2H), 3.55 (s, 1H), 2.45 (s, 1H), 2.22 (s, 1H), 1.84 (s, 1H), 1.64 (m, 1H), 1.53 (m, 1H), 1.26 (s, 9H), 1.01 (s, 6H), 0.72 (m, 3H).

D) (±)-{2-[[1-(3-Benzyl-4-oxo-3,4-dihydro-pyrrolo[2,1-f][1,2,4]triazin-2-yl)-propyl]-(4-chloro-benzoyl)-amino]-1,1-dimethyl-ethyl}-carbamic acid tert-butyl ester {2-[1-(3-Benzyl-4-oxo-3,4-dihydro-pyrrolo[2,1-f][1,2,4]triazin-2-yl)-propylamino]-1,1-dimethyl-ethyl}-carbamic acid tert-butyl ester (70 mg, 0.15 mmol) and 4-chlorobenzoylchloride (81.0 mg, 0.463 mmol) in CHCl$_3$ (20 mL) was treated with Et$_3$N (20.8 mg, 0.385 mmol). The reaction mixture was stirred at 25° C. for 18 h then concentrated under vacuum. The residue was and purified by preparative HPLC using a YMC S10 ODS 30×100 mm column to afford the desired material (52.2 mg, 57%) as a white powder: $^1$H NMR (CD$_3$OD, 400 MHz) δ 7.55 (s, 1H), 7.45 (m, 5H), 7.08 (m, 1H), 6.67 (m, 1H), 5.87 (m, 1H), 3.93 (m, 1H), 3.72 (m, 1H), 3.48 (m, 1H), 3.30 (s, 1H), 1.81 (m, 1H), 1.38 (s, 9H), 1.17 (m, 3H), 0.90 (m, 3H), 0.54 (m, 3H); LC/MS (ESI$^+$) 592 (M$^+$+H).

E) (±)-N-(2-Amino-2-methyl-propyl)-N-[1-(3-benzyl-4-oxo-3,4-dihydro-pyrrolo[2,1-f][1,2,4]triazin-2-yl)-propyl]-4-chloro-benzamide, trifluoroacetic acid salt {2-[[1-(3-Benzyl-4-oxo-3,4-dihydro-pyrrolo[2,1-f][1,2,4]triazin-2-yl)-propyl]-(4-chloro-benzoyl)-amino]-1,1-dimethyl-ethyl}-carbamic acid tert-butyl ester (50 mg, 0.085 mmol) was dissolved in CH$_2$Cl$_2$ (5.0 mL) and treated with TFA (1.0 mL). The mixture was stired at 25° C. for 1 h then concentrated in vacuo to afford the desired material as a white solid (20.5 mg, 50%): $^{13}$C NMR (CD$_3$OD, 100 MHz) δ 175.41, 156.41, 146.25, 138.63, 136.33, 134.55, 130.91, 130.22, 130.02, 129.03, 126.56, 123.37, 118.9, 113.54, 111.07, 62.08, 55.77, 52.13, 44.77, 27.42, 26.35, 22.95, 10.54; LC/MS (ESI$^+$) 492 (M$^+$+H).

Example 52

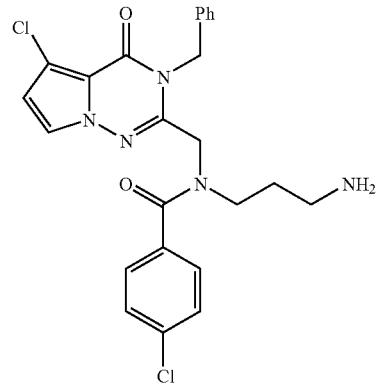

(±)-N-(3-Amino-propyl)-N-(3-benzyl-5-chloro-4-oxo-3,4-dihydro-pyrrolo [2,1-f][1,2,4]triazin-2-ylmethyl)-4-chloro-benzamide, hydrochloride salt A) (±)-{3-[(3-Benzyl-5-chloro-4-oxo-3,4-dihydro-pyrrolo[2,1-f][1,2,4]triazin-2-ylmethyl)-amino]-propyl}-carbamic acid tert-butyl ester To a solution of 3-benzyl-5-chloro-4-oxo-3,4-dihydro-pyrrolo[2,1-f][1,2,4]triazine-2-carbaldehyde (Example 22

E, 50 mg, 0.17 mmol) in EtOH (1 mL) was added 4 A molecular sieves (50 mg), (3-amino-propyl)-carbamic acid tert-butyl ester (Fluka, 33 mg, 0.19 mmol) and NaBH(OAc)$_3$ (55 mg, 0.26 mmol) under Ar. The reaction mixture was stirred at rt for 2 h, filtered and the filtrate was concentrated in vacuo. The residue was purified by flash column chromatography (SiO$_2$, 1–2% MeOH/CHCl$_3$) to afford the desired compound, as a colorless oil (12 mg, 16%): MS (ESI$^+$) 446 (M$^+$+H).

B) (±)-N-(3-Amino-propyl)-N-(3-benzyl-5-chloro-4-oxo-3,4-dihydro-pyrrolo[2,1-f][1,2,4]triazin-2-ylmethyl)-4-chloro-benzamide, hydrochloride salt To a solution of (±)-{3-[(3-benzyl-5-chloro-4-oxo-3,4-dihydro-pyrrolo[2,1-f][1,2,4]triazin-2-ylmethyl)-amino]-propyl}-carbamic acid tert-butyl ester (12 mg, 0.027 mmole) in methylene chloride (0.5 mL) at 0° C. was added Et$_3$N (11 μL, 0.081 mmole) followed by 4-chlorobenzoyl chloride (10 mL, 0.081 mmol). After stirring at 0° C. for 1.5 h, the reaction was quenched with 10 mL of saturated NaHCO$_3$ solution and extracted with EtOAc (3×20 mL). The pooled organic extracts were dried over anhydrous MgSO$_4$ and concentrated in vacuo. Purification of the residue by flash column chromatography (SiO$_2$, 2% MeOH/CHCl$_3$) gave a residue which was immediately treated with 4 N HCl in dioxane (1 mL). The crude product was lyophilized with acetonitrile/water to give the title compound as a white powder (7.2 mg, 51%): MS (ESI$^+$) 484 (M$^+$+H).

The invention claimed is:

1. A compound having formula I

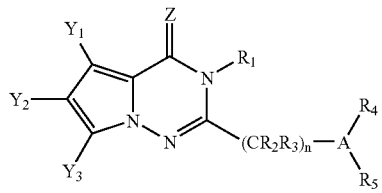

I or its enantiomer, diastereomer, or pharmaceutically acceptable salt thereof, wherein:

$Y_1$, $Y_2$, and $Y_3$ are independently H, halogen, —CN, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, —OR$_6$, —NR$_7$R$_8$, —C(=O)R$_9$, —C(=O)OR$_{10}$, —C(=O)NR$_{11}$R$_{12}$, —OC(=O)OR$_{10}$, —OC(=O)NR$_{11}$,R$_{12}$, —NR$_{13}$C(=O)OR$_{10}$, —NR$_{13}$C(=O)NR$_{11}$R$_{12}$, —SO$_2$R$_9$, —SO$_2$NR$_{11}$R$_{12}$, —NR$_{13}$SO$_2$NR$_{11}$R$_{12}$;

Z is O or S;

$R_1$ is H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, aralkyl, substituted aralkyl, heteroarylalkyl, or substituted heteroarylalkyl;

$R_2$ and $R_3$ are independently H, halogen, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, or taken together to form a carbocyclic or heterocyclic ring of 3 to 8 atoms;

n=1 to 4;

A is O, S or N with the proviso that when A is O or S, $R_5$ is nonexistent;

$R_4$ and $R_5$ are independently H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, aralkyl, C(=O)R$_9$, C(=O)OR$_{10}$, C(=O)NR$_{11}$R$_{12}$, SO$_2$R$_9$, SO$_2$NR$_{11}$R$_{12}$, or in the case of A being N, taken together to form a carbocyclic or heterocyclic ring of 3 to 8 atoms;

$R_6$, $R_7$, and $R_8$ are independently H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, —C(=O)H, —C(=O)alkyl, —C(=O)substituted alkyl, —C(=O)alkenyl, —C(=O)substituted alkenyl, —C(=O)alkynyl, —C(=O)substituted alkynyl, —C(=O)aryl, —C(=O)substituted aryl, —C(=O)heteroaryl, —C(=O)substituted heteroaryl, or $R_7$ and $R_8$ may be taken together to form a carbocyclic or heterocyclic ring of 3 to 8 atoms;

$R_9$, $R_{10}$, $R_{11}$, $R_{12}$, $R_{13}$ are independently H, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, or $R_{11}$ and $R_{12}$ may be taken together to form a carbocyclic or heterocyclic ring of 3 to 8 atoms.

2. The compound of claim 1 wherein n is 1.

3. The compound of claim 1 wherein $R_1$ is a substituted alkyl.

4. The compound of claim 3 wherein said alkyl is substituted with an aryl group.

5. The compound of claim 1 wherein $R_1$ is benzyl.

6. The compound of claim 1 wherein $Y_1$, $Y_2$, and $Y_3$ are, independently, hydrogen or halogen.

7. The compound of claim 1 wherein $R_2$ is H.

8. The compound of claim 1 wherein $R_3$ is alkyl.

9. The compound of claim 8 wherein $R_3$ is ethyl or cyclopropyl.

10. The compound of claim 1 wherein $R_4$ is a —C(O)—$R_9$.

11. The compound of claim 10 wherein $R_9$ is aryl or substituted aryl.

12. The compound of claim 1 wherein $R_5$ is a substituted alkyl.

13. The compound of claim 1 wherein $R_5$ is aminopropyl.

14. The compound of claim 1 wherein said salt is a trifluoroacetic acid salt.

15. The compound of claim 1 selected from the group consisting of (±)-N-(3-Aminopropyl)-N-[1-(3-benzyl-4-oxo-3,4-dihydropyrrolo[2,1-f][1,2,4]-triazine-2-yl)-propyl]-4-methylbenzamide, trifluoroacetic acid salt;

(±)-N-(3-Aminopropyl)-N-[1-(3-benzyl-5-chloro-4-oxo-3,4-dihydropyrrolo[2,1-f][1,2,4]-triazine2-yl)-propyl]-4-methylbenzamide, trifluoroacetic acid salt;

N-(3-Aminopropyl)-N-[1-(3-benzyl-5-chloro-4-oxo-3,4-dihydropyrrolo [2,1-f][1,2,4]triazin-2-yl)-propyl]-4-methylbenzamide, hydrochloric acid salt (±)-(3-Amino-propyl)-N-[1-(3-benzyl-4-oxo-3,4-dihydro-pyrrolo[2,1-f][1,2,4]triazin-2-yl)-propyl]-4-chloro-benzamide, hydrochloride salt;

(±)-N-(3-Aminopropyl)-N-[1-(3-benzyl-7-chloro-4-oxo-3,4-dihydropyrrolo[2,1-f][1,2,4]-triazine-2-yl)-propyl]-4-methylbenzamide, hydrochloride salt;

(±)-N-(3-Aminopropyl)-N-[1-(3-benzyl-7-chloro-4-oxo-3,4-dihydro-pyrrolo[2,1-f][1,2,4]triazin-2-yl)-propyl]-4-chlorobenzamide, trifluoroacetic acid salt;

(±)-N-(3-Amino-propyl)-N-[(3-benzyl-7-chloro-4-oxo-3,4-dihydro-pyrrolo[2,1-f][1,2,4]triazin-2-yl)-cyclopropyl-methyl]-4-methyl-benzamide, hydrochloride salt;

(±)-N-(3-Amino-3-methyl-butyl)-N-[(3-benzyl-7-chloro-4-oxo-3,4-dihydro-pyrrolo[2,1-f][1,2,4]triazin-2-yl)-cyclopropyl-methyl]-4-chlorobenzamide, trifluoroacetic acid salt;

(±)-N-(3-Amino-3-methyl-butyl)-N-[(3-benzyl-7-chloro-4-oxo-3,4-dihydropyrrolo[2,1-f][1,2,4]triazin-2-yl)-cyclopropyl-methyl]-4-methyl-benzamide, trifluroacetic acid;

(±)-N-(3-Amino-propyl)-N-[(3-benzyl-5-chloro-4-oxo-3,4-dihydro-pyrrolo[2,1-f][1,2,4]triazin--2-yl)-cyclopropyl-methyl]-4-methyl-benzamide, hydrochloride salt;

(±)-N-(3-amino-propyl)-N-[(3-benzyl-5-chloro-4-oxo-3,4-dihydro-pyrrolo[2,1-f][1,2,4]triazin--2-yl)-cyclopropyl-methyl]-4-chloro-benzamide, hydrochloride salt;

(±)-N-(3-Amino-propyl)-N-[1-(3-benzyl-4-oxo-3,4-dihydro-pyrrolo[2,1-f][1,2,4]triazin-2-yl)-propyl]-benzamide; and (±)-N-(3-Amino-propyl)-N-[1-(3-benzyl-4-oxo-3,4-dihydro-pyrrolo[2,1-f][1,2,4]triazin-2-yl)-propyl]-4-chloro-benzamide, trifluoroacetic acid salt.

16. A pharmaceutical composition comprising the compound of claim 1 and a pharmaceutically acceptable carrier.

17. The pharmaceutical composition of claim 16 further comprising at least one other anti-cancer drug.

* * * * *